US006936253B1

(12) United States Patent  (10) Patent No.: US 6,936,253 B1
Livingston et al.  (45) Date of Patent: Aug. 30, 2005

(54) GANGLIOSIDE-KLH CONJUGATE VACCINES PLUS QS-21

(75) Inventors: Philip Ordway Livingston, New York, NY (US); Friedhelm Helling, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 08/477,097

(22) Filed: Jun. 7, 1995

Related U.S. Application Data

(63) Continuation of application No. PCT/US94/00757, filed on Jan. 21, 1994, and a continuation-in-part of application No. 08/009,268, filed on Jan. 22, 1993, now abandoned.

(51) Int. Cl.$^7$ ....................... A61K 39/385; A61K 39/39
(52) U.S. Cl. ............................... 424/194.1; 424/193.1; 424/195.11; 424/282.1; 424/277.1; 424/278.1; 514/23; 514/25
(58) Field of Search ........................... 424/193.1, 194.1, 424/195.11, 282.1, 277.1, 278.1, 195.1, 280.1, 297.1; 514/23, 25, 24, 53, 54, 65, 762, 777, 64, 71

(56) References Cited

U.S. PATENT DOCUMENTS

| | | | | |
|---|---|---|---|---|
| 4,356,170 A | * | 10/1982 | Jennings et al. | ......... 424/194.1 |
| 4,557,931 A | | 12/1985 | Irie et al. | |
| 4,591,552 A | * | 5/1986 | Neurath | ......................... 435/5 |
| 4,652,629 A | * | 3/1987 | Patrick et al. | ............... 530/326 |
| 4,879,213 A | * | 11/1989 | Fox et al. | ........................ 435/5 |
| 5,102,663 A | | 4/1992 | Livingston et al. | |
| 5,256,409 A | * | 10/1993 | Blincko | .................... 424/175.1 |
| 5,344,870 A | * | 9/1994 | Ratcliffe et al. | ............ 525/54.2 |
| 5,599,914 A | * | 2/1997 | Wiegand et al. | |
| 5,616,477 A | | 4/1997 | Price | |

OTHER PUBLICATIONS

Tsuchida, Journal of the National Cancer Institute, 78: 45–54, 1987.*
Livingston, Proc. Natl. Acad. Sci. USA, 84: 2911–2915, 1987.*
Fiume, L. et al. Critical Reviews in Therapeutic Drug Carrier Systems, 4(4): 265–284, 1988.*
Harlow and Lane, Antibodies, A Laboratory Manual, pp. 84–85, 1988.*
Uemura et al J. Biochem 79(6):1753–1761, 1976.*
Laine et al, Journal of Biological Chemistry 249(14):4460–4466, 1974.*
J.A. Parsons (ed) "Peptide Hormones", see Chapter 1, pp. 1–7, Jun. 1976.*
Burgess et al. The Journal of Cell Biology 111:2129–38, Nov. 1990.*
Lazar et al. Mol. Cell Biol. 8(3):1247–52, Mar. 1988.*
Salgaller et al. Cancer Immunology Immunotherapy 39:105–116, 1994.*
Cohen et al. Science 262:841–843, Nov. 1993.*

Fung, P.Y.S. et al., "Active Specific Immunotherapy of a Murine Mammary Adenocarcinoma Using a Synthetic Tumor–Associated Glycoconjugate", Cancer Research, Jul. 15, 1990, vol. 50, pp. 4308–4314 (Exhibit 4).
Kensil, R.C., et al., "Separation and Characterization of Saponins With Adjuvant Activity from *Quillaja saponaria* Molina Cortex", The Journal of Immunology, Jan. 15, 1991, vol. 146, No. 2, pp. 431–437 (Exhibit 5).
Livingston, P.O., et al., "Characterization of IgG and IgM Antibodies Induced in Melanoma Patients by Immunization with Purified $G_{M2}$ Ganglioside", Cancer Research, Dec. 15, 1989, vol. 49, pp. 7045–7050 (Exhibit 6).
Livinsgton P.O., et al., "Studies on the Immunogenicity of Synthetic and Natural Thomsen–Friedhenreich (TF) Antigens in Mice: Augmentation of the Response by Quil A and SAF–m Adjuvants and Analysis of the Specificity of the Responses", Vaccine Research, vol. 1, No. 2, 1992, pp. 99–109 (Exhibit 7).
MacLean G.D et al., "Immunization of Breast Cancer Patients Using a Synthetic Sialyl–Tn Glycoconjugate Plus Detox Adjuvant", Cancer Immunol. Immunother., vol. 36, 1993, pp. 215–222 (Exhibit 8).
MacLean G.D., et al., "Active Immunization of Human Ovarian Cancer Patients Against a Common Carcinoma (Thomsen–Friedenreich) Determinant Using a Synthetic Carbohydrate Antigen", Journal of Immunotherapy, vol. 11, 1992, pp. 292–305 (Exhibit 9).
Marciani D.J., et al., "Genetically–engineered Subunit Vaccine Against Feline Leukaemia Virus: Protective Immune Response in Cats", Vaccine, vol. 9, Feb. 1991, pp. 89–96 (Exhibit 10).
Newman J.M., et al., "Saponin Adjuvant Induction of Ovalbumin–Specific $CD8^+$ Cytotoxic T Lymphocyte Responses", The Journal of Immunology, vol. 148, No. 8, Apr. 15, 1992, pp. 2357–2362 (Exhibit 11).
Ritter G., et al., "Ganglioside Antigens Expressed by Human Cancer Cells", Seminars in Cancer Biology, vol. 2, 1991, pp. 401–409 (Exhibit 12).
Ritter, G., et al., "Antibody Response to Immunization with Purified GD3 Ganglioside and GD3 Derivatives (Lactones, Amide and Gangliosidol) in the Mouse", Immunobiol., 1990, vol. 182 pp. 32–43 (Exhibit 13).
Ritter G., et al., "Ganglioside Antigens Expressed by Human Cancer Cells", Seminars in Cancer Biology, vol. 2, 1991, pp. 401–409 (Exhibit 12).

(Continued)

*Primary Examiner*—Alana M. Harris
*Assistant Examiner*—Anne L. Holleran
(74) *Attorney, Agent, or Firm*—John P. White, Esq.; Cooper & Dunham LLP

(57) ABSTRACT

This invention provides a vaccine for stimulating or enhancing in a subject to which the vaccine is administered, production of an antibody which recognizes a ganglioside, comprising an amount of ganglioside or oligosaccharide portion thereof conjugated to an immunogenic protein effective to stimulate or enhance antibody production in the subject, an effective amount of adjuvant and a pharmaceutically acceptable vehicle.

19 Claims, 26 Drawing Sheets

OTHER PUBLICATIONS

Figure 1A:
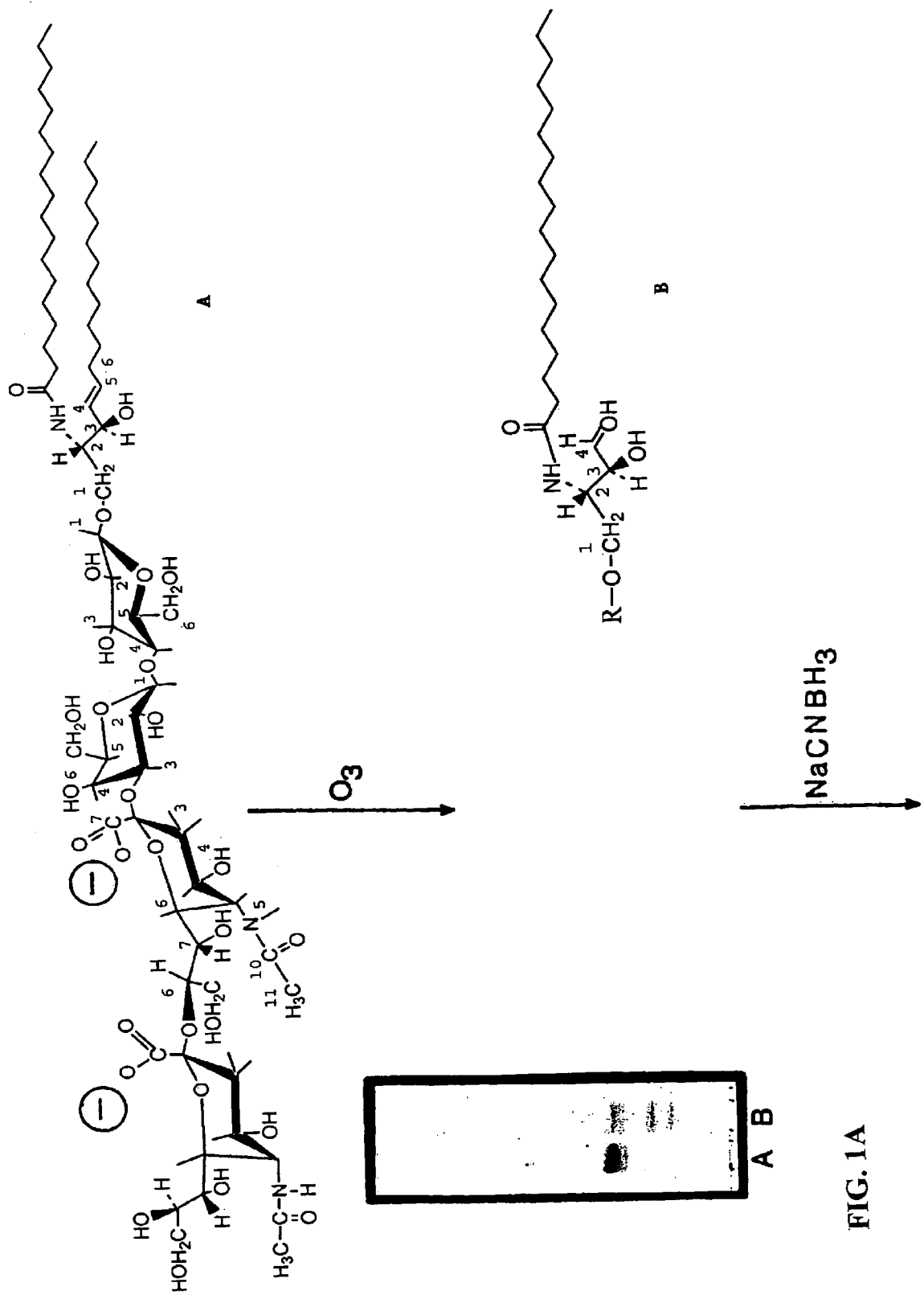

Ritter, G., et al., "Antibody Response to Immunization with Purified GD3 Ganglioside and GD3 Derivatives (Lactones, Amide and Gangliosidol) in the Mouse", Immunobiol., 1990, vol. 182 pp. 32–43 (Exhibit 13).

Wu J–Y. et al., "Saponin Adjuvant Enhancement of Antigen–Specific Immune Responses to an Experimental HIV–1 Vaccine", The Journal of Immunology, vol. 148, 1992, pp. 1519–1525 (Exhibit 14).

Helling, F., et al. "Increased immunogenicity of GM2 conjugated with KLH and used with adjuvants in patients with melanoma," Mar. 1993 *Proceedings Of The 84th Annual Meeting Of The American Association For Cancer Research* 34: 491.

Helling, F., et al. "Construction of immunogenic GD–3 conjugate vaccines." Aug. 1993 *Annals Of The New York Academy of Sciences* 690: 396–397.

Helling, F., et al. "GD–3 vaccines for melanoma superior immunogenicity of key hole limpet hemocyanin conjugate." 1994 *Cancer Research 54*: 197–203.

Bystryn, J–C, "Tumor vaccines," 1990 Cancer And Metastasis Reviews, 9: 81–91.

Ritter, G., et al. "Antibody response to immunization with ganglioside GD3 and GD3 congeners (lactones, amide and gangliosidol) in patients with malignant melanoma." 1991, *Int. J. Cancer* 48: 379–385.

* cited by examiner

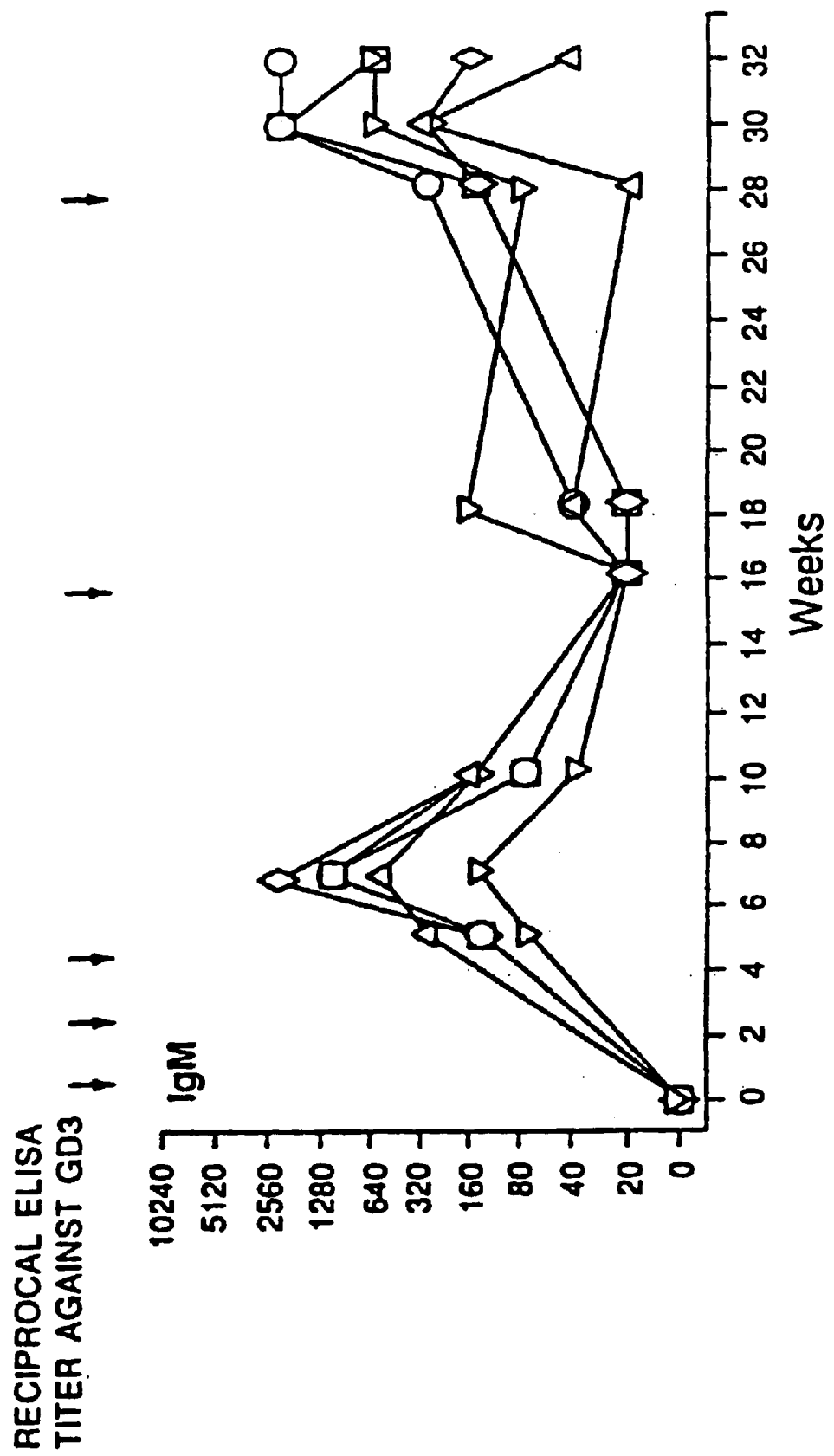

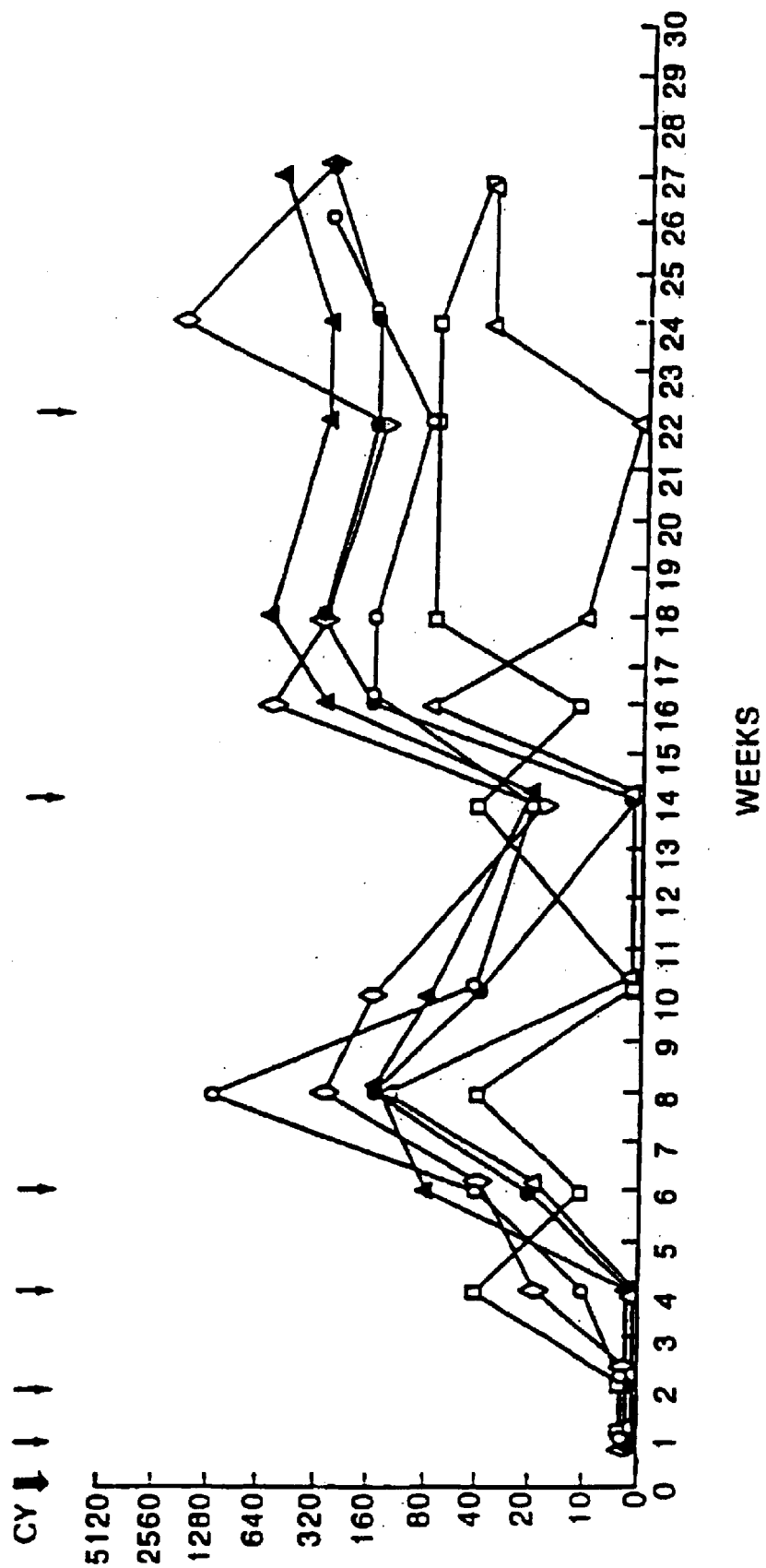

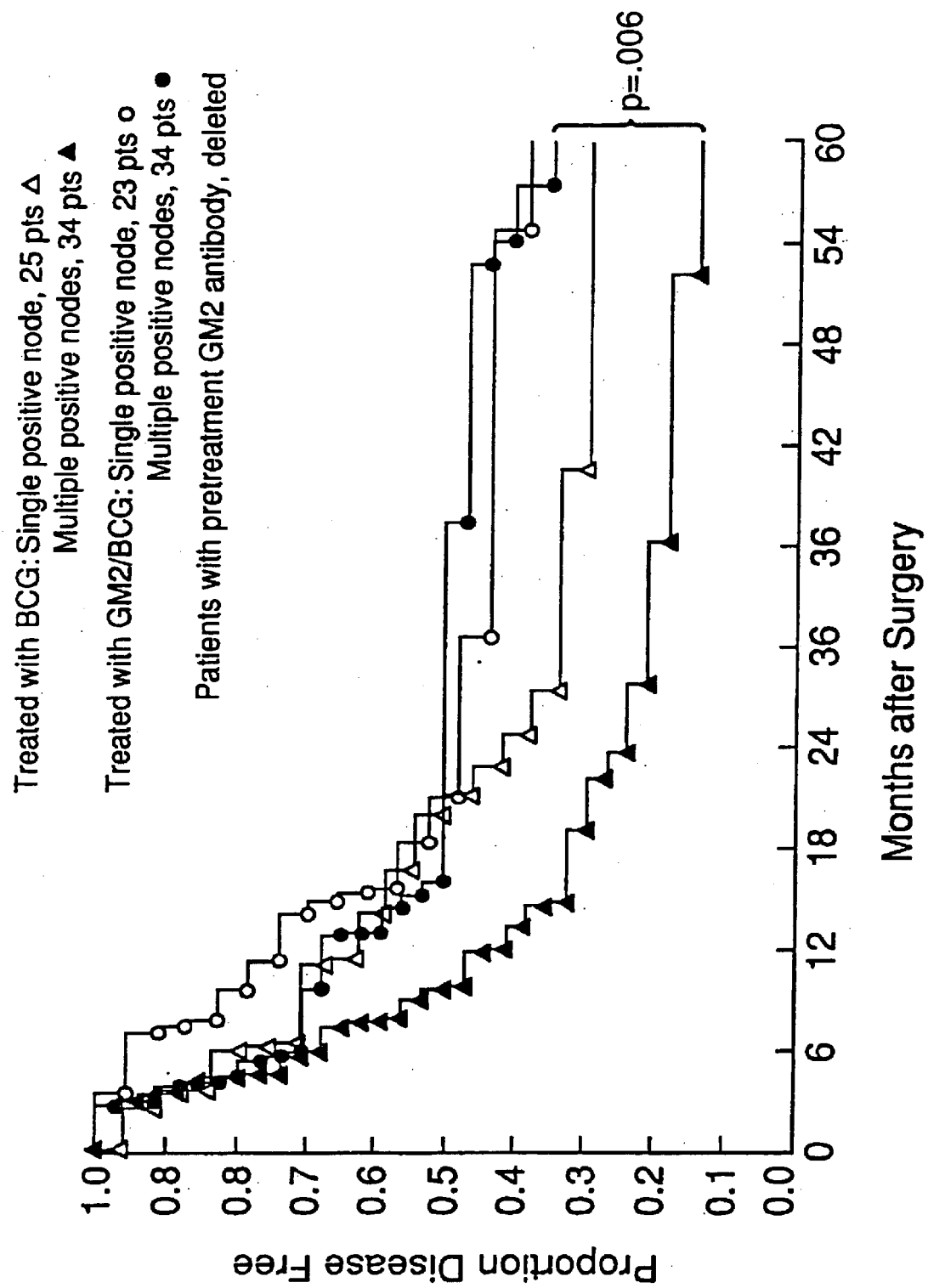

GANGLIOSIDE-KLH CONJUGATE VACCINES PLUS QS-21

This application is a continuation of PCT/US94/00757, filed Jan. 21, 1994, which claims priority of and is a continuation-in-part of U.S. Ser. No. 08/009,268, filed Jan. 22, 1993, now abandoned.

This invention was made with support under Government Grant No. RO1 CA40532. Accordingly, the U.S. Government has certain rights in the invention.

BACKGROUND OF THE INVENTION

Gangliosides are sialic acid containing glycosphingolipids composed of a complex carbohydrate moiety linked to a hydrophobic ceramide portion. Embedded within the outer leaflet of the cell membrane, the carbohydrate chain is exposed to the extracellular matrix. Qualitative and quantitative changes in ganglioside composition during cell differentiation and proliferation have been observed and seem to reflect the state of malignant transformation of cancers of neuroectodermal origin (Hakomori 1985). Malignant melanoma cells express a variety of complex gangliosides in addition to GM3, the major ganglioside in normal melanoctyes (Carubia et al. 1984). Altered ganglioside metabolism in melanoma causes additional expression of GD3, GD2, GM2,9-O-Acetyl-GD3 and GT3 (Hamilton et al. 1993; Tsuchida et al., 1987). Treatment of patients with anti-GD3 monoclonal antibodies resulted in inflammation at the tumor site and partial regression of metastasis was seen occasionally, suggesting, that gangliosides are suitable targets for immune attack (Houghton et al., 1985). The generation of human MAb's reactive with GD3 from melanoma patients (Yamaguchi et al., 1987) support the idea, that gangliosides are potential immunogens as well.

In studies aimed at inducing a humoral response against gangliosides in melanoma patients by active immunization, GM2/BCG vaccines seemed to be most effective (Livingston et al., 1987; Livingston et al., 1989). In a randomized study with 122 melanoma patients, who were disease-free after surgery, that it was showed that, out of 64 patients treated with BCG alone and 58 patients with GM2/BCG, the majority of patients (86%) receiving the GM2 vaccine produced antibodies. Patients that produced anti-GM2 antibodies had a significantly longer disease free and overall survival than antibody negative patients. Comparing the two arms of the trial, patients receiving the GM2/BCG vaccine had a 17% improvement in disease-free interval and 9% improvement in survival when compared to the BCG control group, though neither result was statistically significant (Livingston et al., 1993a). Unfortunately, the immune response was only of short duration, mostly IgM and of moderate titer. This suggested that GM2 was recognized as a T-cell independent antigen as a consequence of carbohydrate antigens (Livingston et al., 1989) and also because gangliosides are auto antigens expressed on some normal tissue (Hamilton et al., 1993). Similar approaches with GD2 and 9-0-Acetyl-GD3 vaccines in patients resulted in occasionally low titers and no antibody response against GD3 could be detected (Livingston, 1991).

New potent adjuvants were able to enhance the immune responses against gangliosides in some cases, but especially for auto antigens such as for tumor associated gangliosides a different approach had to be utilized. Based on Landsteiner's classical experiments (Landsteiner and Chase, 1942) with hapten-carrier conjugates, covalent attachment of poorly immunogenic antigens to immunogenic carrier proteins has been successfully used to enhance immune response. For example responsiveness to carbohydrates, other than gangliosides, could be accomplished with conjugation to appropriate carrier proteins. Coupling of bacterial capsular polysaccharides to immunogenic proteins showed a significant increase in immune response and protection (Eskola et al., 1990). Recently, vaccination of ovarian cancer patients with synthetic Thompson Friedenreich tumor antigen conjugated to keyhole limpet hemocyanin elicited humoral IgM and IgG response (MacLean et al., 1992). The important finding common in these studies was the isotype switch from a IgM response of short duration to a long lasting, high affinity IgG response indicating that activation of T-cell dependent pathways against carbohydrates is likely to occur. This approach is now applied to the melanoma tumor antigen GD3 to develop a method to synthesize ganglioside-protein conjugate vaccines and examine the immunogenicity of different GD3-protein conjugates in mice.

SUMMARY OF THE INVENTION

This invention provides a vaccine for stimulating or enhancing in a subject to which the vaccine is administered, production of an antibody which recognizes a ganglioside, comprising an amount of ganglioside or oligosaccharide portion thereof conjugated to an immunogenic protein effective to stimulate or enhance antibody production in the subject, an effective amount of adjuvant and a pharmaceutically acceptable vehicle.

This invention also provides a method for stimulating or enhancing in a subject production of antibodies which recognize a ganglioside comprising administering to the subject an effective dose of a vaccine for stimulating or enhancing in a subject to which the vaccine is administered, production of an antibody which recognizes a ganglioside, comprising an amount of ganglioside or oligosaccharide portion thereof conjugated to an immunogenic protein effective to stimulate or enhance antibody production in the subject, an effective amount of adjuvant and a pharmaceutically acceptable vehicle.

BRIEF DESCRIPTION OF TH FIGURES

Figure 1B:
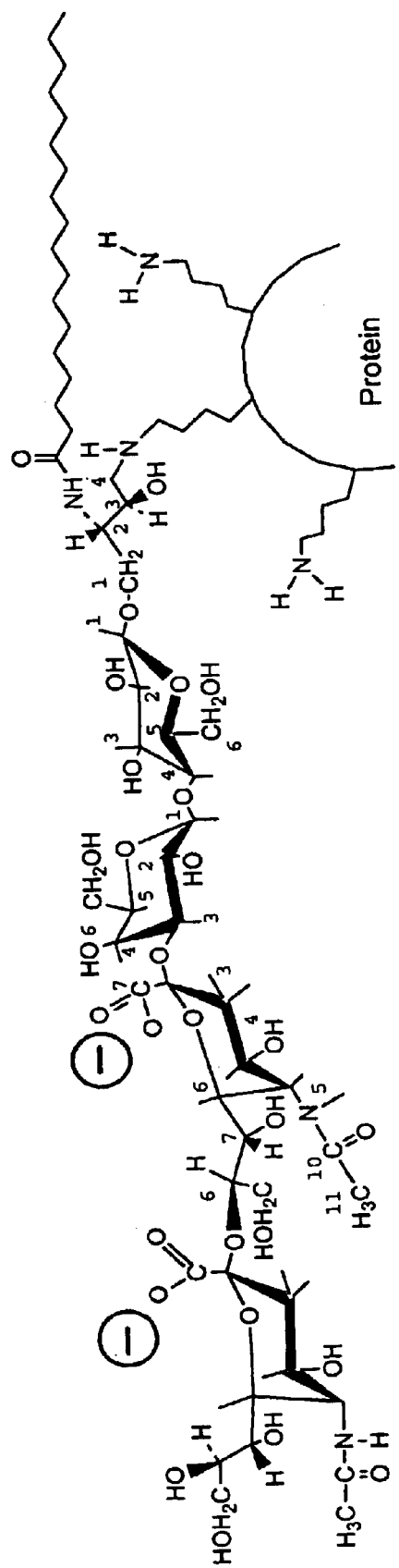

FIGS. 1A and 1B: The Synthesis of GD3 protein conjugates after ozone cleavage and reductive amination. Insert represents HPTLC of GD3 before (lane A) and after (lane B) the cleavage.

Figure 2B:
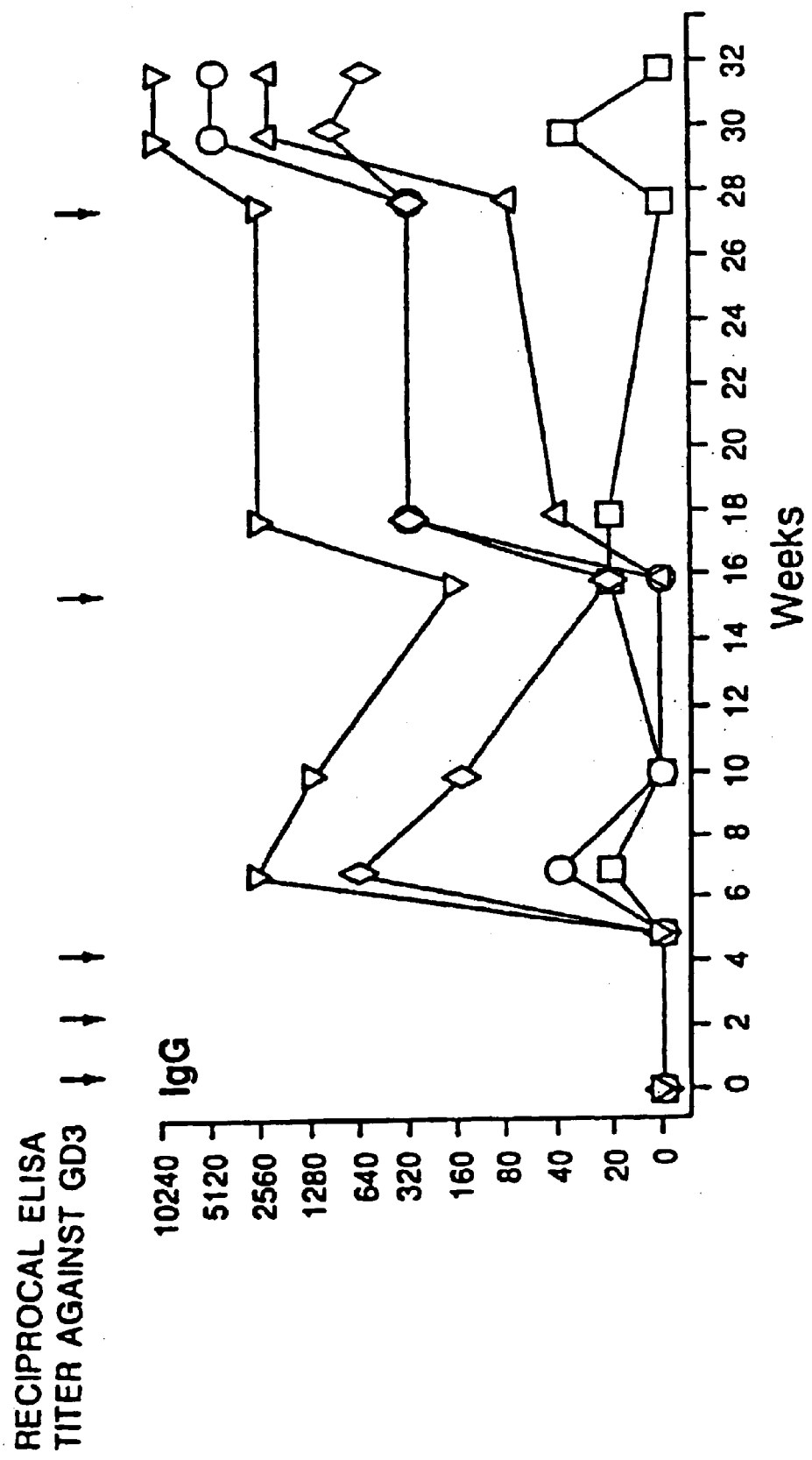

FIGS. 2A and 2B Time course of GD3-KLH antisera IgM (FIG. 2A) and IgG (FIG. 2B) antibodies. Each symbol on the figure represents a mouse.

Figure 3A:
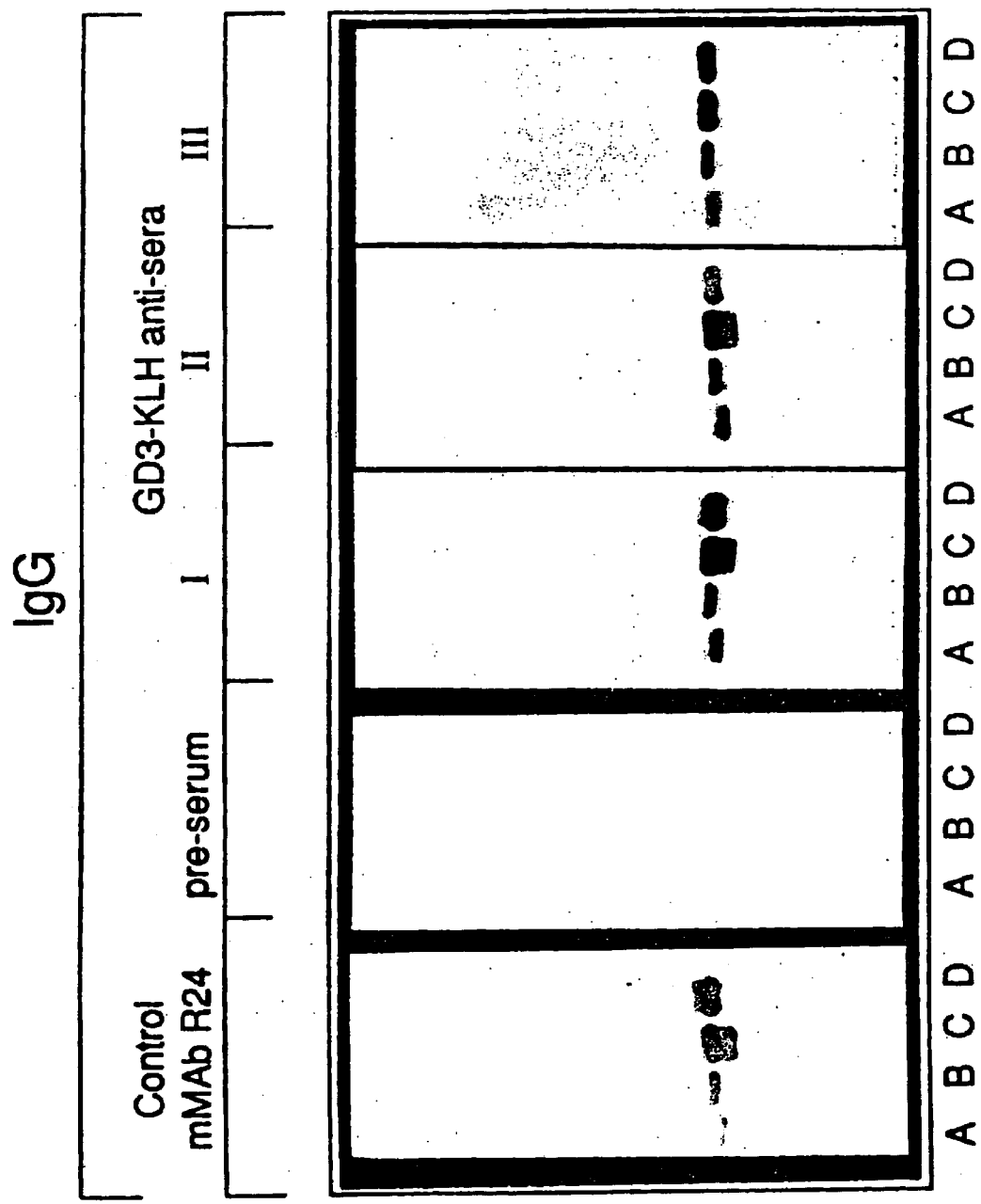
Figure 3B:
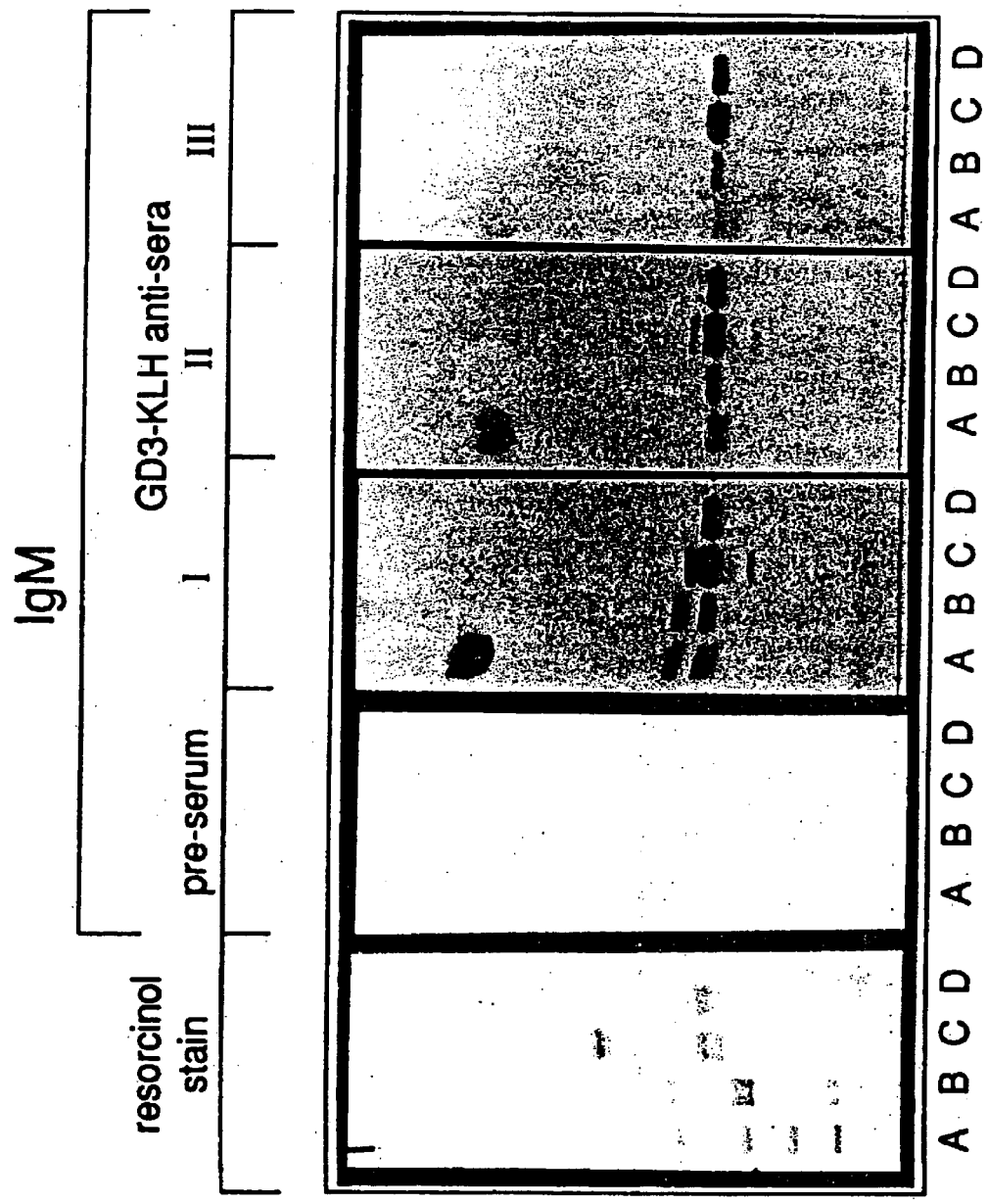

FIGS. 3A and 3B Immune thin layer chromatography of three mouse antisera after vaccination with GD3-KLH. Reactivities of IgG (FIG. 3A) and IgM (FIG. 3B) antibodies were tested on A, human brain gangliosides, B neuroblastoma gangliosides, C, melanoma ganglioside and D, GD3 antigen.

Figure 4:
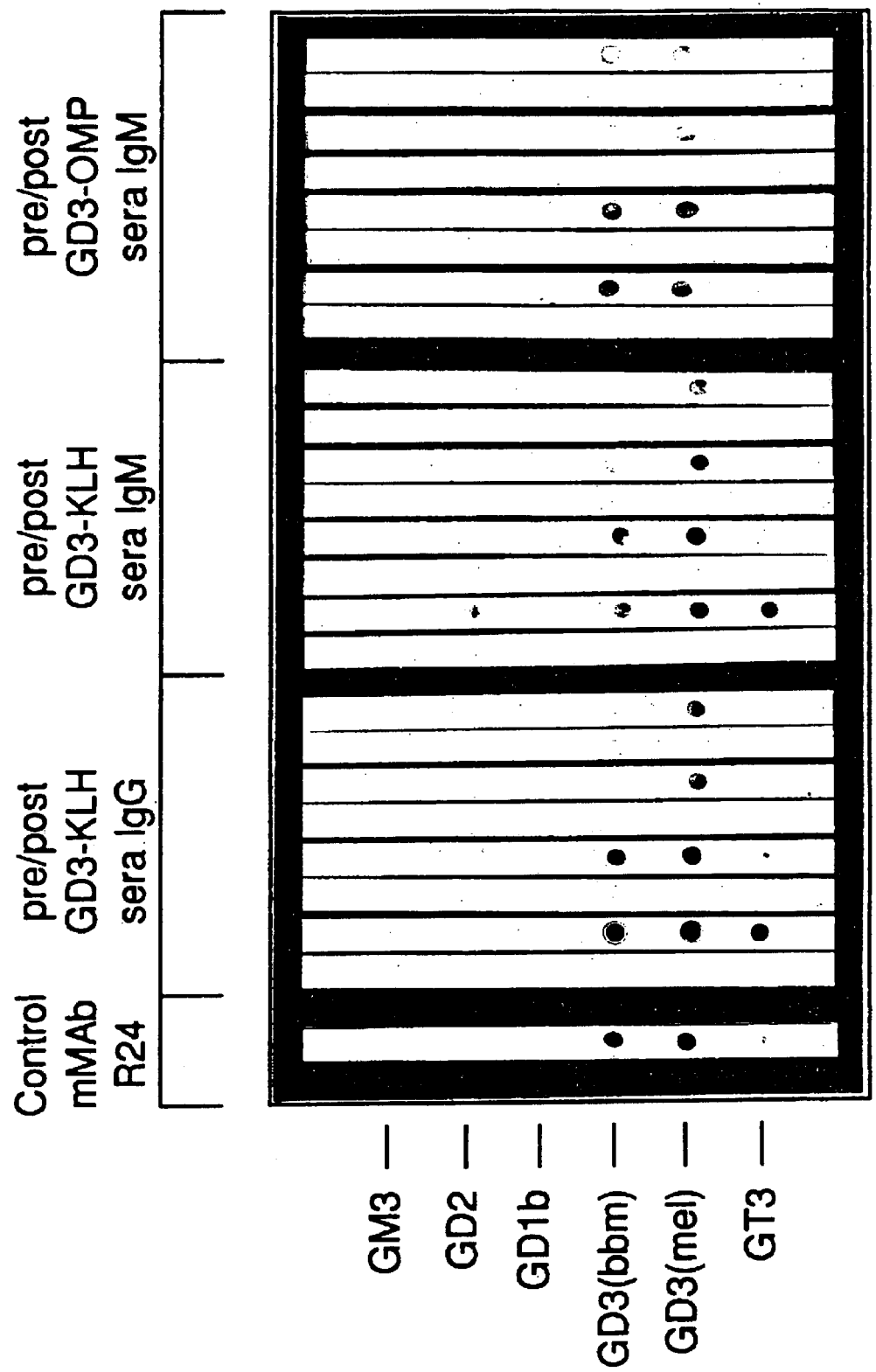

FIG. 4 Immunoblot of four different mice to show the specificity of the immune response. Pure ganglioside are dot-blotted and incubated with sera from mice.

Figure 5:
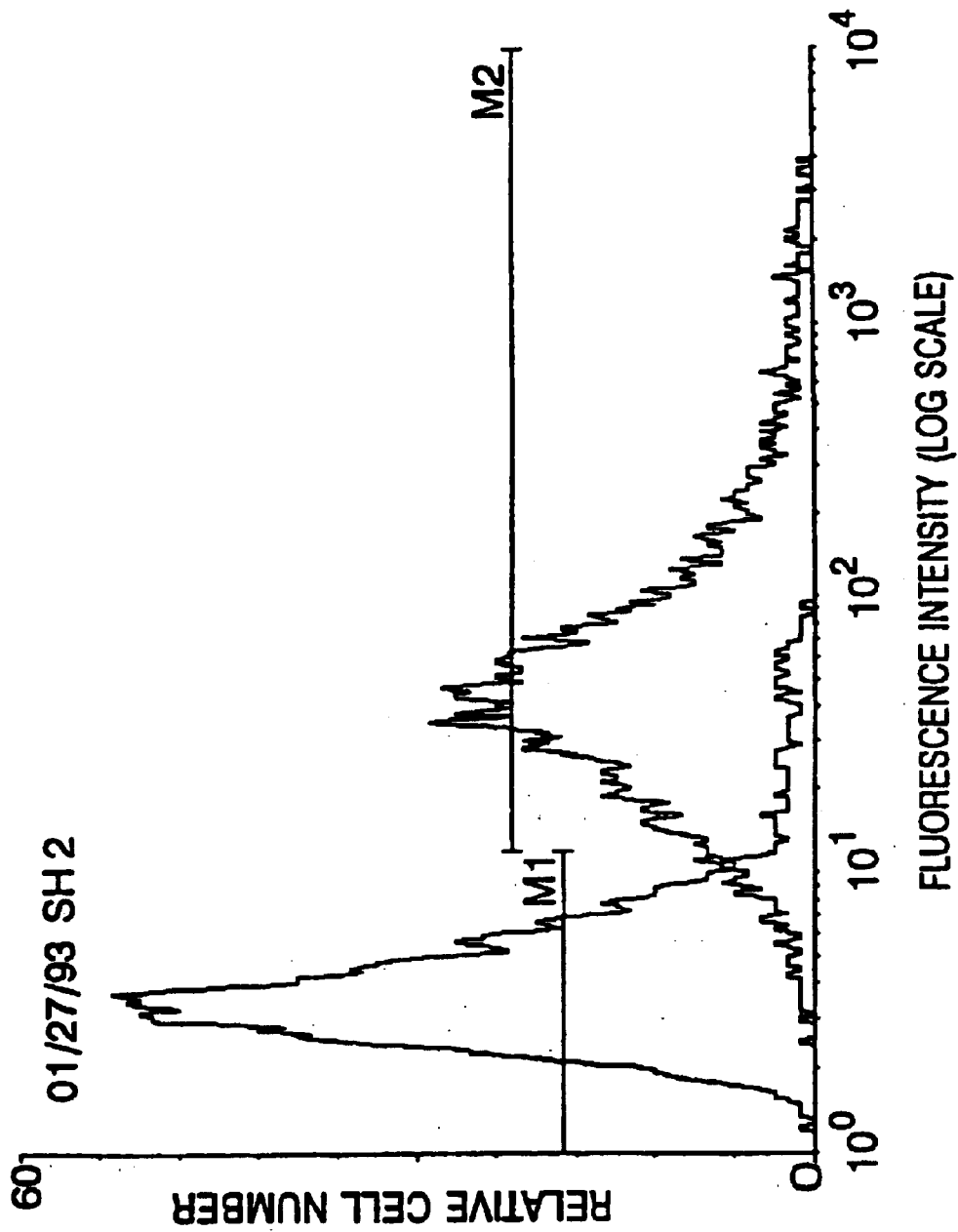

FIG. 5 Representative FACS analysis of mouse serum reactivity prior to (peak at 3) and after (peak at 50) immunization with $G_{D3}$-KLH and QS-21 tested on melanoma cell line SK-MEL-28

Figure 6A:
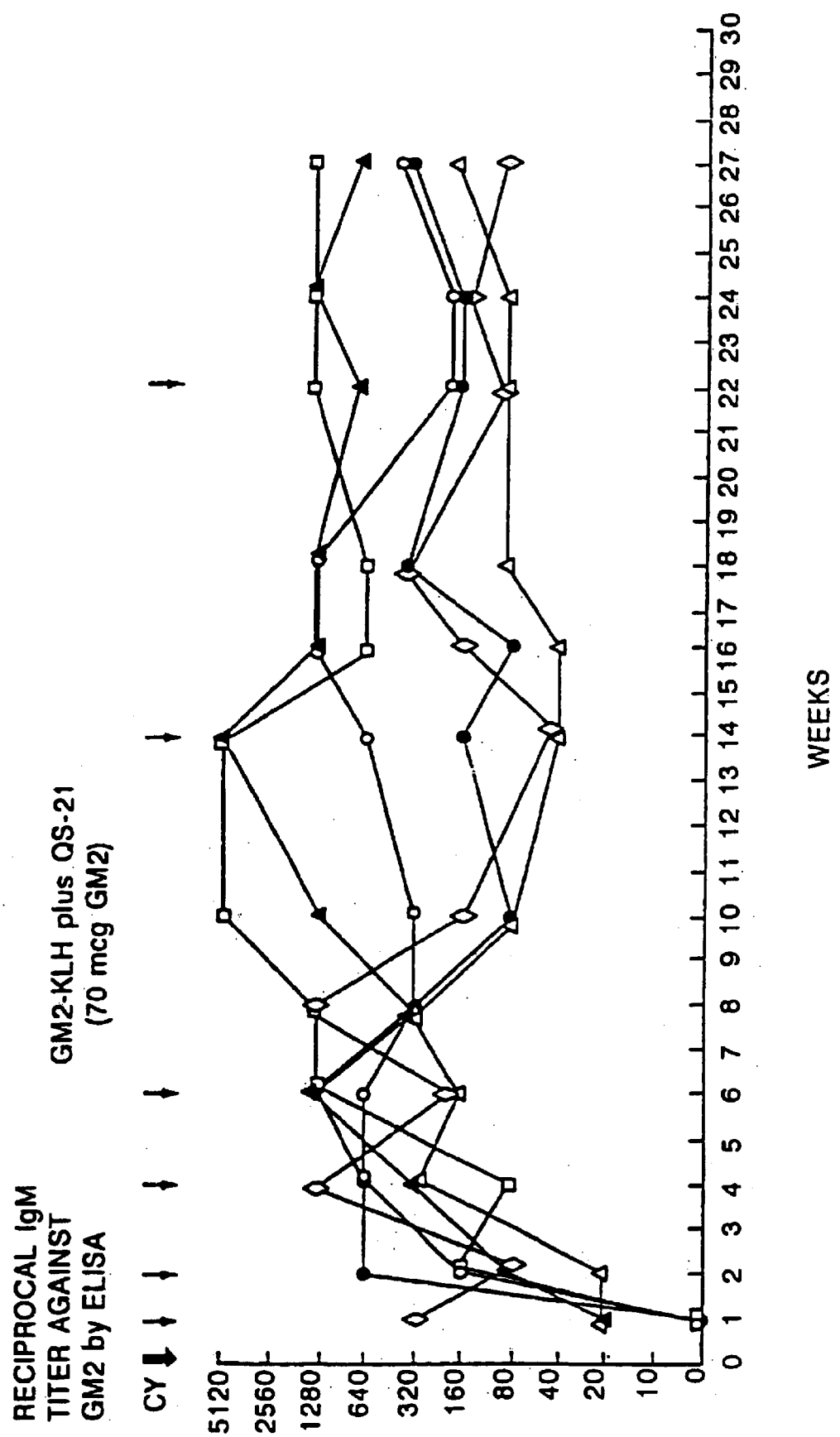

FIGS. 6A and 6B Time course of GM2-KLH antisera IgM (FIG. 6A) and IgG (FIG. 6B) antibodies. Each symbol on the figure represents a patient.

Figure 7:
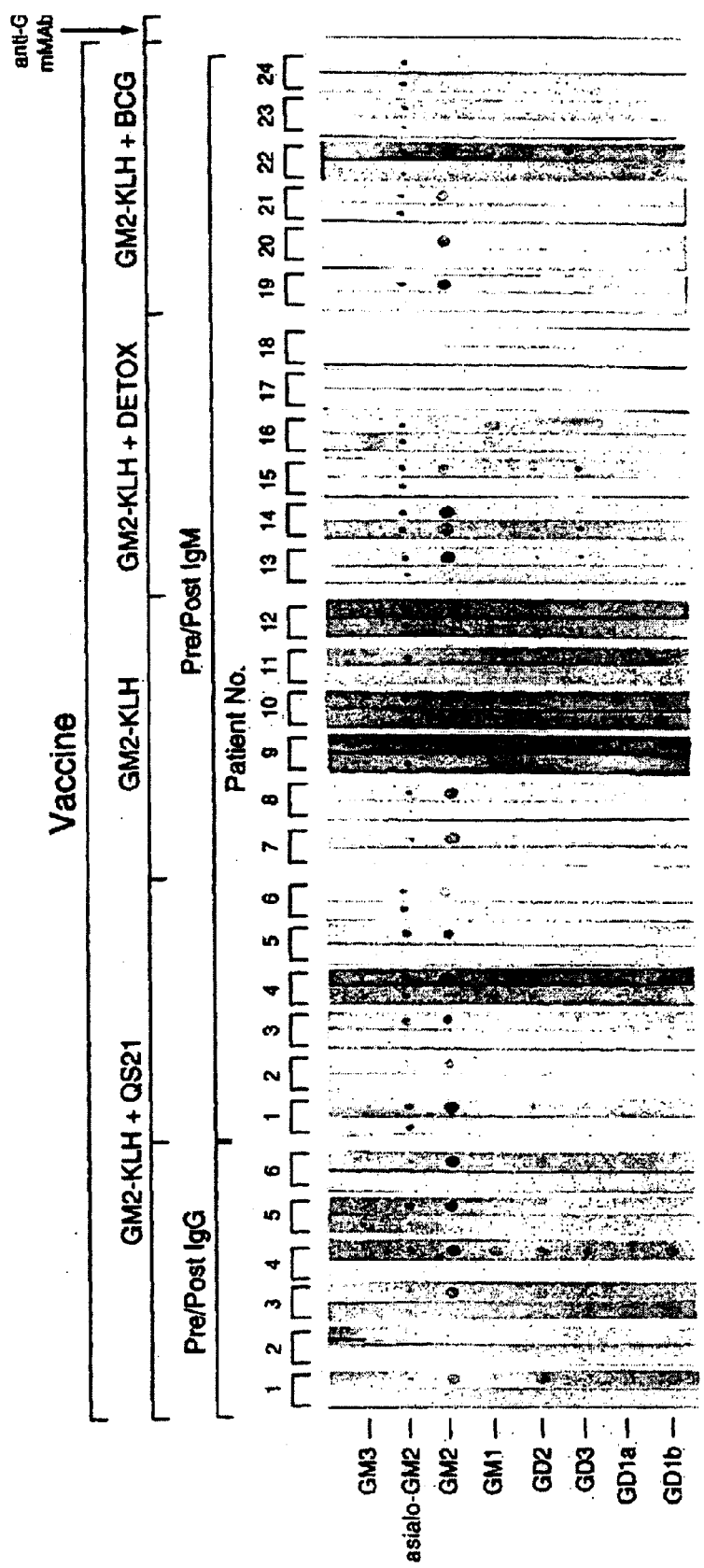

FIG. 7 Detection of GM2 antibody in sera from patients vaccinated with GM2 conjugate vaccine plus adjuvant by dot blot immune staining.

Ganglioside standards were spotted on nitrocellulose strips (indicated on the vertical axis) and allowed to react with prevaccination and peak titer postvaccination sera from individual patients and peroxidase-labeled goat anti-human IgM or IgG antibody. Strips are graded on a scale from 0 to 3+. MAb 696 was used as positive control for GM2.

Figure 8A:
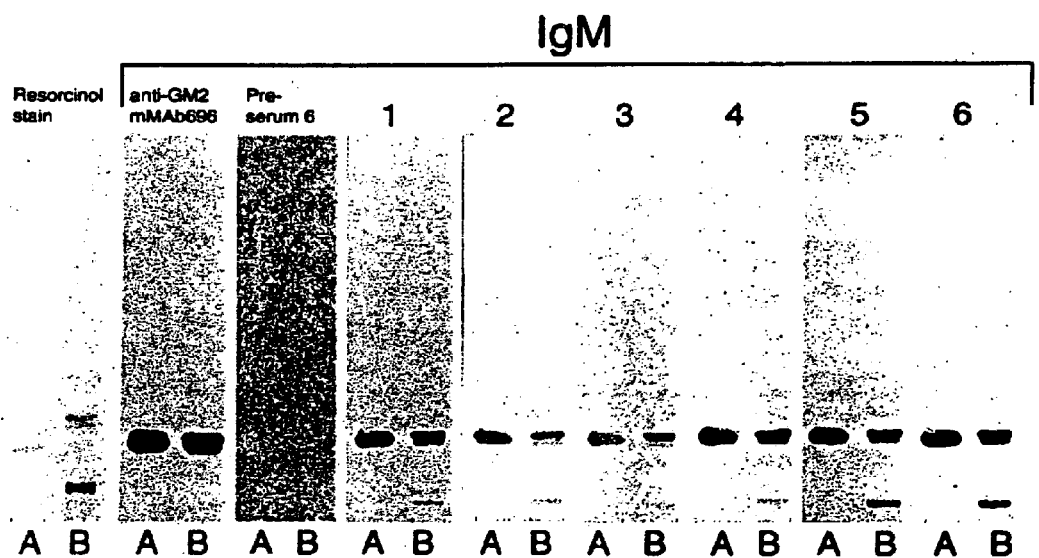
Figure 8B:
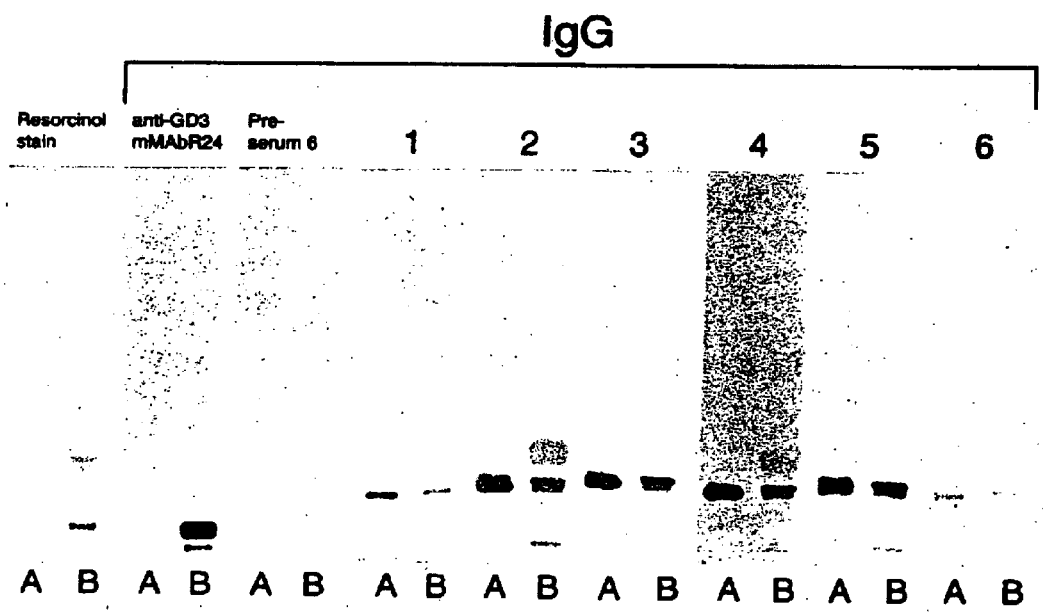

FIGS. 8A and 8B: Specificity of peak titer sera from patients immunized GM2-KLH+QS-21 vaccine determined by immune thin layer chromatography as described previously (3, Reference of the Third Series of Experiments). GM2 (A) and melanoma tissue ganglioside extract (B) were applied to TLC plates, incubated with sera from individual patients and stained with peroxidase-labeled goat anti-human IgM or IgG antibody. MAb 696 was used as positive control for GM2 and resorcinol stain for gangliosides.

Figure 8C:
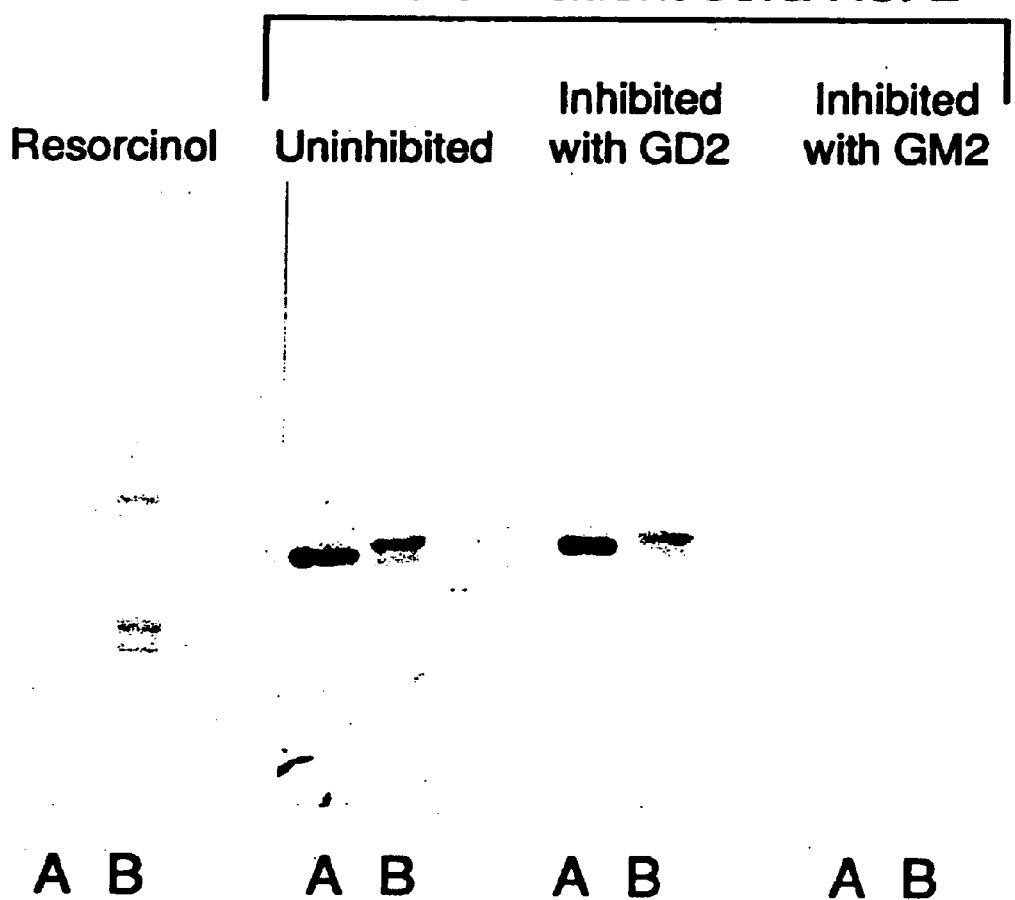

FIG. 8C Inhibition of IgG reactivity of patient serum against GM2 and GD2. GM2 (A) and melanoma tissue ganglioside extract (B) were applied to HPTLC plates, incubated with serum from patient No. 2 and stained with peroxidase-labeled goat anti-human IgG antibody. 3 ml Patient serum at a dilution of 1:50 was preincubated with either 150 $\mu$g GM2 or 150 $\mu$g GD2 prior to immune staining.

Figure 9A:
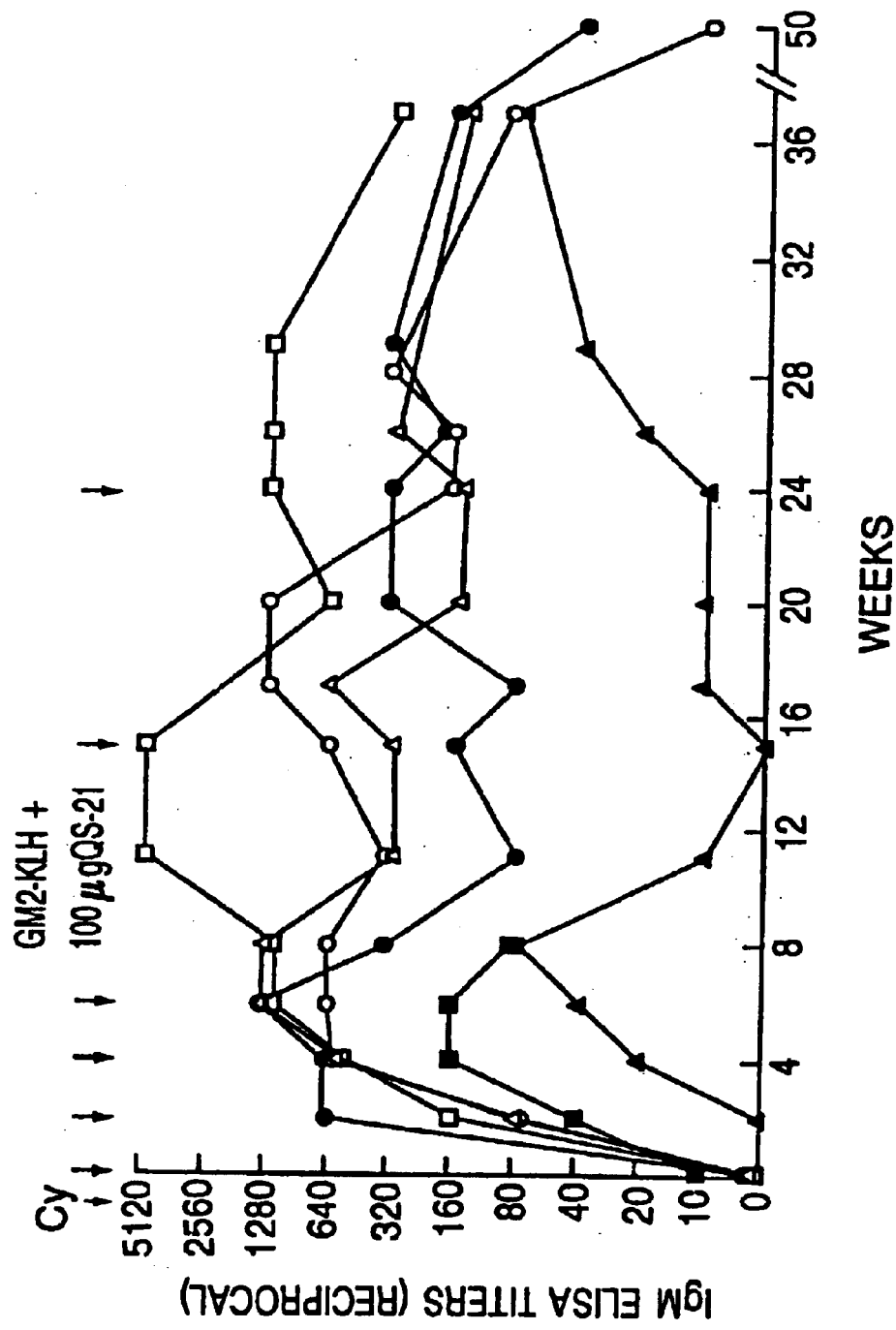
Figure 9B:
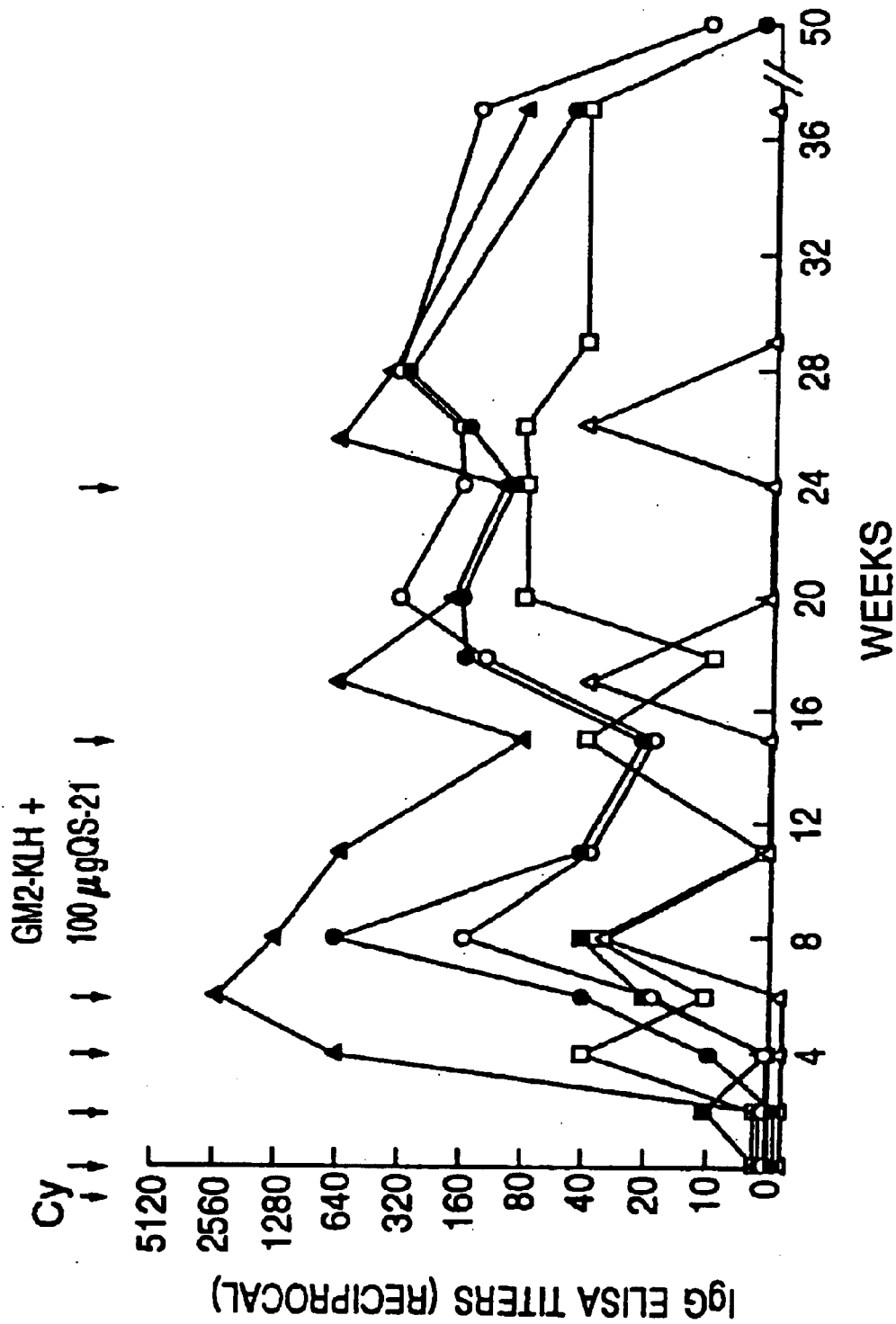
Figure 9C:
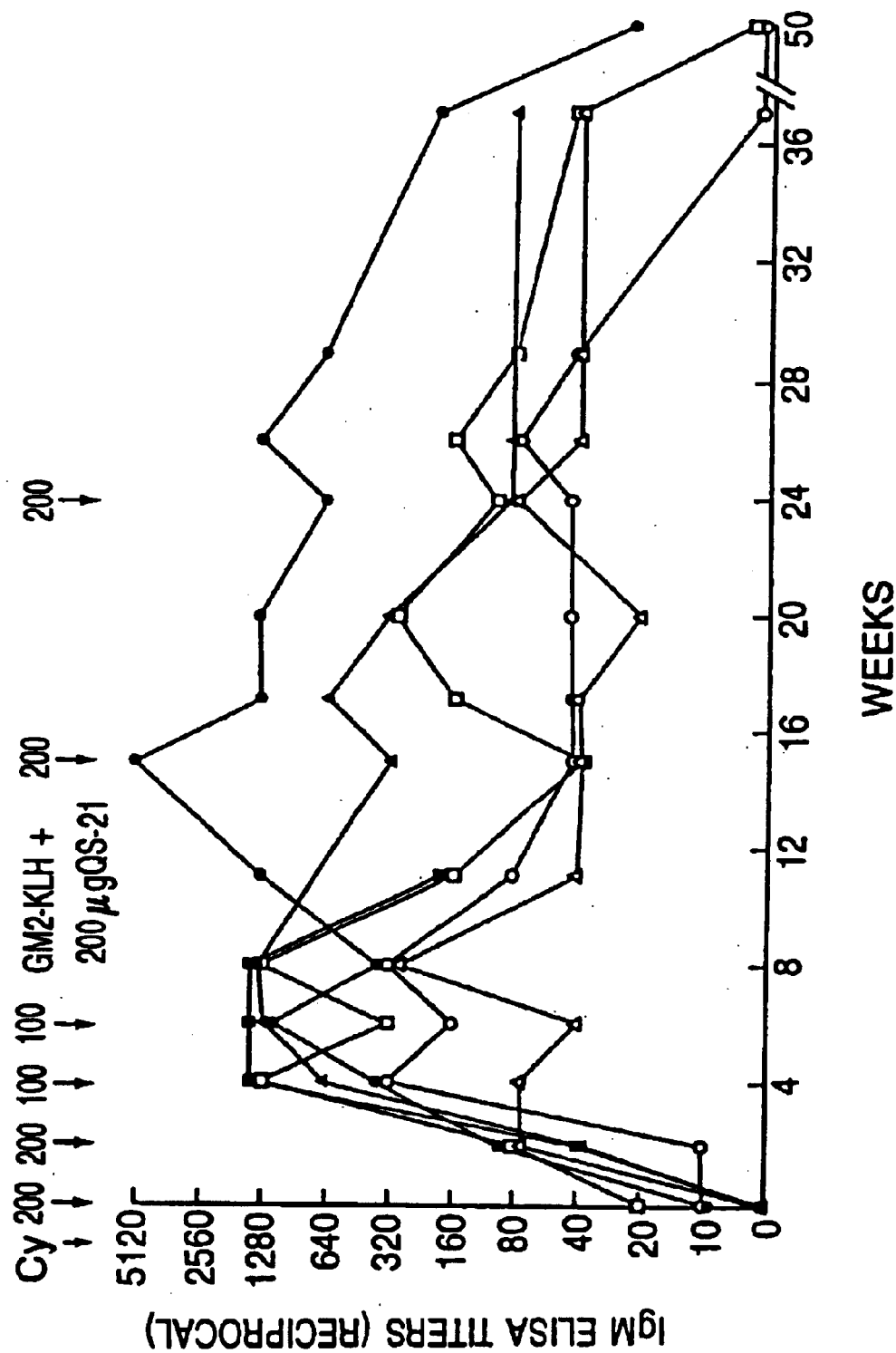
Figure 9D:
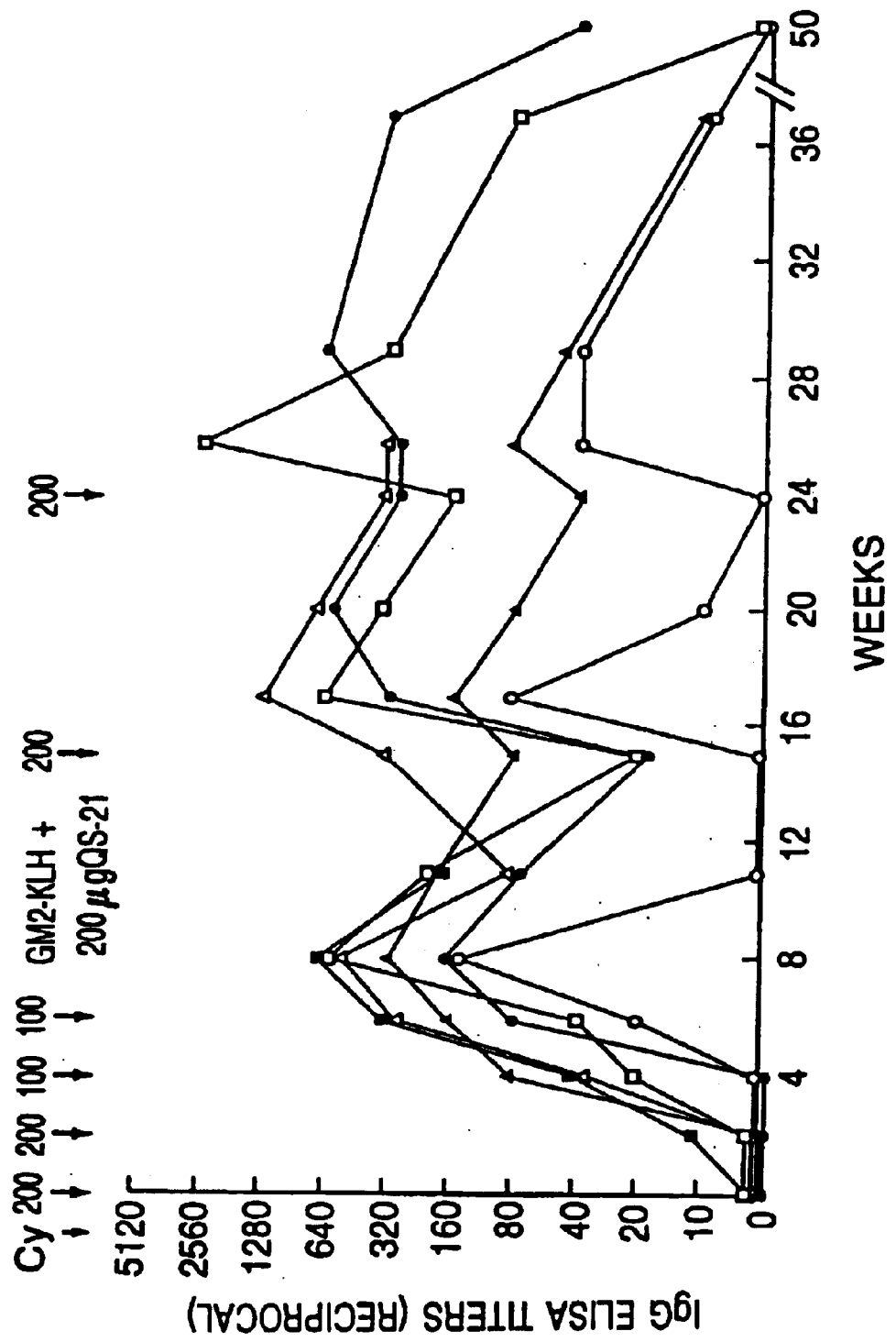

FIGS. 9A, 9B, 9C, and 9D IgM and IgG antibody responses in melanoma patients after immunization with GM2-KLH plus QS-21 vaccines. Sequential results for six patients receiving the 100 ug QS-21 dose are shown in FIGS. 9A and 9B and for six patients receiving the 200 ug dose in FIGS. 9C and 9D. Note that one patient in each group received only four vaccinations and was taken off study due to disease progression. Arrows indicate the time of cyclophosphamide (Cy) and GM2-KLH plus QS-21 vaccine injections.

Figure 10A:
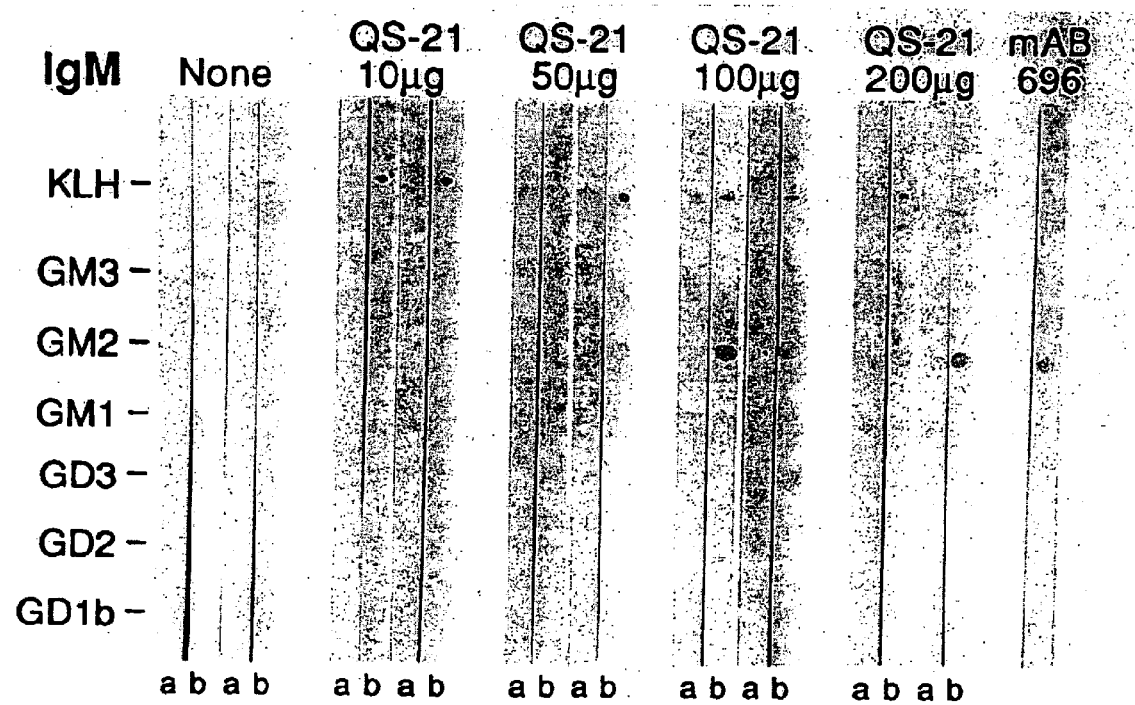
Figure 10B:
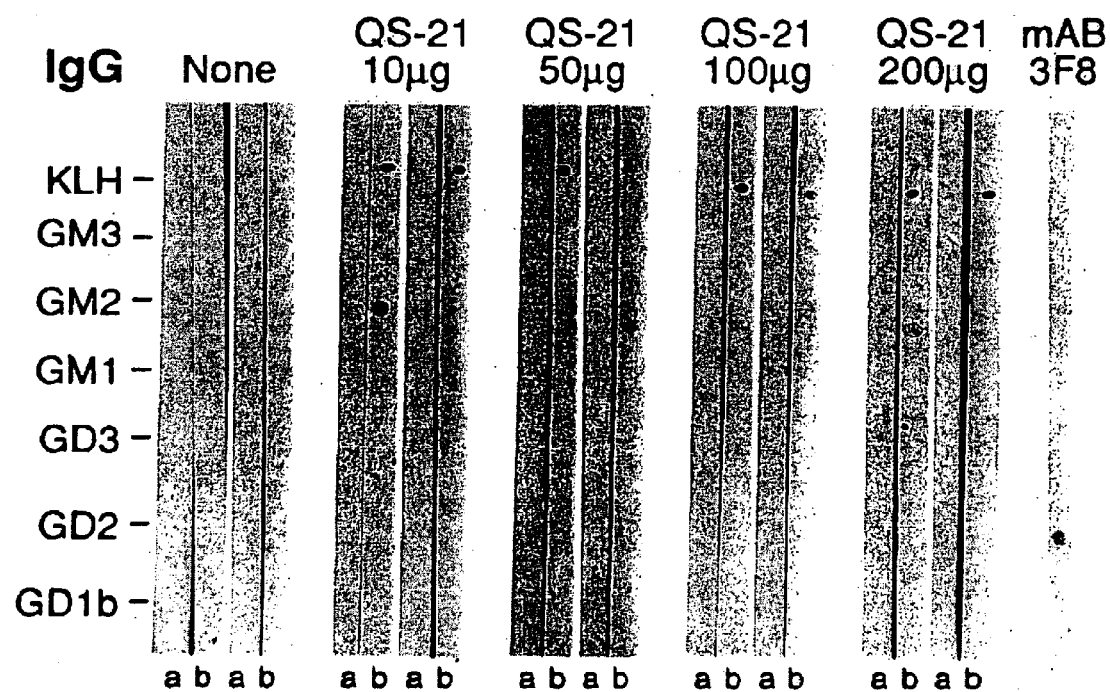

FIGS. 10A and 10B Detection of GM2 antibody by dot blot immune staining with sera from ten patients vaccinated with GM2-KLH. Ganglioside standards were applied to nitrocellulose strips (as indicated on the left) and incubated first with sera and then, after washing, with peroxidase labelled goat anti-human IgM (FIG. 10A) or (FIG. 10B) antibody. Results with sera from two patients from each of the five groups receiving different QS-21 doses (as indicated at the top) are shown. Pre- (a) and post-immunization (b) sera are shown for each patient. Murine monoclonal antibodies 696 and 3F8 are IgM and IgG antibodies (respectively) against GM2 and GD2. IgM antibody against GM1 was detected in sera from most patients before and after vaccination. IgM and IgG antibody against GM2 was not detected before vaccination in any of these patients. After vaccination IgM and IgG antibodies were detected against GM2 in sera from all patients. Reactions were graded 0, 1+, 2+ or 3+. An example reaction grading for this assay is: Patient 1 (100 ug QS-21) IgM (pre/post vaccination): KLH 1+/2+ Gm3 0/0 Gm2 0/3+ Gm1 1+/1+ GD2 0/0 GD2 0/1+, GD1b 0/0.

Figure 11A:
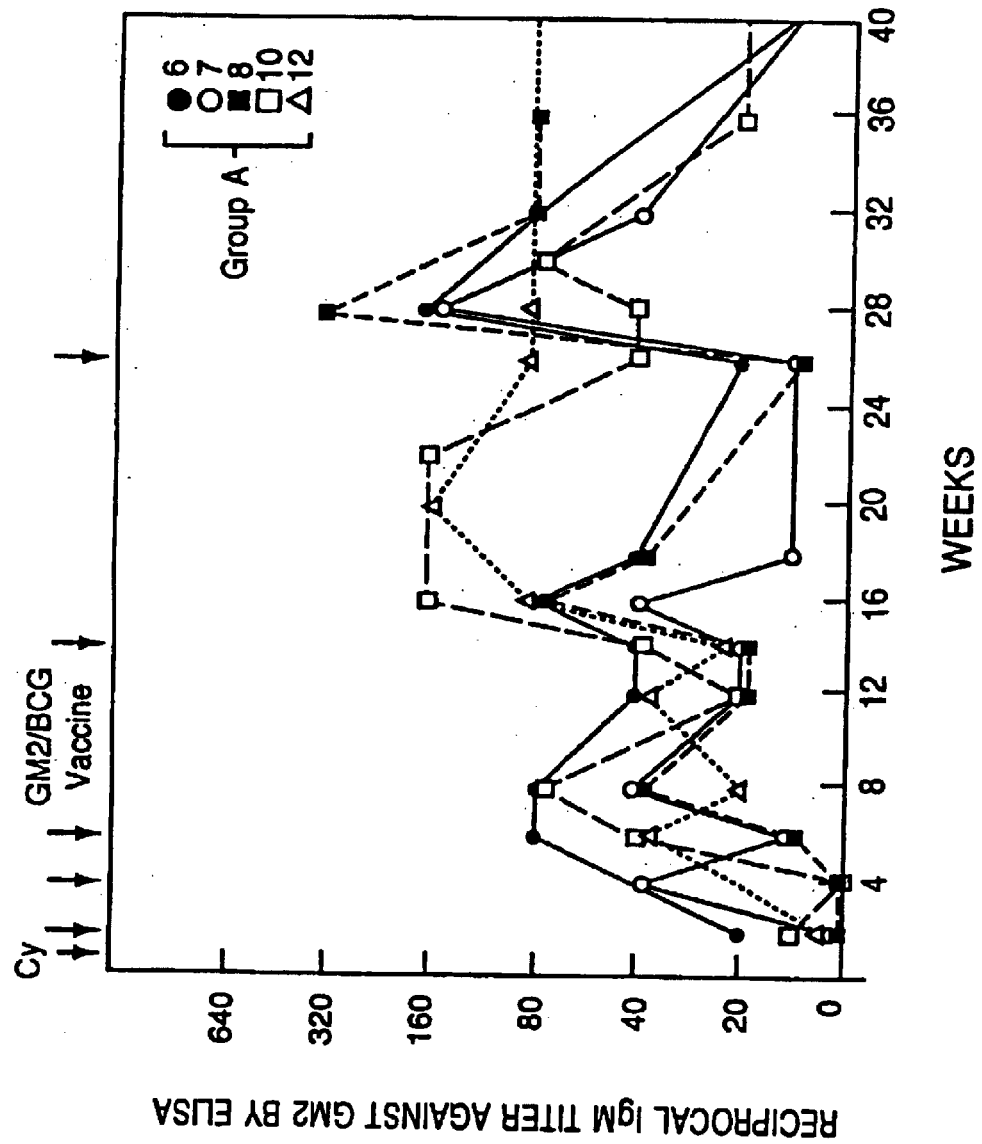
Figure 11B:
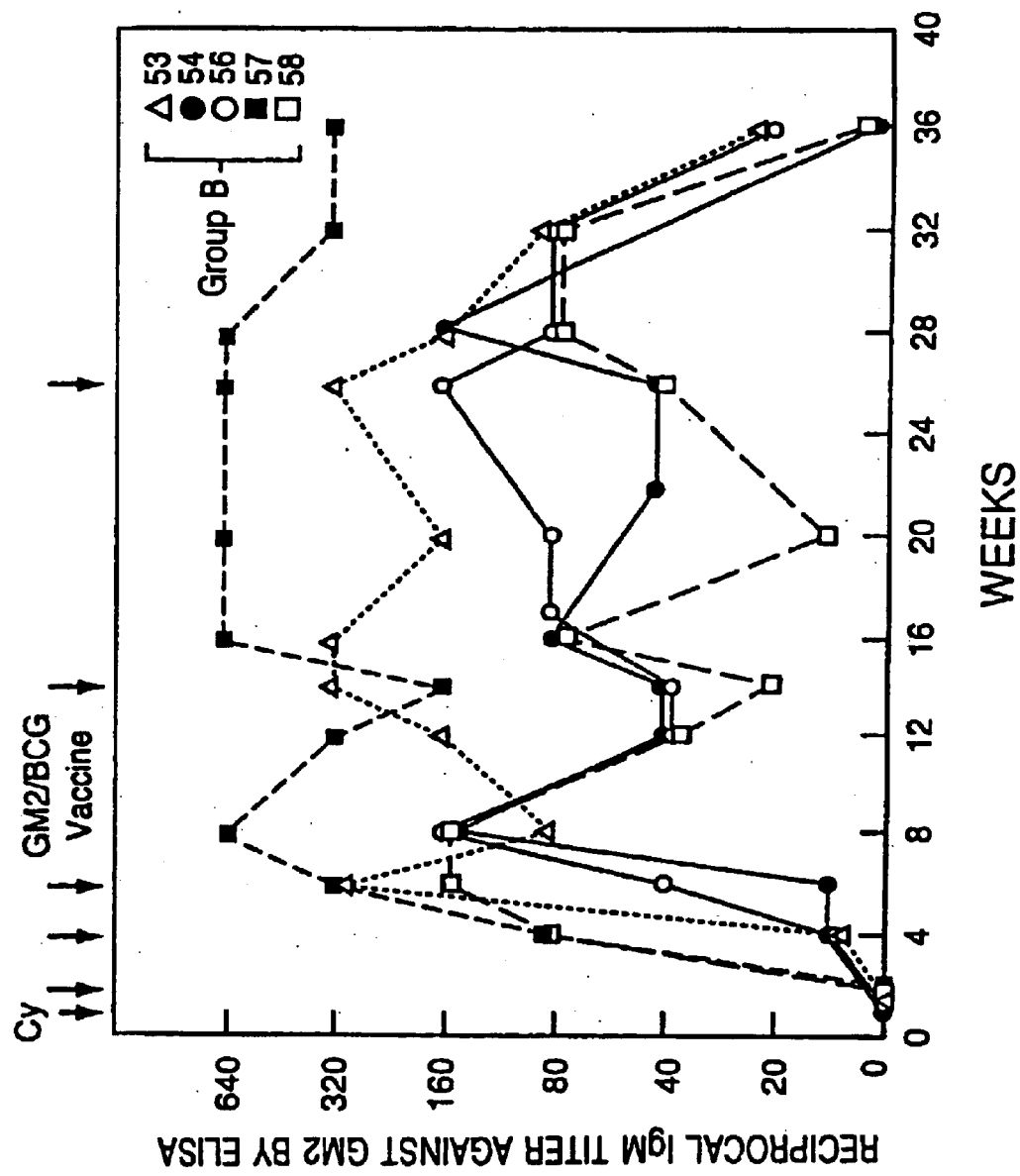

FIGS. 11A and 11B IgM antibody responses in melanoma patients after immunization with the GM2/BCG vaccine. Sequential results for five patients treated during the initial four months of the protocol (group A) and five patients treated during the final four months of the protocol (group B) ar shown. Arrows indicate time of cyclophosphamide (Cy) and GM2/BCG vaccine injections.

Figure 12:
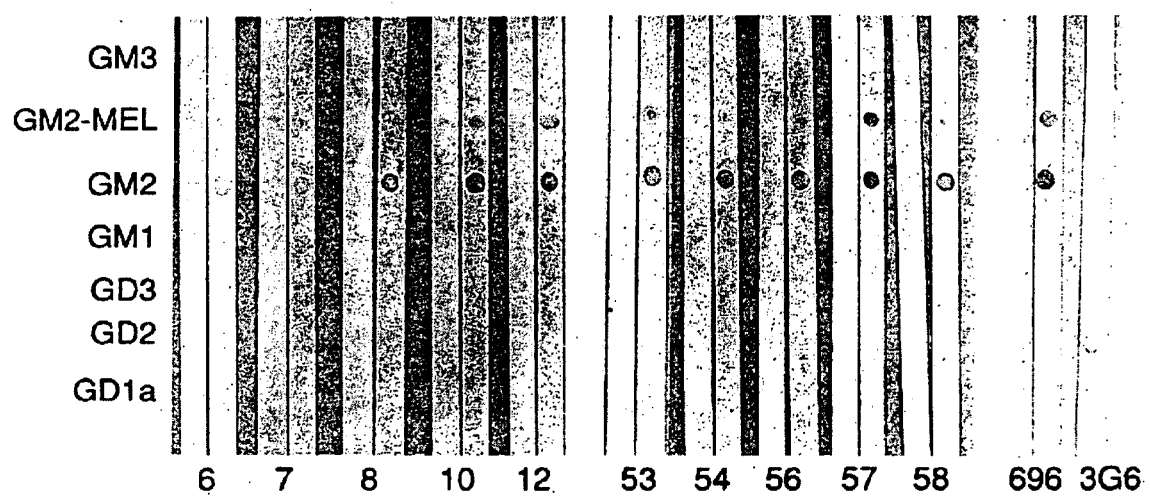

FIG. 12 Detection of GM2 antibody by dot blot immune staining in sera from ten GM2/BCG vaccinated melanoma patients. Ganglioside standards were applied to nitrocellulose strips (as indicated on the left) and incubated first with sera and then after washing incubated with peroxidase labelled goat anti-human IgM antibody. GM2-MEL indicates purified GM2 extracted from melanoma biopsy samples, all other gangliosides including GM2 were derived from bovine brain. Patient numbers (6 to 58) are indicated, and pre- (a) and post-(b) immunization sera are shown for each patient. 696 and 3G6 are IgM murine monoclonal antibodies against GM2 and GD2 respectively. GM2 antibody was detected in post vaccination sera from these 10 patients. GM1 antibody was seen in pre- and post-treatment sera from patient 53 and in the post treatment serum from patient 57. Reactions were graded 0 1+, 2+, or 3+. Examples of reaction gradients are as follows: patient 8: GM2 3+, GM2-MEL 2+; patient 54: GM2 3+, GM2-MEL 1+ and patient 57: GM2 3+, GM2-MEL 3+. The lower reactivity against GM2-MEL compared to GM2 seen with post vaccine sera and murine monoclonal antibody 696 reflects a lower quantity of GM2-MEL ganglioside applied to the strips.

Figure 13:
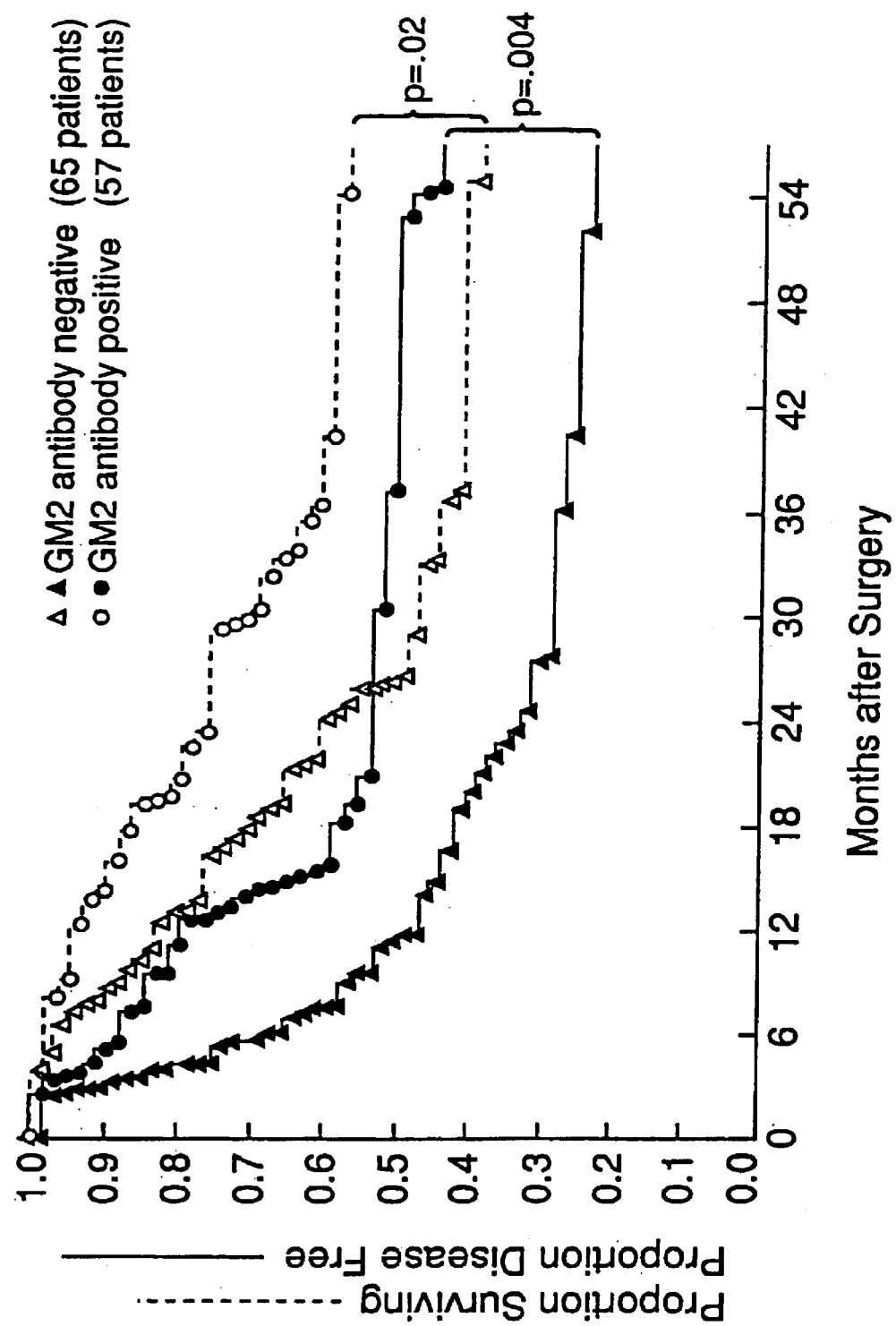

FIG. 13 Kaplan-Meier plots of disease-free and overall survival of patients with post vaccination GM2 antibody production. Patients were categorized as positive if GM2 reactivity was a) 2+ or 3+ by dot blot with an ELISA titer $\geq 1/20$ or b) 1+ by dot blot with an ELISA titer $\geq 1/80$.

Figure 14:
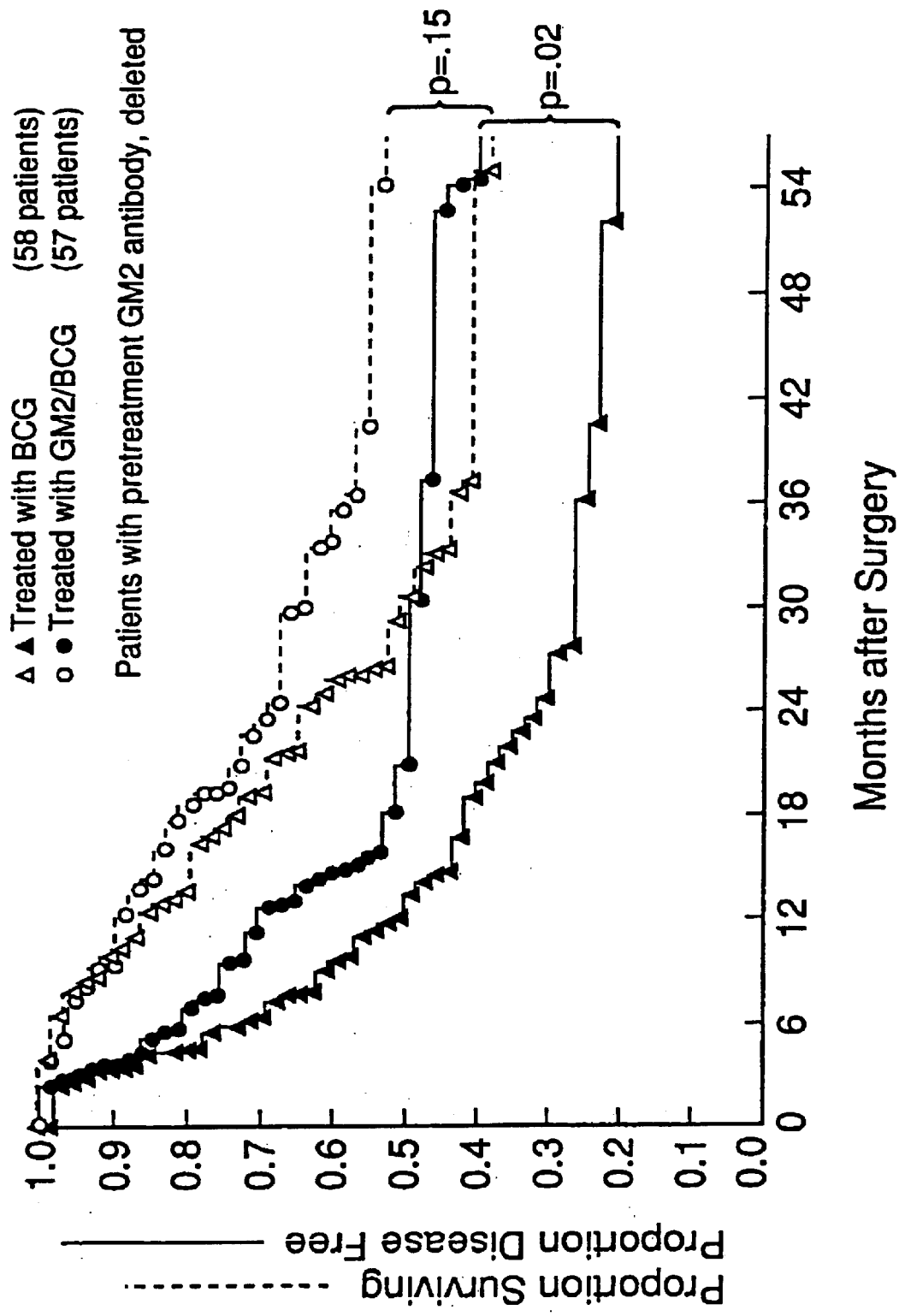

FIG. 14 Kaplan-Meier plots of disease-free and overall survival of 59 patients randomized to receive BCG and 57 patients randomized to receive GM2/BCG, excluding six patients who produced GM2 antibody prior to immunization (five in the BCG arm and one in the GM2/BCG arm).

Figure 15:
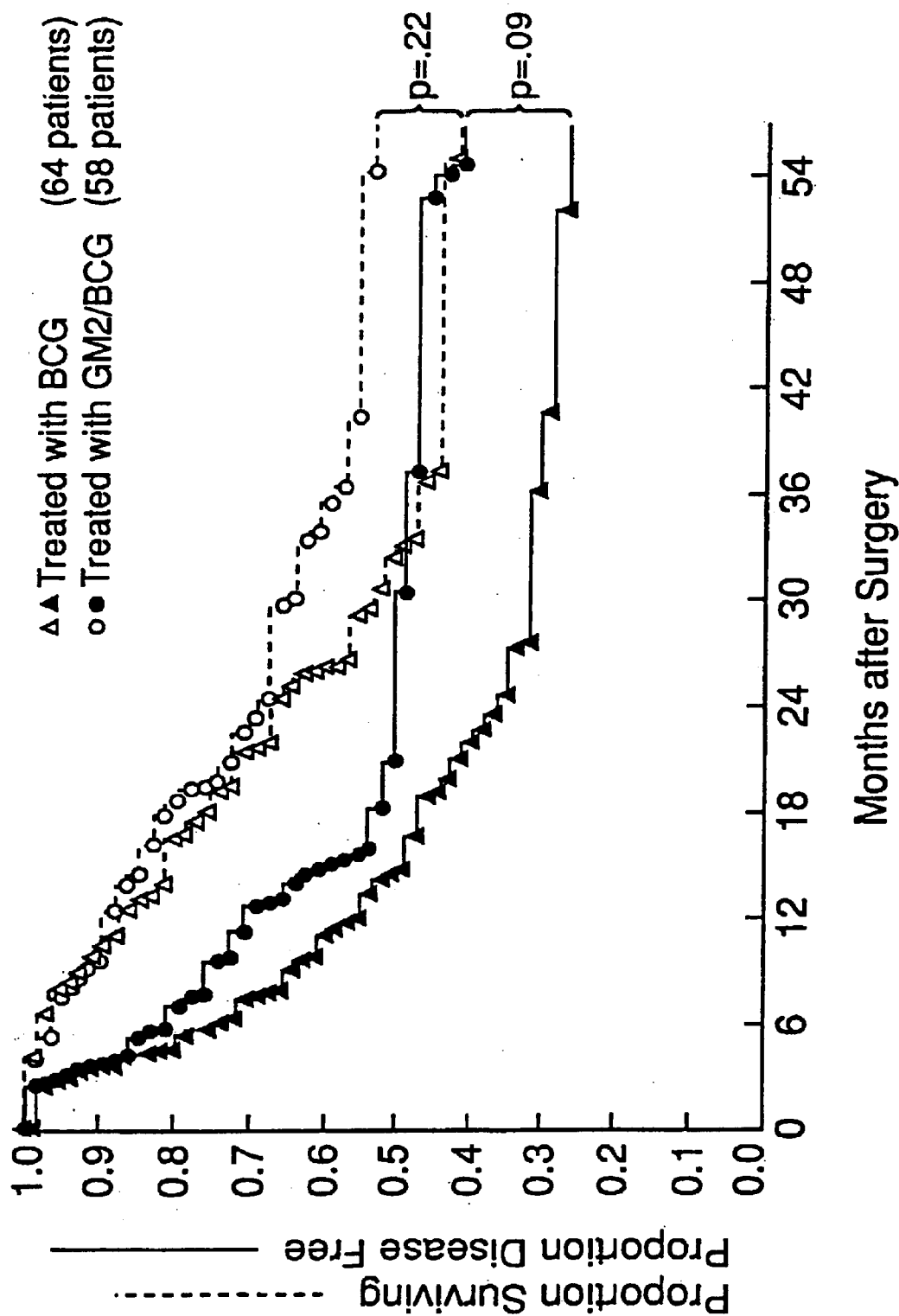

FIG. 15 Kaplan-Meier plots of disease-free and overall survival of 64 patients randomized to receive BCG and 58 patients randomized to receive GM2/BCG.

FIG. 16 Kaplan-Meier plots of disease-free survival of 59 GM2 antibody-negative patients randomized to receive BCG ($\Delta$ or $\blacktriangle$) compared to 57 GM2 antibody-negative patients randomized to receive GM2/BCG ($\square$ or $\blacksquare$). Patients are stratified into two groups, patients with a single positive lymph node ($\Delta$ or $\square$) and patients with two or more positive lymph nodes ($\blacktriangle$ or $\blacksquare$).

DETAILED DESCRIPTION OF TH INVENTION

Throughout this application, various references ar referred to within parentheses. Disclosures of these publications in their entireties are hereby incorporated by reference into this application to more fully describe the state of the art to which this invention pertains. Full bibliographic citation for these references may be found at the end of this application, preceding the claims.

This invention provides a vaccine for stimulating or enhancing in a subject to which the vaccine is administered, production of an antibody which recognizes a ganglioside, comprising an amount of ganglioside or oligosaccharide portion thereof conjugated to an immunogenic protein effective to stimulate or enhance antibody production in the subject, an effective amount of adjuvant and a pharmaceutically acceptable vehicle.

The oligosaccharide portion of a ganglioside may be derived by cleaving a ganglioside or it may be synthesized directly. As used herein, an immunogenic protein is a protein that, when conjugated to the ganglioside or oligosaccharide portion thereof, stimulates or enhances antibody production in the subject.

In an embodiment of this invention, the subject is a human.

This invention also provides the above-described vaccine wherein the ganglioside or oligosaccharide portion thereof is conjugated to Keyhole Limpet Hemocyanin or a derivative of Keyhole Limpet Hemocyanin.

Keyhole Limpet Hemocyanin is a well-known protein. A derivative of Keyhole Limpet Hemocyanin may be generated by direct linkage of at least one immunological adjuvant such as monophospholipid A or non-ionic block copolymers or cytokine with Keyhole Limpet Hemocyanin. Cytokines are well known to an ordinary skilled practitioner. An example of cytokine is interleukin 2. There are other known interleukins in the art which may be linked to Keyhole Limpet Hemocyanin, forming a derivative of Keyhole Limpet Hemocyanin.

In an embodiment of the above-described vaccine the adjuvant is QS-21.

There are other known adjuvants which may be applicable to this invention. There may be classes of QS-21 or QS-21 like chemicals which may be similarly used in accordance with this invention.

This invention further provides the above-described vaccine wherein the ganglioside is selected from the group consisting of GM2, GM3, GD2, GD3, GD3 lactone, O-Acetyl GD3 and GT3.

In one of the preferred embodiments of this invention, the ganglioside is GM2. In another embodiment, the ganglioside is. GD3. In another embodiment, the ganglioside is GD2.

Different effective amounts of the conjugated ganglioside or oligosaccharide portion thereof may be used according to this invention. A person of ordinary skill in the art can perform simple titration experiments to determine what the effective amount is required for effective immunization; An example of such titration experiment is to inject different amounts of the conjugated ganglioside or conjugated oligosaccharide portion thereof to the subject and then examine the immune response.

In an embodiment, the effective amount of conjugated ganglioside or conjugated oligosaccharide portion thereof is an amount between about 1 $\mu$g and about 200 $\mu$g.

In another embodiment, the effective amount of conjugated ganglioside or conjugated oligosaccharide portion thereof is an amount between about 50 $\mu$g and about 90 $\mu$g. In an embodiment, the effective amount of conjugated ganglioside or conjugated oligosaccharide portion thereof is about 70 $\mu$g.

In another embodiment, the effective amount of conjugated ganglioside or conjugated oligosaccharide portion thereof is between about 1 $\mu$g and about 10 $\mu$g. In a more specific embodiment, the effective amount of conjugated ganglioside or conjugated oligosaccharide portion thereof is between about 7 $\mu$g and about 10 $\mu$g. In an embodiment, the effective amount of conjugated ganglioside or conjugated oligosaccharide portion thereof is about 7 $\mu$g.

In addition, the effective amount of the adjuvant may also be similarly determined i.e. administering different amount of the adjuvant with the conjugates and examining the immune response so as to determine which amount is effective. When using QS-21 as adjuvant, the effective amount of QS-21 may also be similarly determined.

In a preferred embodiment, the effective amount of QS-21 is an amount between about 10 $\mu$g and about 200 $\mu$g. In an embodiment, the effective amount of QS-21 is about 100 $\mu$g. In another embodiment, the effective amount of QS-21 is about 200 $\mu$g.

This invention further provides a vaccine for stimulating or enhancing in a subject to which the vaccine is administered, production of an antibody which recognizes a ganglioside, comprising an amount of ganglioside or oligosaccharide portion thereof conjugated to an immunogenic protein effective to stimulate or enhance antibody production in the subject, an effective amount of adjuvant and a pharmaceutically acceptable vehicle, wherein the subject is afflicted with cancer and the antibody produced in the subject upon administration of the vaccine effectively treats the cancer.

This invention also provides a vaccine for stimulating or enhancing in a subject to which the vaccine is administered, production of an antibody which recognizes a ganglioside, comprising an amount of ganglioside or oligosaccharide portion thereof conjugated to an immunogenic protein effective to stimulate or enhance antibody production in the subject, an effective amount of adjuvant and a pharmaceutically acceptable vehicle, wherein the subject is susceptible to cancer and the antibody produced in the subject upon administration of the vaccine effectively prevents the cancer.

This invention further provides a vaccine for cancers, wherein cells of the cancer have gangliosides on their surface.

This invention also provides a vaccine for cancers, wherein gangliosides are found in the stroma of the of the cancer.

This invention provides a vaccine for cancers which is of epithelial, mesodermal or neuroectodermal origin. Examples of epithelial cancers are breast cancers and endometrial cancers of the uterus. An example of a mesodermal origin cancer is sarcoma. One example of a neuroectodermal origin cancer is a melanoma.

This invention also provides a method for stimulating or enhancing in a subject production of antibodies which recognize a ganglioside comprising administering to the subject an effective dose of a vaccine for stimulating or enhancing in a subject to which the vaccine is administered, production of an antibody which recognizes a ganglioside, comprising an amount of ganglioside or oligosaccharide portion thereof conjugated to an immunogenic protein effective to stimulate or enhance antibody production in the subject, an effective amount of adjuvant and a pharmaceutically acceptable vehicle.

In an embodiment of the above-described method, the ganglioside is GM2.

This invention further provides a method for treating cancer in a subject afflicted with cancer comprising administering to the subject an effective dose of a vaccine for stimulating or enhancing in a subject to which the vaccine is administered, production of an antibody which recognizes a ganglioside, comprising an amount of ganglioside or oligosaccharide portion thereof conjugated to an immunogenic protein effective to stimulate or enhance antibody production in the subject, an effective amount of adjuvant and a pharmaceutically acceptable vehicle, wherein the subject is afflicted with cancer and the antibody produced in the subject upon administration of the vaccine effectively treats the cancer.

This invention further provides a method for preventing cancer in a subject susceptible to cancer comprising administering to the subject an effective dose of a vaccine for stimulating or enhancing in a subject to which the vaccine is administered, production of an antibody which recognizes a ganglioside, comprising an amount of ganglioside or oligosaccharide portion thereof conjugated to an immunogenic protein effective to stimulate or enhance antibody production in the subject, an effective amount of adjuvant and a pharmaceutically acceptable vehicle, wherein the subject is susceptible to cancer and the antibody produced in the subject upon administration of the vaccine effectively prevents the cancer.

This invention also provides a method of using the above-described vaccine, wherein the ganglioside or oligosaccharide portion thereof is conjugated to Keyhole Limpet Hemocyanin or a derivative of Keyhole Limpet Hemocyanin. This invention further provides a method of using the above-described vaccine wherein the adjuvant is QS-21.

This invention further provides a method of using the above-described vaccine for treating or preventing cancer, wherein cells of the cancer have gangliosides on their surface.

This invention further provides a method of using the above described vaccine for treating or preventing cancer, wherein gangliosides-are found in the stroma of the cancer.

This invention further provides a method of using the above-described vaccine for treating or preventing cancer, wherein the cancer is of epithelial origin or neuroectodermal origin. One such cancer of neuroectodermal origin is a melanoma.

For the purposes of this invention "pharmaceutically acceptable vehicles" means any of the standard pharmaceutical vehicles. Examples of suitable vehicles are well known in the art and may include, but not limited to, any of the standard pharmaceutical vehicles such as a phosphate buffered saline solutions, phosphate buffered saline containing Polysorb 80, water, emulsions such as oil/water emulsion, and various type of wetting agents.

The vaccine of this invention may be administered intradermally, subcutaneously and intramuscularly. Other methods well known by a person of ordinary skill in the art may also be used.

In a preferred embodiment this invention provides a method for stimulating or enhancing in a subject production of antibodies which recognize a ganglioside comprising administering to the subject an effective dose of a vaccine for stimulating or enhancing in a subject to which the vaccine is administered, production of an antibody which recognizes a ganglioside, comprising an amount of ganglioside or oligosaccharide portion thereof conjugated to an immunogenic protein effective to stimulate or enhance antibody production in the subject, an effective amount of adjuvant and a pharmaceutically acceptable vehicle, wherein the administering comprises administering the effective dose at two or more sites. "Administering the effective dose at two or more sites" means that the effective dose is divided into two or more portions and each portion is administered at a different site of the subject. In a specific embodiment, the administering comprises administering at three sites.

This invention will be better understood from the Experimental Details which follow. However, one skilled in the art will readily appreciate that the specific methods and results discussed are merely illustrative of the invention as described more fully in the claims which follow thereafter.

Experimental Details

First Series of Experiments

Experimental Details

Increased immunogenicity of GD3 conjugate vaccines: Comparison of various carrier proteins and selection of GD3-KLH for further testing.

Tumor associated gangliosides are known to be suitable targets for immune attack against cancer but they are poorly immunogenic. Active immunization results in low titer antibody IgM responses of short duration. Covalent attachment of poorly immunogenic antigens to immunogenic carrier proteins is a potent method for enhancing the humoral response. GD3, a dominant ganglioside on malignant melanoma, was attached to carrier proteins by two methods. It was bound by th glucose of GD3 oligosaccharide but this resulted in loss of antigenicity and induction of antibodies that failed to-react with GD3 or GD3 expressing melanoma cells. In the second method GD3 was modified by ozone cleavage of the double bond in the ceramide backbone, an aldehyde group was introduced and this group was coupled by reductive amination to aminolysyl groups of proteins. Utilizing this method, conjugates were constructed with synthetic multiple antigenic peptides (MAP) expressing repeats of a malaria T-cell epitope, outer membrane proteins (OMP) of *Neisseria meningitidis*, cationized bovine serum albumin (cBSA), keyhole limpet hemocyanin (KLH) and polylysine. The antigenicity of conjugates was confirmed by reactivity with various antibodies and the immunogenicity was tested in mice. Antibody levels in immune sera were analyzed by ELISA and by dot blot immune stains on purified gangliosides. Specificity of sera reactivity was further analyzed by immune thin layer chromatography using tumor tissue extracts. GD3 conjugate vaccines resulted in significantly improved antibody responses, especially with GD3-KLH conjugates. High titer IgM and IgG responses against GD3 were induced. This method is applicable to other gangliosides and may be suitable for construction of ganglioside vaccines against a variety of ganglioside rich human cancers.

Materials and Methods

Glycolipids. GM3, GM2 and GD1b and extracted from bovine brain, were provided by Fidia Research Laboratory (Abano Terme, Italy). GD2 was made from GD1b by treatment with β-galactosidase. (Cahan et al., 1982). GD3 (me1) was isolated from human melanoma tissue (Ritter et al. 1991), GD3 (bbm) (used for vaccine preparation) and GT3 were isolated from bovine buttermilk and kindly provided by Dr. R. K. Yu (Medical College of Virginia, Richmond, Va.)(Ritter et al., 1990a). Disialyllactose (GD3 oligosaccharide) was isolated from bovine colostrum as previously described (Nicolai et al., 1978).

Chemicals. HPTLC silica gel plates were obtained from E. Merck (Darmstadt, FRG); Sep-Pak C18 cartridges from Walters Associates (Mildford, Mass.); 4-chloro-1naphtol, p-nitrophenyl phosphate disodium, sodium cyanoborohydride from Sigma Chemical Co. (St. Louis, Mo.); cyclophosphamide (Cytoxan) from Mead Johnson (Syracuse, N.Y.); QS-21 containing a saponin Quil A component from Cambridge Biotech (Worcester, Mass.).

Proteins. Poly-L-lysine hydrobromide (MW(vis)3800) was purchased from Sigma; Keyhole limpet hemocyanin (KLH) from Calbiochem (LaJolla, Calif.); cBSA-Inject Supercarrier Immunemodulator from Pierce (Rockfort, Ill.); *Neisseria meningitidis* outer membrane proteins (OMP) were kindly provided by Dr. M. S. Blake (Rockefeller University, New York, N.Y.). Multiple Antigenic Peptide (MAP) YAL-IV 294-I containing 4 repeat of a malarial T-cell epitope was a gift from Dr. J. P. Tam (Rockefeller University, New York, N.Y.).

Monoclonal Antibodies. Rabbit anti-mouse immunoglobulins conjugated to horseradish peroxidase for ITLC, and rabbit anti-mouse IgM and IgG conjugated to alkaline phosphatase for ELISA, were obtained from Zymed (San Francisco, Calif.); anti-GD3 mAb R24 was generated (Houghton et al., 1985).

Serological Assays. Enzyme-linked Immunosorbent Assays (ELISA) were performed previously described (Livingston et al., 1989). To control for nonspecific "stickiness", immune sera were also tested on plates which were processed identically but to which no ganglioside had been added, and the reading was subtracted from the value obtained in the presence of ganglioside. The titer was defined as the highest dilution yielding a corrected absorbance of 0.1 or greater. Immunostaining of gangliosides with monoclonal antibodies or mouse sera was performed after separation on high performance thin layer chromatography (HPTLC) silica gel glass plates as previously described (Hamilton et al., 1993). Plates were developed in solvent 1: chloroform/methanol/water (0.25% $CaCl_2$)50:40:10 (v/v) or solvent 2: ethanol/n-butanol/pyridin/water/acetic acid 100:10:10:30:3 (v/v) and were visualized with resorcinol/HC1 reagent as well.

Immunization. Six-week-old female BALB/cxC57BL76 F1 mice (The Jackson Laboratory, Bar Harbor, Me.) were given i.p. injections of cyclophosphamide (15 mg/kg) 3 days before the first immunization and randomly assigned to treatment groups. Groups of 4 or 5 mice were given s.c. injections of a give three vaccines 2 weeks apart if not otherwise indicated. Each vaccine contained 20 ug GD3 or 15 ug Disialyllactose plus 10 ug QS-21 in a total volume of 0.1 ml PBS/mouse. Mice were bled from the retro-orbital sinus before and 2 weeks after the vaccine if not otherwise indicated.

GD3 conjugate preparation. GD3 (2 mg) was dissolved in 2 ml methanol by sonication and cooled to −78C. in an ethanol/dry-ice bath. Ozone was generated in a ozone generator (Del Industries, San Luis Obispo, Calif.) and was conducted through the sample for 30 minutes under vigorous stirring (Crigee 1957 Wiegandt and Baschang 1965). Excess of ozone was displaced with nitrogen during 10 minutes. 100 ul $S(CH_3)_2$ was added (Pappas et al., 1966), the sample k pt at −78° C. for 30 min, then at room temperature for 90 min under vigorous stirring. The sample was dried under a stream of nitrogen and monitored by HPTLC. The long chain aldehyde was separated by adding 2 ml n-hexane to the dry sample, followed by sonication for 5 min and centrifugation at 2000 g for 15 min. The n-hexane was carefully drawn off and discarded, and the sample was dried under a stream of nitrogen. Cleaved GD3 and native GD3 were separated by HPLC (Waters, System 501, Milford, Mass.) utilizing a C18 reversed phase column (10×250 mm, Rainin Instruments, Ridgefield, N.J.). Gangliosides were eluted with methanol, monitored at 214 nm and fractions were analyzed by HPTLC as well. Fractions that contained cleaved GD3 were combined and were evaporated at 37° C. with a rotavapor (Buchi, Switzerland). Cleaved GD3, protein carrier in PBS and 2 mg sodium cyanoborohydride were incubated under gentle agitation at 37° C. for 48 h. After 16 h another 1 mg $NaCNBH_3$ was added. The progress of coupling was monitored on HPTLC. In solvent 1 and solvent 2 GD3-protein conjugates did not migrate and appeared as a resorcinol positive band at the origin. The mixture was dialyzed across 1000 MWCO dialysis tubing with three changes of each 41 of PBS at 4° C. for 48 h and were passed through an Extractigel detergent removing gel (Pierce) for final purification of unconjugated GD3. The samples were lyophilized and their protein and ganglioside content was determined by Biorad protein assay and by neuraminic acid determination according to Svennerholm (1957).

Disialyllactose was isolated from bovine colostrum as described previously (Nicolai et al., 1978). The carbohydrate was attached to protein by reductive amination (Gray, 1974) 10 mg disialyllacotse was incubated with 2 mg of proteins in 2 ml PBS for 14 days at 37° C. 2 mg sodium cyanoborohydride was added at the beginning and 1 mg was added additional every 3 days. The coupling was monitored by HPTLC in solvent 2. The disialyllactose conjugates were purified by dialysis across 1000 MWCO dialysis membrane followed by lyophilization. The protein and neuraminic acid content was determined as described above. Disialyllactose was also conjugated to proteins according to a method described by Roy and Laferriere (1990). During this procedure N-acroloyled glycopyranosylamine derivatives of the oligosaccharide were formed first, followed by conjugation via Michael addition to amino groups of the protein. Purification and protein and neuraminic acid determination was performed as described above. Determination of IgG subclass. The determination of IgG subclass was performed by ELISA using subclass-specific secondary MAbs. Secondary Mabs were used at lowest dilution that did not show reactivity with presera or negative control sera. Alkaline phosphatase conjugated to goat anti-mouse was used as third antibody at a dilution of 1:200.

FACS Analysis of Mouse Antisera

A single cell suspension of the melanoma cell line SK-MEL-28 was obtained after treatment with 0.1% EDTA in PBS followed by passage through a 26½ gauge needle. Cells ($3\times10^5$) were incubated with 40 µl of 1:20 diluted post- or pre-immunization serum for 30 minutes on ice. The cells were washed three times with 3% fetal calf serum in PBS. Thirty µl of diluted (1:50) fluorescein isothiocyanate-labeled goat anti-mouse IgG (Southern Biotechnology Associates Inc., Birmingham, Ala.) were added as secondary antibody, followed by incubation ice for 30 min. Cells were washed three times as above and resuspended in 500 µl 3% fetal calf serum in PBS and analyzed by flow cytometry (FACScan, Becton Dickinson, San Jose, Calif.).

Results

Preparation and Characterization of GD3 Vaccines

GD3 from bovine buttermilk was selectively cleaved at the C4–C5 double bond in the ceramide portion by using ozone. In methanol, methoxyperoxides appear to be intermediate products which are readily reduced with dimethylsulfite. The result of this cleavage was a GD3 derivative with an aldehyde functional group at the position of the former double bond in the ceramide portion and the elimination of a long chain aldehyde (FIG. 1). Successfully cleaved GD3 migrated below native GD3, and due to simultaneously cleaved unsaturated fatty acids it appeared as a double band on HPTLC (see HPTLC, insert in FIG. 1). Densitometric determination of HPTLC revealed a cleavage of >70% of GD3 isolated from bovine buttermilk. Initial experiments with prolonged ozone treatment periods did not change the ratio, indicating that ~30% of GD3 from this source consist of sphinganin or phytosphingosine analogs. Cleavage of GD3 at −78° C. with a reaction time of up to 1 h depending on the amount of GD3 used, was found to be optimal. Cleaved GD3 persisted only in acidic and neutral phosphate butters for up to 72 h but with increasing amount of a byproduct. Due to B-elimination reactions, release of the oligosaccharid part of GD3 occurred increasingly with time as has been described earlier to take place readily at a basic pH (Wiegandt and Baschang, 1965). The carbohydrate part released from GD3 did not migrate in solvent 1 but did comigrate with disialyllacotse isolated from bovine colostrum in solvent 2 used for separation of oligosaccharides (not shown). The decreased hydrophobicity of cleaved GD3 compared to native GD3 allowed its separation by HPLC on C18 reversed phase columns. Utilizing isocratic elution with methanol, cleaved GD3 with proteins resulted in formation of Schiff-bases between the modified ganglioside and e-aminolysil groups. They were reduced to form stable secondary amine bonds between the ganglioside and the protein by using sodium cyanoborohydride (Borch et al., 1971). The reducing agent was selective, and aldehyde groups were not reduced in phosphate buffers at pH=6.5–7.5. The reaction was monitored by HPTLC and changing ration between cleaved GD3 and a resorcinol positive band that appeared at the origin was seen. This band indicated the formation of the neo-glycoconjugates. The reaction was normally completed after incubation for 48 h. at 37° C. Disialyllactose was readily removable by dialysis, excess cleaved GD3 by passage through a detergent removing column. The degree of coupling was determined by sialic acid and protein determinations. The weight ratio of GD3 to proteins in the conjugates depended on the accessibility of lysine groups in the different proteins and is given in Table 1. The average yield of GD3 coupled to proteins overall was 30%.

The carbohydrate part of GD3, disialyllactose, was coupled to proteins utilizing two different methods. The conjugation of disialyllactose, was performed by reductive amination resulting in the open ring form of the glucose conjugated to proteins (Gray et al., 1978). The method required a long incubation period of the oligosaccharides with proteins and yields were less than 20%. The second oligosaccharide conjugation method (Roy and Laferriere 1990) resulted in a closed terminal glucose ring coupled to proteins.

TABLE 1

Reciprocal ELISA titer against GD3

| Vaccine | No. of mice | GD3/ Protein weight ratio | IgG | IgM |
|---|---|---|---|---|
| GD3 | 5 | — | 0(5) | 20(3), 0(2) |
| GD3-ganglioside conjugate: | | | | |
| GD3-KLH[a] | 14 | 0.69 | 10240(2), 5120(2), 2560(3), 1280(2), 80, 40 (2), 0 | 2560, 1280(2), 640, 320(3), 160(2), 80(3), 20, 0 |
| GD3-CBSA | 15 | 0.77 | 2560(2), 320(2), 160, 80 (2), 40 (4), 20 (2), 0(2) | 80(2), 40(2), 20(7), 0(4) |
| GD3-OMP | 15 | 0.93 | 2560, 80 (4), 20 (3), 0(7) | 1280, 320(2), 160(7), 80(4), 40 |
| GD3-MAP | 10 | 1 | 40, 0(9) | 160(2), 40(4), 20(3), 0 |
| GD3-Polylysine | 10 | n.d.[b] | 0(10) | 320, 160 (4), 80, 40, 20 (2), 0 |
| GD3-oligosaccharide conjugate: | | | | |
| Disialo-KLH[c] | 4 | 0.055 | 0(4) | 160(3), 80 |
| Disialo-cBSA[c] | 4 | 0.16 | 20, 0(3) | 40, 20 (3) |
| GD3-KLH[d] | 4 | 0.25 | 20, 0(3) | 40(2), 0(2) |
| GD3-cBSA[d] | 4 | 0.34 | 0(4) | 0(4) |
| GD3-Polylysine[d] | 5 | n.d.[b] | 0(5) | 80(3), 40(2) |

[a]KLH: keyhole limpet hemocyanin, cBSA: cationized bovine serum albumin, OMP: meningococcal outer membrane proteins, MAP: multiple antigenic peptide, Polylysine: poly L-lysine
[b]n.d.: not done
[c]open ring
[d]closed ring Serological Response Against GD3 After Vaccination with GD3-Protein Conjugate Vaccines Preimmunization sera did not show IgM or IgG reactivity with GD3. Immunization with 20 ug GD3 alone or mixed with 10 ug of the adjuvant QS-21 failed to induce GD3 antibodies (Table 1). Some groups of mice immunized with 20 ug of GD3 conjugated to proteins plus 10 $\mu$g QS-21 showed increased immune responses against GD3. GD3-poly-L-lysine conjugate, representing a high density of GD3 epitopes, induced a moderate titer IgM response (range 1/20–1/320) and no IgG response. GD3-conjugated to outer membrane proteins of Neisseria meningitidis (GD3-OMP), also induced moderate titer IgM (range 1/20–1/320) and low titer IgG (range 1/20–1/80). Only one mouse showed high titer IgM response of 1/1280 and high titer IgG of 1/2560 after vaccination with GD3-OMP. GD3 conjugated to cationized BSA(GD3-cBSA), showed low titer IgM by ELISA (range 1/20–1/80) and high titer IgG(range 1/20–1/2560). The synthetic MAP peptide, containing a malarial T-cell epitope, provided 8 free aminogroups at its aminoterminal end and 4 were able to be conjugated to GD3. GD3-MAP induced low titer IgM (range 1/20–1/160) and only one mouse produced low titer IgG response of 1/40. GD3 conjugate to KLH (GD3-KLH) induced the highest response compared to other conjugates, with highest titer IgM (range 1/20–1/2560), as well as highest titer IgG (range 1/40–1/10240) response. Immunization with both types of disialyl-lactose protein conjugates induced only low titer IgM that was cross reactive with GD3 ganglioside (range 1/20–1/160) and no significant IgG response.

Specificity of GD3 Reactive Sera by Immune Thin Layer Chromatography

Immune thin layer chromatography (ITLC) allows testing or GD3 antis ra on human tissue ganglioside extracts and to determine specificity to tumor derived gangliosides. Examples of ITLCs with human tissue extracts and high titer IgM and IgG sera induced by immunization with GD3-KLH conjugate are shown in FIGS. 3a and 3b. Sera were tested at a 1/150 dilution against ganglioside extract of human brain, neuroblastoma, melanoma, as well as against the immunogen GD3 (bbm) isolated from bovine buttermilk. The reactivity on ITLC was compared with resorcinol stained HPTLC which shows the total ganglioside composition found in these tissues. Normal brain predominantly contains GM1, GD1a, GD1b and GT1b, while the neuroblastoma extract contains in addition the major gangliosides GD2 and GM2 and the melanoma extract contains mainly GM3 and GD3. IgG antisera showed specific reactivity only with GD3 in all three tissues extracts tested (FIG. 3a), as did the control mAb R24. IgM antisera (FIG. 3b) on the other hand showed some cross reactivity with structurally related gangliosides and sulfatide in brain extract. Immune responses induced by vaccination with other GD3 conjugates showed the same specific reactivity, but were weaker and more concentrated antisera had to be used (not shown). High titer antisera identified by ELISA in mice immunized with GD3-cBSA showed high background by ITLC. A variety of blocking agents were used with these sera unsuccessfully. No specific reactivity with GD3 in tissue extract could be detected.

Specificity of GD3 Reactive Sera by Dot Blot Immune Stains

The specificity of all high titer IgM and IgG antisera (by ELISA>1/160) was studied with purified gangliosides GM3, GD2, GD1b, CD3 and GT3 isolated from bovine brain or buttermilk, and with GD3 isolated from human melanoma tissue. These structurally related gangliosides were spotted onto nitrocellulose strips in similar amounts and reacted with immune sera. A sample of dot blot immune stain experiments with sera obtained before and after immunization of mice with GD3-KLH and GD3-OMP is shown in FIG. 4. Presera did not show any reactivity with these gangliosides. Sera obtained after immunization with GD3-KLH showed specific IgM and IgG reactivity with GD3 from bovine buttermilk (the immunogen) as well as with GD3 isolated from human melanoma tissue. In some cases cross reactivity with GT3 was seen, a reaction observed also with the positive control mAb R24 (Houghton et al., 1985). High titer sera from mice immunized with GD3-cBSA showed only background reactivity but no specific reactivity against any ganglioside was detected (not shown). Dot blot reactivity induced by other GD3 conjugates were specific for GD3 (not shown). The results indicate that specific high titer IgM and IgG responses can be induced in mice with GD3-protein conjugates, and that the strongest reactivity was induced with GD3-KLH conjugates. The conjugated method seems to preserve the important epitopes on the GD3-oligosaccharide chain and GD3-conjugates did not induce cross reactivity with structurally related gangliosides.

Cell Surface Reactivity of Immune Sera Determined by FACS Analysis:

Sera from mice were tested for binding to cells of the melanoma cell line SK-MEL-28, a cell line known to express cell surface $G_{D3}$. A representative example of a FACS analysis utilizing a fluorescein isothiocyanate-labeled secondary goat anti-mouse antibody is shown in FIG. 5. Sera before and after immunization with $G_{D3}$-KLH and QS-21 were tested. Preimmunization serum stained 8% of the target cells, postimmunization serum 92%.

Discussion

An approach for construction of gangliosid conjugate vaccines is described here to 1) establish a coupling reaction with proteins applicable to different tumor gangliosides, 2) increase the immunogenicity of GD3 as the major ganglioside associated with melanoma and, 3) define the most effective protein carrier. Ganglioside conjugation must be accomplished without altering the immune dominant carbohydrate moiety. It has been shown that modification of GD3 in its carbohydrate portion for example conversion of carboxyl groups to amide groups, increases the immunogenicity of the synthetic antigens but there was no significant cross reactive antibody response with native GD3 (Ritter et al., 1990b). Consequently, this approach aimed at coupling GD3 via its ceramide portion without alteration of the carbohydrate part. The ceramide, characteristic for all gangliosides, was cleaved with ozone at the C4 position of the sphingosine base and a functional aldehyde group was introduced. Coupling to proteins was realized by reductive amination to form a stable amine bond between ganglioside and ∈-aminolysyl groups of proteins. Cleavage of gangliosides by ozonolysis and subsequent conjugation has not yet been described and it was assumed that the aldehyde intermediate of gangliosides is instable. Fragmentation has been reported, when initiated by the attack of hydroxy ions under alkaline conditions, migration of double bond occurs and β-elimination causes release of the oligosaccharide part (Kanfer and Hakomori, 1983; Wiegandt and Baschang, 1965). The aldehyde function is found to be sufficiently stable at neutral pH, Schiff bases with amino groups of proteins are readily formed and β-elimination occurs only to a small extend. An overall yield of 30% was comparably efficient as described for the conversion of gangliosides into lyso-derivatives (Neuenhofer et al., 1985). The aldehyde derivative of GD3 did not react any longer on immune thin layer chromatography (ITLC) with mAb R24. A similar phenomena has been described in connection with the reactivity of mAb M2590 with GM3 and reactivity was dependent on the acyl chain length (Itonori et al., 1989). On the other hand, GD3 protein conjugates, showed reactivity with mAb R24 by ITLC and western blot, indicating that immune dominant epitopes were restored in the GD3 neoglycoconjugates.

Once the conjugation method for generation of ganglioside vaccine established, appropriate carrier proteins had to be selected. Lowell et al. (1988) described an elegant vaccine system that induced high titer antibody responses by complexing of bacterial carbohydrate and peptide antigens via a synthetic, hydrophobic foot into outer membrane proteins (OMP) of Neisseria meningitidis and effective without additional adjuvant (Donnelly 1991). This system was directly applicable to gangliosides due to their amphipatic nature. In previous experiments, applicants absorbed gangliosides by hydrophobic interaction onto these proteins and were able to induce high titer IgM responses (Livingston et al., 1993b). Covalent attachment was utilized, but GD3-OMP conjugate induced only occasional IgG responses and the IgM response did not exceed results of previous trials without conjugation of GD3. Cationized BSA, which has been reported to be a potent immune modulator for protein antigens (Apple et al., 1988), was able to enhance specific immune response to poorly immunogenic proteins after conjugation. GD3-cBSA conjugates induced only moderated IgM response, but high titer IgG antibodies were analyzed by ELISA. Further examination of these high titer antisera by ITLC or dot blot immune stains indicated that the response was not specific for GD3. Another appealing approach for vaccine construction has been described by J. Tam et al., (Tam, 1998, Tam and Lu, 1989) as a multiple antigenic peptide system (MAP). Based on an oligomeric branching lysine core, MAPs consist of four or eight dendritic peptide arms containing B-and T-cell epitopes. The immune response to peptides was dramatically increase when these constructs were used in comparison to the peptides with B-cell or T-cell epitopes alone. When GD3 was attached to the amino terminal end of a MAP structure, containing a malarial T-cell epitope, only moderate IgM and no IgG response against GD3 was detected. Although this approach is very effective for synthetic peptides it seems to be of litter use for gangliosides vaccines. It has been reported, that anti gangliosides antibodies can distinguish between tumor derived GM3 and GM3 on normal tissue because of their different cell surface density (Nores et al. 1987). The conjugation of GD3 to polylysine was thought to represents a high density of GD3 epitopes combined on a single molecule. The response to GD3-polylysine was moderate, only medium titer IgM response was detectable and no IgG response. Finally, the mice immunized with GD3 conjugated with keyhole limpet hemocyanin, GD3-KLH, were able to generate the highest titer IgM and IgG responses and significantly higher than those generated by previous vaccines.

These sera when tested by immune stains assays were found to be highly specific for GD3 in human tissue extracts. Time course experiments of the IgM immune response indicated similar characteristic as observed in previous trials (FIG. 2). IgM peak titer were received after the third vaccination when administered in biweekly intervals. The response declined fast and continuous vaccination did not induce a significant boost in antibody response. This is the first report to show induction of high titer IgG response using ganglioside vaccines. This response lasted significantly longer than IgM response and was boosted by continuous vaccination, but was not comparable to the exponential potentiation of response often seen with protein antigens. The subclass was determined as mainly IgG1 and it is not clear if T-cell d pendent pathways were activated with ganglioside conjugate vaccines. Although th importance of T-cell help in B-cell maturation is undoubted, the regulation of antibody class is controversial and several reports have shown that isotype switch is possible with T helper cell activity (Teale and Abraham, 1987). Conjugates containing solely the oligosaccharide part of GD3 were found not to be reactive with mAb R24 and were not able to induce a significant immune response against GD3 ganglioside. Modification of the glucose at the reducing end of the oligosaccharide chain during conjugation or the missing part of the ceramide may influence the proper epitope presentation and the detection by the immune system. Both methods used for conjugation were less efficient and yields were low. The induction of a specific immune response against tumor associated gangliosides with less effective vaccines in patients induced already immune responses and were associated with better prognosis. Ganglioside conjugate vaccines showed their ability to induce long lasting and specific IgG response in mice with suggest, that especially GD3-KLH conjugate may soon prove usefulness as tumor vaccine in melanoma patients.

Second Series of Experiments

A Phase I trial of the immunological adjuvant QS-21 in melanoma patients vaccinated with the ganglioside GM2 covalently attached to KLH.

Objective: To determine the optimal safe dose of the immunological adjuvant QS-21 for induction of antibodies against GM2

BACKGROUND

Patients with AJCC Stage III melanoma have a recurrence rate at two years and mortality rate at three years of 60–70% (Hilal et al. 1981; Eilber et al. 1976). Patients with Stage IV melanoma who are free of disease after surgery have a more ominous prognosis. There is no treatment known to alter these rates. The standard treatment for Stage III melanoma after surgery is close observation.

Some patients with melanoma have antibodies in their serum which react with highly restricted melanocyte differentiation antigens have been shown. In some case, it was noted that the presence of these antibodies has been associated with an unexpectedly favorable course (Livingston et al., 1987). As only few patients have these antibodies in their serum, attempts have been made to induce antibody formation by immunizing the patients with melanoma vaccines containing the relevant antigens. Vaccine prepared form whole cells have been ineffective in this regard (Livingston et al. 1982). Purified antigens, rather than whole melanoma cells are now proposed for vaccine production. In recently completed trials, patients have been vaccinated with BCG-GM2 and short lived antibody production were seen in 33 of 44 patients (Livingston et al. 1989; Livingston, 1989), but IgG antibody responses were rarely seen.

Potent adjuvants or other approaches for increasing the immunogenicity of gangliosides such as GM2, and in particular for inducing an IgG response are continuously sought. It was found to be most successful at inducing an IgG response to gangliosides in the mouse by covalent attachment to keyhole limpet hemocyanin. The basis for this is the concept of split tolerance. Studies of immunological tolerance and of ways to overcome it have shown that in a variety of experimental systems T cell unresponsiveness is more rapidly induced and more easily maintained than B cell unresponsiveness (Romball et al. 1984; Weight, 1977). Levels of circulating antigen suitable for maintaining T cell tolerance frequently fail to maintain B cell tolerance. Consequently, if T cell help is provided (as by potent irrelevant antigens such as KLH covalently attached to the desired immunogen), antibodies can be induced to tolerated T cell dependent antigens. This approach has been successfully used to induce IgG antibodies against a variety of carbohydrate antigens in experimental animals (Kundu et al. 1980; Gray 1978; Chang and Rittenberg, 1981; Longenecker et al., 1987) and recently against *H. Influenza Polysaccharide* antigen in infants.

The molecular weight of KLH is quite variable but approximate $2 \times 10^6$ daltons. It has been injected intradermally in patients, by several investigators (Berd et al., 1982) at a dose of 1 mg to induce delayed type hypersensitivity (DTH). Pyrogen free KLH has been prepared by Biomira Inc. (Edmonton, Canada) and covalently linked to GM2 at a high epitope density. (1000/1). High titer IgG responses against GM2 using these preparations mixed with immunological adjuvants in the mouse have been induced.

Of the immunological adjuvants tested in preclinical studies with KLH-conjugate vaccines such as T antigen-KLH, QS-21 has been the most effective. IgG antibody titers over 1/4000 and potent DTH are seen in most mice. T-KLH alone results in a median titer of 1/160 with no DTH. QS-21 is a carbohydrate extracted from the bark of the South American tree Quillaja saponaria Molina. The monosaccharide composition, molecular weight, adjuvant effect and toxicity for a series of these saponins has been described (Kensil et al. 1991). QS-21 was selected due to its adjuvanticity and lack of toxicity. It has proven nontoxic and highly effective at augmenting the immunogenicity of an FeLV subunit vaccine in cats (Marciani et al.) and an HIV-1 recombinant vaccine in Rhesus monkeys.

In addition, as it was shown that some patients with melanoma have suppressor cells which may interfere with immunization and that these cells can be inhibited by a low dose of cyclophosphamide (Livingston et al., 1987b), each patient will receive a low dose of cyclophosphamide prior to the first vaccination. This combined approach has been found to augment the immunogenicity of glycolipids and other antigens in experimental animals and melanoma patients (Livingston et al. 1987a; Livingston et al., 1989).

Study Population

Patients with high risk AJCC stage III or IV malignant melanoma two to eight months after surgical resection, whose pathology slides have been reviewed by the Memorial Hospital Department of Pathology and who are clinically free of disease will be eligible. They must have a performance status of >80 (Karnofsky) and an expected survival (aside from their melanoma) of at least 5 years. Pregnant women, patients with allergies to seafood and patients with creatine or bilirubin >2.0 are excluded. Patients may have received previous irradiation, chemotherapy or immunotherapy (completed 8 weeks prior to vaccination).

Treatment Evaluation

Patients must have had a thorough physical examination at Memorial Hospital and chest X-ray, CBC, serum creatinine and liver function tests within 3 weeks of treatment patients with abnormal LFT or chest X-ray results are accepted if further tests (i.e. CTT, tomograms, etc.) show no melanoma.

Vaccine Preparation
Chemistry and Manufacturing
Drug Substance
Name and Source
Proper Name:
GM2-KLH synthetic tumor associated glycoconjugate (S-TAG)
  to be used for active specific immunotherapy
GM2-HSA synthetic tumor associated glycoconjugate (S-TAG)
  to be used for skin testing of patients undergoing active specific immunotherapy with the GM2-KLH.
Chemical Name:
11$^3$NeuAc-GgOse$_3$Cer-keyhole limpet hemocyanin (KLH)
Laboratory Codes:
GM2-KLH Lot # 5
GM2-HSA Lot # 1
Manufacturer: Biomira Inc. Research Centre One, Edmonton Research and Development Park, 9411-20 Avenue Edmonton, Alberta T6N IE5 Canada.

| MATERIAL | SUPPLIER | GRADE |
|---|---|---|
| MATERIALS USED FOR THE PREPARATION OF THE GM2 HAPTEN | | |
| Acetone | BDH | ACS |
| Ammonia Solution | BDH | ACS |
| Chloroform | BDH | ACS |
| Ethanol | Commercial Alcohol Ltd. | — |
| Ethyl Ether | BDH | ACS |
| Methanol | BDH | ACS |
| 2-Propanol | Fisher UN1219 | ACS |
| Water | Travanol sterile water for irrigation. | |
| Calcium Chloride (anhydrous - 20 mesh granular) | Fisher | Certified |
| Dimethyl Sulfide | Aldrich | 99%+ |
| GM2 | Fidia | — |
| Oxygen | Linde UN1072 | UHP |
| Silica Gel | E Merck | Kieselgel 60H Art 7736 |
| Sodium Cyanoborohydride | Aldrich | 95% Pure |
| TLC Plates F254 | E Merck | Kieselgel 60H |
| MATERIALS USED IN THE CONJUGATION PROCEDURE | | |
| Keyhole limpet hemocyanin (KLH), lyophilized, 60% protein in BES [N,N-bis-(2-hydroxyethyl)-2-aminoethano sufonic acid] buffer, purity 90% | Calbiochem, San Diego, CA | — |
| Deoxycholic acid, sodium salt (DOC) (monohydrate) 98% | Aldrich | Analytical |
| Ethylenediamin tetraacetic acid | Aldrich | ACS |
| di-sodium hydrogen orthophosphate (anhydrous) (Na$_2$HPO$_4$) | BDH | Analytical |
| Sodium chloride (NaCl) | BDH | Analytical |
| Potassium dihydrogen orthophosphate (KH$_2$PO$_4$) | BDH | Analytical |
| Sodium hydroxide (NaOH) | BDH | Analytical |
| Tris (hydroxymethyl) aminomethane hydrochloride | Sigman | — |
| Sodium cyanoborohydride (NaBH$_3$CN) | Aldrich | — |
| Sepharose CL-4B | Pharmacia | — |
| Nitrogen gas (filtered) | Medigas | — |
| Human serum albumin, 25% solution (HSA) | Miles | USP, For injection |
| GM2 aldehyde | Biomira Inc. | — |

DEVELOPMENT CHEMISTRY
Data for the GM2 and GM2 Aldehyde:
The structures of GM2 and GM2 aldehyde were characterized by Biomira Inc. by $^1$H NMR spectroscopy, thin layer chromatography (TLC), FAB-MS and FT-IR.

| STRUCTURAL FORMULA | MOLECULAR FORMULA | MOLECULAR WEIGHT |
|---|---|---|
| GM2 - ganglioside (compound #1) | | |
| GalNAcB1-4GaLB1-4 GlcB1-1Cer Neu5Aca2 | $C_{67}H_{121}O_{26}N_3$ | M-1 = 1382 Solid |
| I$^3$NeuAc-GgOse$_3$Cer | $C_{69}H_{125}O_{26}N_3$ (acid) | M-1 = 1410 |
| TLC: Rf = 0.21 (65:35:8 CHCL$_3$—CH$_3$OH—H$_2$O) Rf = 0.60 (5:4:1 CHCl$_3$—CH$_3$OH-0.2% aqueous CaCl$_2$) Rf = 0.2 (7:1:1 (CH$_3$)$_2$CHOH—NH$_4$OH—H$_2$O) | | |

| STRUCTURAL FORMULA | MOLECULAR FORMULA | MOL. WT. | PHYSICO-CHEMICAL CHARACTERISTICS |
|---|---|---|---|
| GM2-aldehyde (compound #2) | $C_{53}H_{93}O_{27}N_3$ | 1204.29 | Cream White, Odorless, Amphorous Solid |

Structural Data $^1$H(DMSO-d$_6$:D$_2$)δ:9.48(d,1H,J=2, OHz), 4.79(d,1H,J= 8.5 Hz, III-1), 4.26(d,1H,J=8.0 Hz,II-1), 4.19 (d,1H,J=8, OHZ,I-1), 2.54 (dd, 1H, A-3 e), 1.88 (s, 3H, Ac), 1.78(s, 3H,Ac),0.85(t, 3H,J=6.6 Hz, CH$_3$).

FT-IR (KBr Cast, CM$^{-1}$): 3439,3420,2952,2923,2851, 1634,1070 (possibly the gem diol).

TLC Rf=0.5 (5:4:1 CHCl$_3$–CH$_3$OH–0.2% aquecous CaCl$_2$)

Data for the KLH, GM2-KLH, HSA and GM2-HSA:

The keyhole limpet hemocyanin (KLH) is a large, complex protein composed of a number of smaller molecular weight subunits. The KLH is extracted and purified from the keyhole limpet mollusk (Megathura crenulata). The KLH, HSA and the conjugates were characterized by Biomira Inc. by Sepharose CL-4B gel filtration chromatography, isoelectric focusing (IEF) and the color metric resorcinol-hydrochloric acid method (1).

| COMPOUND | SEPHAROSE CL-4B CHROMATOGRAPHY Molecular Weight (daltons) | ISOELECTRIC FOCUSING (Isoelec. pts.) | RESORCINOL-GEL HCl (# moles moles of hapten/moles of protein) |
|---|---|---|---|
| KLH | Whol mol.(2): >2 × 10⁶ Subunits: 2–7 × 10⁵ | Mult. bands between pH 4.65 and pH 6 | — |
| GM2-KLH | Whole mol.(2) >2 × 10⁶ Subunits: 2–7 × 10⁵ | Multiple bands between pH 4.65 and pH 6 | 200–1400 |
| HSA | 5–9 × 10⁴ | Broad band at pH 4.65 | — |
| GM2-HSA | 5–9 × 104 | Broad band at pH 4.65 | 2–12 |

1. L. Svennerholm, Biochimca et Biophysica Acta, 24, (1957), 604–611.
2. Using the Sepharose CL-4B gel filtration method, the whole KLH protein molecule elutes in the void.
  volume of the column which indicates that the molecular weight of KLH is >2×10⁶. This value is consistent with the range of weights given in the literature for this protein.

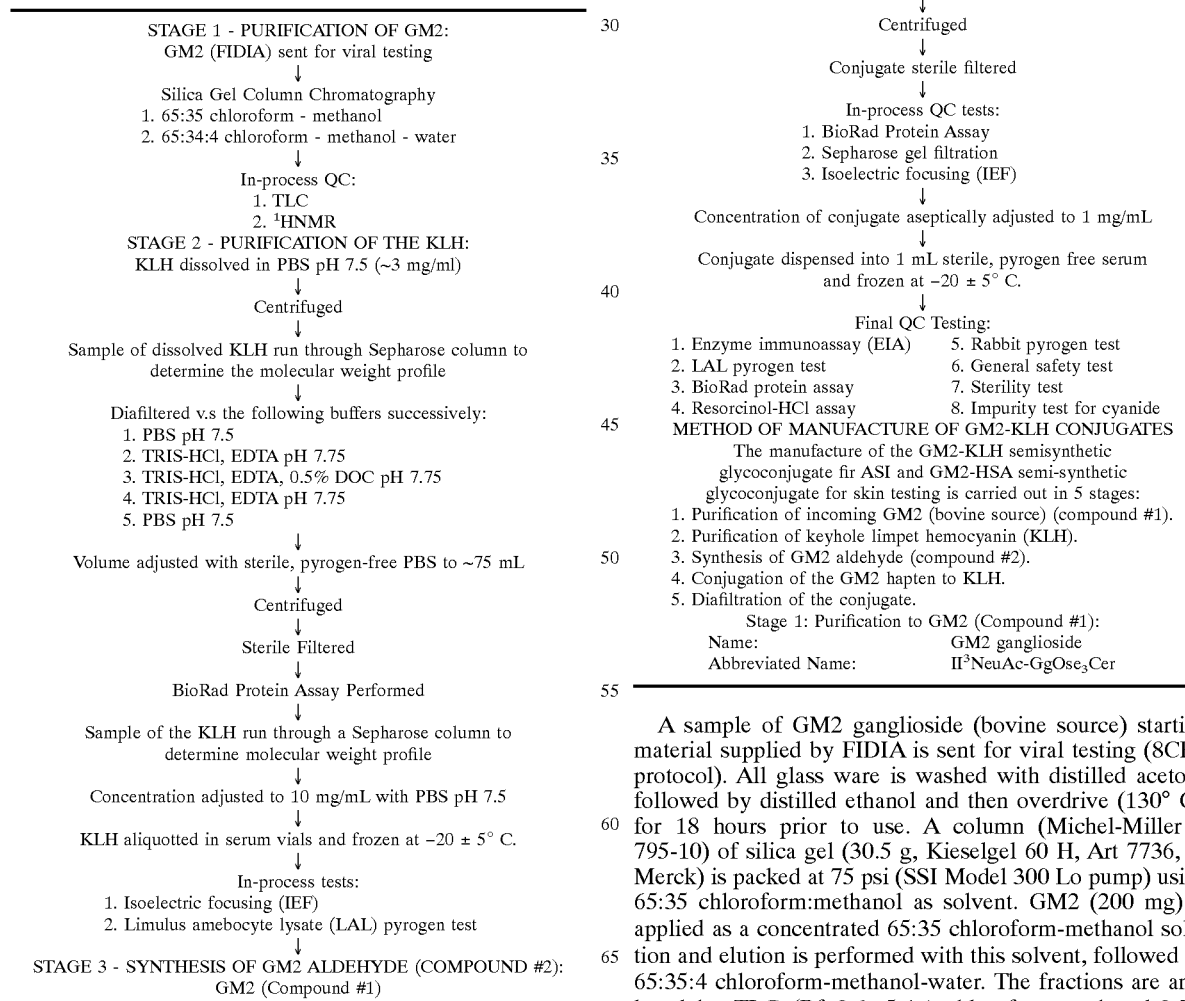

GM2-KLH MANUFACTURING FLOW CHART

STAGE 1 - PURIFICATION OF GM2:
GM2 (FIDIA) sent for viral testing
↓
Silica Gel Column Chromatography
1. 65:35 chloroform - methanol
2. 65:34:4 chloroform - methanol - water
↓
In-process QC:
1. TLC
2. ¹HNMR STAGE 2 - PURIFICATION OF THE KLH:
KLH dissolved in PBS pH 7.5 (~3 mg/ml)
↓
Centrifuged
↓
Sample of dissolved KLH run through Sepharose column to determine the molecular weight profile
↓
Diafiltered v.s the following buffers successively:
1. PBS pH 7.5
2. TRIS-HCl, EDTA pH 7.75
3. TRIS-HCl, EDTA, 0.5% DOC pH 7.75
4. TRIS-HCl, EDTA pH 7.75
5. PBS pH 7.5
↓
Volume adjusted with sterile, pyrogen-free PBS to ~75 mL
↓
Centrifuged
↓
Sterile Filtered
↓
BioRad Protein Assay Performed
↓
Sample of the KLH run through a Sepharose column to determine molecular weight profile
↓
Concentration adjusted to 10 mg/mL with PBS pH 7.5
↓
KLH aliquotted in serum vials and frozen at −20 ± 5° C.
↓
In-process tests:
1. Isoelectric focusing (IEF)
2. Limulus amebocyte lysate (LAL) pyrogen test
↓
STAGE 3 - SYNTHESIS OF GM2 ALDEHYDE (COMPOUND #2):
GM2 (Compound #1)
↓
(1) O₃, MeOH
↓
(2) CH₃SCH₃
↓
GM2 Aldehyde (Compound #2, may be the gem diol)
↓
In-process tests done in-house:
1. TLC
↓
STAGE 4 - CONJUGATION OF THE GM2 HAPTEN TO KLH:
Sterile pyrogen free KLH thawed
↓
KLH added to hapten in 4:1 ratio (w/w)
↓
Incubated at room temperature with shaking for 3 minutes
↓
NaBH₃CN is added to hapten/KLH mixture in 1:1 ratio (w/w) to hapten
↓
Reaction mixture is gently stirred at room temperature overnight then at 40° C. for 4 days
↓
STAGE 5 - DIAFILTRATION OF THE CONJUGATE:
Conjugate is diafiltered vs.:
-PBS pH 7.5
-TRIS/EDTA pH 7.75
-TRIS/EDTA/0.05% DOC pH 7.75
-TRIS/EDTA pH 7.5
-PBS pH 7.5
Conjugation aseptically removed from the Amicon filtration unit
↓
Centrifuged
↓
Conjugate sterile filtered
↓
In-process QC tests:
1. BioRad Protein Assay
2. Sepharose gel filtration
3. Isoelectric focusing (IEF)
↓
Concentration of conjugate aseptically adjusted to 1 mg/mL
↓
Conjugate dispensed into 1 mL sterile, pyrogen free serum and frozen at −20 ± 5° C.
↓
Final QC Testing:
1. Enzyme immunoassay (EIA)   5. Rabbit pyrogen test
2. LAL pyrogen test   6. General safety test
3. BioRad protein assay   7. Sterility test
4. Resorcinol-HCl assay   8. Impurity test for cyanide METHOD OF MANUFACTURE OF GM2-KLH CONJUGATES
The manufacture of the GM2-KLH semisynthetic glycoconjugate fir ASI and GM2-HSA semi-synthetic glycoconjugate for skin testing is carried out in 5 stages:
1. Purification of incoming GM2 (bovine source) (compound #1).
2. Purification of keyhole limpet hemocyanin (KLH).
3. Synthesis of GM2 aldehyde (compound #2).
4. Conjugation of the GM2 hapten to KLH.
5. Diafiltration of the conjugate.
   Stage 1: Purification to GM2 (Compound #1):
   Name:   GM2 ganglioside
   Abbreviated Name:   II³NeuAc-GgOse₃Cer A sample of GM2 ganglioside (bovine source) starting material supplied by FIDIA is sent for viral testing (8CFR protocol). All glass ware is washed with distilled acetone followed by distilled ethanol and then overdrive (130° C.) for 18 hours prior to use. A column (Michel-Miller S 795-10) of silica gel (30.5 g, Kieselgel 60 H, Art 7736, E. Merck) is packed at 75 psi (SSI Model 300 Lo pump) using 65:35 chloroform:methanol as solvent. GM2 (200 mg) is applied as a concentrated 65:35 chloroform-methanol solution and elution is performed with this solvent, followed by 65:35:4 chloroform-methanol-water. The fractions are analyzed by TLC (Rf 0.6, 5:4:1 chloroform-methanol-0.2% aqueous Cacl$_2$). The GM2 containing fractions are pooled and evaporated to give a creamy white amorphous solid.

In-process testing for this material (compound 1 includes $^1$H NMR and thin layer chromatography (TLC) to confirm the identity and purity of this ganglioside. The in-process test results must meet the specifications listed under developmental chemistry. If this material is found to be impure, the above purification is repeated.

Stage 2: Preparation of Sterile, Pyrogen-free Keyhole Limpet Hemocyanin (KLH)

Preparation of KLH:

This entire procedure is carried out inside of a Class 100 biological safety cabinet. Key hole limpet hemocyanin (KLH) supplied by Calbiochem, is dissolved in 100 mL of sterile, pyrogen-free phosphate buffered saline (PBSP pH 7.5. This solution is incubated at 2–6° C. for 18 hours to allow th KLH to dissolve into solution. The solution is then spun at 200 rpm for 30 minutes. The supernatant is collected and a sample of this is run through a Sepharose CL-4B gel column to determine the molecular wight profile of the unprocessed KLH.

Prior to dialysis of the KLH, the Amicon Stirred Ultrafiltration. Cell is made sterile and pyrogen-free by rinsing it four times first with sterile water for injection (WFI) then filling it with 95% ethanol and letting it stir for 2 hours. The unit is again rinsed with WFI water then autoclaved.

The supernatant containing the KLH is poured into the sterile, pyrogen-free 400 mL Amicon diafiltration unit with a YM 30 (30,000 molecular weight cutoff) filter. The total volume of the KLH is then brought up to 350 mL with sterile, pyrogen-free or low pyrogen content buffers successively:

1. 1 complete change of PBS pH 7.5 (sterile, pyrogen-free)
2. 3 complete changes of TRIS-HCl, EDTA pH 7.65 (sterile, low pyrogen content)
3. 2 complete changes of TRIS-HCl, EDTA pH 7.75 with 0.5% Deoxycholic acid (DOC) (sterile, low pyrogen content)
4. 4 complete changes of TRIS-HCl, EDTA pH 7.75 (sterile, low pyrogen content)
5. 3 complete changes of PBS pH 7.5 (sterile, pyrogen-free)

Each buffer change consists of bringing the volume in the Amicon unit down to 50 mL or less then adding buffer to raise the volume back up to 350 mL.

(The sterile, pyrogen-free PBS is prepared using chemicals that are baked at 180–185° C. for 4.5 hours. The chemicals are added to sterile water for injection (WFI) and mixed in a sterile, pyrogen-free container. The chemicals or the other buffers cannot be baked to depyrogenate them as they melt as such extreme temperatures, therefore, these buffers are prepared in sterile WFI water in sterile, pyrogen-free containers and sterile filtered with a 0.22 μm filter. The pH of the PBS and TRIS-HCl buffers is adjusted to the required pH using sterile, pyrogen-free 2N sodium hydroxide.)

The DOC in the TRIS, EDTA pH 7.75 buffer serves to break the pyrogens down into their lower molecular eight subunits which pass through the filter while the KLH protein is retained in the Amicon unit (8.9).

The KLH solution is aseptically removed from the Amicon unit and spun again at 2000 rpm for 30 minutes. The solution is then transferred to a sterile, pyrogen-free graduated cylinder and the final volume is adjusted to 75 mL with sterile, pyrogen-free PBS pH 7.5.

The supernatant is then sterile filtered with a 0.22 μm low protein binding filter. A sample of the KLH is run through a Sepharose CL-4B column to determine if the treatment of the KLH with the buffers (the DOC in particular) affected the molecular weight profile of the KLH compared with the initial column chromatography results of the untreated KLH. The profile should not have changed significantly. An aliquot is taken of the KLH and a BioRad protein assay performed using KLH for the standard curve. The final volume of the KLH solution is aseptically adjusted with sterile, pyrogen-free PBS 7.5 to provide a final protein concentration of 10 mg/mL.

An LAL test is done to determine the level of pyrogens present in the purified KLH. The pyrogen content must be less than 10 EU/mg for th KLH to be used in the conjugation procedure.

Isoelectric focusing (IEF) is done to check the purity and identity of the KLH. Past lots of KLH are run in parallel to act as standards.

The KLH solution is dispensed in 10 mL aliquots into sterile, pyrogen-free 30 mL serum vials and capped with sterile, pyrogen-free butyl stoppers. The KLH is then frozen at −20±5° C. until time for conjugation to the hapten.

Stage 3: Synthesis of GM2 Aldehyde (of Gem Diol, Compound #2):

All glassware is rinsed with distilled methanol and overdried (130° C.) for 18 hours prior to use. A solution of the purified GM2 ganglioside (compound #1) (40 mg) in distilled methanol (10 mL) is stirred at −15° C. (dry ice-ethanol) and ozone gas (Orec 03V10-0 ozonator) is passed through the solution for 7 minutes. A stream of argon is then passed through the solution while the reaction is checked by TLC (5:4:1 chloroform-methanol-0.2% aqueous CaCl$_2$). The solvents are then removed under reduced pressure and the resulting material is dissolved in distilled methanol. To this solution is added methylsulfide (200 ml) and the reaction mixture is stirred at room temperature for one hour. The solvents are then removed and the residue is triturated with ethyl ether(4×25 mL). The resulting white solid (compound #2) is dried in vacuo for 15 minutes to remove any remaining solvent and is then used directly in the subsequent conjugation step.

Due to the unstable nature of th resulting aldehyde (B-elimination), compound #2 is identified on a routine basis only by TLC. The TLC-of a typical run generally indicates the presence of a small amount of sphinganine or phytosphingosine analog (same Rf as compound #1) and a small amount of reducing sugar (Rf 0.32).

Stage 4: Conjugation of GM2 Hapten to KLH (or HSA):

All manipulations are done in a Class 100 biological safety cabinet.

Two vials, each containing 10 mL of the frozen sterile, pyrogen-free KLH (10 mg/mL), are thawed at room temperature immediately before use.

The KLH protein (16 mL) is aseptically measured and added to the flask containing the lyophilized GM2 hapten and a magnetic stir bar. The solution is gently agitated at room temperature for 3 minutes until all of the hapten has gone into solution. The sodium cyanoborohydride (NaBH$_3$CN) (40 mg) is added to the hapten/KLH solution then the flask is sealed with a stopper equipped with a sterile filter needle. The solution is gently shaken then incubated overnight at room temperature. The solution is then further incubated at 40° C. for 4 days.

Stage 5: Diafiltration of the Glycoconjugates (GM2-KLH):

The contents of the hapten/KLH reaction vial are aseptically transferred to the sterile, pyrogen-free Amicon ultrafiltration unit with a YM-30 filter. Filtered nitrogen is used to provide an operating pressure of 16 psi for the Amicon unit. The conjugate is then diafiltered against the following sterile, pyrogen-free or low pyrogen content buffers successively:

1. 2 complete changes of PBS pH 7.5 (sterile, pyrogen-free)
2. 2 complete changes of TRIS-HCl, EDTA pH 7.75 (sterile, low pyrogen content)
3. 2 complete changes of TRIS-HCl pH 7.75 with 0.5% Deoxycholic acid (DOC) (sterile, low pyrogen content)
4. 4 complete changes of TRIS-HCl pH 7.75 (sterile, low pyrogen content)
5. 3 complete changes of PBS pH 7.5 (sterile, pyrogen-free)

The glycoconjugate is then aseptically removed from the filtration unit and spun at 2000 rpm for 30 minutes. The supernatant is then sterile filtered with a 0.22 mm low protein binding filter.

A sample of the glycoconjugate is obtained and the following in-process QC tests are done:
1. Sepharose gel filtration
2. Isoelectric focusing (IEF)
3. BioRad protein assay Based on the results of the protein assay, the final volume of the glycoconjugate is adjusted with sterile, pyrogen-free pH 7.5 to yield a protein concentration of 1 mg/mL.

Inside of a Class 100 biological safety cabinet, the final glycoconjugate is then dispensed in 0.5 mL aliquots with an overfill volume of 0.1 mL into 1 mL sterile, pyrogen-free, clear, borosilicate serum vials with red rubber stoppers and frozen at −20° C. During the filling procedure, the air inside the filing area is monitored by exposing two blood agar plates to the air near th work area inside of the hood for a minimum of thirty minutes. These plates are then transferred to a 37° C. incubator and incubated for 1–2 days. The plates are then examined for any bacterial or fungal colonies.

The vials are placed inside of a box with a label indicating the product name, lot number and number of vials. The box is then sealed and a label with the same information is placed on the outside of the sealed box. The box is then placed in Quarantine in the fridge for 1–2 days until it can be labeled. Once the final QC tests have been done, labels are requested. The product is labeled by the manufacturing personnel then the labeling is verified by the Quality Control department or the Regulatory Affairs department. The final product file is then signed off by the manager of Regulatory Affairs and by the Vice President and COO of the Immunotherapeutics division. The product is then released and stored in a "Released Product" freezer at −20° C.

Each lot of GM2-KLH and GM2-HSA goes through the following Final Quality Control tests:
1. Enzyme Immunoassay (EIA)
2. LAL pyrogen test
3. BioRad protein assay
4. Resorcinol-HCl carbohydrate assay
5. Rabbit pyrogen test
6. General safety test
7. Sterility test
8. Impurity testing for cyanide GM2-KLH is prepared by Biomira Inc. (Edmonton, Alberta) and used under an IND with the U.S. Food and Drug Administration. The GM2/KLH molar ratio is 800/1 (actual=200–1400) and the conjugate is supplied at a concentration of 0.57 mg conjugate per 0.5 ml phosphate buffered saline (PBS). This represents approximately 70 ug of GM2 ganglioside and 500 ug KLH per 0.5 ml PBS. On the day of vaccination for the initial 5 immunizations, 0.5 ml will be placed in an individual syringe and brought to the clinic for administration. This represents a GM2 dose of 70 ug, a dose found effective in previous studies with GM2 plus various adjuvants. The final (sixth) immunization will contain one-half of this dose, 35 ug GM2 and 250 KLH.

QS-21 is extracted by Cambridge Bioscience Inc. (Worcester, Mass.) from Quillaja saponaria Molina tree bark by silica and reverse phase chromatography as previously described (16). The purified GM2-KLH conjugate and QS-21 are tested for sterility by standard culture techniques in the bacteriology laboratory, for pyrogenicity in rabbits and for safety in rabbits and mice. They are aliquoted and stored at −15 to −25° C. On the day of vaccination, 570 ug GM2-KLH (or 285 ug for the sixth vaccination) is mixed with QS-21, placed in an individual syringe, labeled, and brought to the clinic.

Four doses of QS-21 will be used, 10, 50, 100 and 200 ug, each diluted to a total volume of 0.25 ml in PBS. The first group of 3 patients will receive 6 vaccines containing 10 ug QS-21, the next 3 patients 50 ug QS-21, the next 3 patients 100 ug QS-21 and the final 3 patients 200 ug QS-21. No patient will be entered at the next dose until all 3 patients receiving the previous dose have received at least two vaccinations. If no toxicity is seen at the 200 ug dose and if the immunological reactivity to GM2 antigen and KLH has not plateaued over the 50–200 ug range, then 3 additional patients may be treated at a dose of 400 ug. Once a safe and maximally immunogenic dose has been identified, 6 additional patients will be immunized at that dose to better define the antibody response.

The IND for the use of GM2-KLH plus QS-21 is held by MSKCC.

Treatment

Three to five days before the first immunization 200 mg/M$^2$ of cyclophosphamide is administered IV. This is the dose and schedule applicants have used successfully in past vaccine trials. Four vaccinations are then administered subcutaneously at two week intervals, beginning 2–30 weeks after surgical resection of all known disease. Two additional vaccinations are administered at two month intervals.

Evaluation

Serological response: The primary end point of this trial is serologic response. Peripheral blood (30 ml) will be drawn immediately before each vaccination and 2 weeks and 5 weeks after the fourth, fifth and sixth vaccinations. Thereafter, blood may be drawn at 3-month intervals, as long as detectable antibody against GM2 persists. Sera obtained 2 weeks after the fourth, fifth and sixth vaccines from all patients will be tested by ELISA for antibodies against GM2 and related gangliosides. Patients with titers of 1/80 or greater which are shown by. ELISA and immune thin layer chromatography on a variety of glycolipids to react specifically are considered serologic responders and additional sera from serological responders may be tested to better define the antibody response to vaccination. An additional 60 ml of peripheral blood may be obtained 2 weeks after the fourth vaccination for study of the immune response against GM2 at the clonal level if applicants see evidence of high titer IgG anti-GM2 antibody induction.

Supernatants from EBV-transformed lymphoblasts and subsequently produced hybridomas will be used for this purpose.

Delayed hypersensitivity response: Skin tests for delayed hypersensitivity against KLH, GM2 and GM2 attached to human serum albumin, will be performed at the time of the fifth immunization. Reactions with more than 5 mm of induration at 48 hours will be considered positive and, if against GM2, will be studied further by skin tests with a variety of gangliosides.

Clinical course: Patients will be evaluated at Memorial Hospital at the time of their fourth and sixth vaccinations and a chest X-ray and screening profile will be performed at the time of the sixth vaccination. Additional and subsequent follow-up will be performed by their oncologists.

Criteria for Cessation of Treatment

Regional recurrence routinely treated by local therapy (surgery or intralesional injection) is no reason for cessation of treatment if the patient is rendered disease-free. Treatment will be discontinued if the patient develops recurrent disease requiring systemic treatment or radiation therapy.

Statistical Considerations

This is a Phase I study primarily concerned with an evaluation of toxicity and the IgG response against GM2 and KLH after vaccination. Three patients will be vaccinated at each QS-21 dose at 4 escalating doses. If the IgG response continues to increase with each escalation: the highest dose producing no more than grade I systemic or grade 2 local toxicity will be selected, and if no toxicity is seen a fifth dose will be tested. Based on studies in the mouse, it is expected that the IgG response to peak or plateau after th second or third dose. Once a safe and immunogenic dose range-has-been identified, 3–6 additional patients will be immunized at the dose that appears most immunogenic and at the next higher and lower doses to gain confidence in the degree of toxicity and immunogenicity at these doses.

Risks

GM2-KLH: No toxicity was observed attributed to GM2 over 100 patients treated with vaccines containing 200 ug GM2. KLH has been used at does of 1 mg to immunize and test the immune status of over 50 patients without toxicity (15). 18 patients are immunized with vaccines containing GM2-KLH. One patient has experienced pain and tenderness at vaccines sites lasting 48 hours attributable to GM2-KLH, presumably a delayed type hypersensitivity response to KLH. No dose attenuation was required. The only expected side effect of GM2-KLH is inflammation at vaccine sites lasting several days. If fever above 38° C. or severe local toxicity that limits normal activity occurs, the dose of GM2-KLH in future vaccines may be decreased by a factor of 3.

Saponins have not been used in man. They are known to be hemolytic, but the QS-21 fraction was selected because it has shown no clear toxicity at doses as high as 125 ug per mouse, cat and Rhesus monkey. On a $M^2$ or kg basis, this is thousands of times the maximal dose proposed here. Autoimmune or hypersensitivity reactions to components of the vaccine, or to skin test antigens, are a theoretical, but remote possibility.

Criteria for Toxicity: Toxicity will be graded in accordance with the common toxicity criteria developed by the National Cancer Institute (NCI). These criteria ar on file with the IRB.

Significance of Study

Augmentation of the immune response to cancer can be attempted by two basic approaches-nonspecific immunopotentiation which constitutes the bulk of past and current efforts at cancer immunotherapy, and specific immunization which has not really been evaluated in the treatment of cancer but has contributed much to the control of infectious diseases. It is the knowledge of microbial antigen which has permitted the development of successful specific immunization against infections. The lack of knowledge of human cancer antigens, on the other hand, has prevented exploration of specific immunization in the context of cancer as it should be explored, using vaccines of defined cancer-restricted antigenicity and demonstrating their immunogenicity in cancer patients. Recent progress in the definition of melanoma cell surface antigens now permits investigation of specific immunization.

Results

GM2-KLH was used as antigen in Phase I trial with QS-21. AJCC Stage III and IV melanoma patients who were free of disease after surgical resection of all known disease were immunized with 500 ug of GM2-KLH (GM2/KLH ratio 200–1400/1, GM2 dose 70 ug) plus 10, 50, 100 or 200 ug of QS-21 in groups of 3 patients each. All patients have now received the full 6 immunizations. No toxicity was associated with the 10 or 50 ug QS-21 doses. The 100 ug dose was also well tolerated, but each of the 3 patients treated at this dose had at least 1 of the 6 vaccinations which resulted in a palpable lump and tenderness for 24–48 hours and 2 of these patients had this occurrence after 2 of the 6 immunizations.

No systemic side effects were detected. The 3 patients treated at 200 ug per vaccine experienced tenderness and pain at the injection sites which lasted 2–10 days and-low grade fevers and flu-lie symptoms including mild headaches and diffuse aches and pains lasting 8–24 hours after most of the vaccinations. Serologic responses against GM2 and KLH for these 12 patients are summarized at the bottom of Table 2. While the toxicity with the 200 ug dose was not truly the maximum tolerated dose, it was significant toxicity and there was no evidence that it was associated with increased adjuvanticity compared to the 100 ug dose. An additional 9 patients are currently immunized, 3 each at the 50, 100 or 200 ug doses to confirm these toxicity and immunogenicity results. The IgM and IgG titers of the 6 patients receiving GM2-KLH plus 100 or 200 ug QS-21 are shown in FIG. 6. It appears that GM2-KLH plus QS-21 (100 ug) is a strikingly immunogenic vaccine, far superior to GM2/BCG or GM2-KLH plus DETOX or BCG with regard to both the titers and the duration of IgM and IgG antibodies.

Having shown that the GM2-KLH and GD3-KLH plus QS-21 vaccines are significantly more immunogenic that the previous ganglioside/BCG vaccines, the immunogenicity of GD2, GD3, and GD3 lactone in these new conjugate vaccines will be tested in the clinic. The basis for selecting these gangliosides as immunogens in melanoma is a quantitative analysis of twenty melanoma biopsies using immune thin layer chromatography to quantitate the levels of these gangliosides on melanomas and various normal tissues.

Six to twelve melanoma patients will be vaccinated with each of these ganglioside conjugates which have been prepared and covalently attached to KLH. Conjugates which are shown to be immunogenic in these pilot studies will then be pooled and tested in an additional group of 12 patients as a prelude to a large multi-center trial aimed at determining the impact of a consistently immunogenic polyvalent melanoma ganglioside vaccine-on recurrence rate and survival.

TABLE 2

PEAK ANTIBODY TITER AGAINST GANGLIOSIDE GM2 AFTER IMMUNIZATION WITH GM2-KLH PLUS VARIOUS IMMUNOLOGICAL ADJUVANTS

| Vaccine | Number of Patients | Antibody Titers by Elisa | | Dot Blot Immune Stain | |
|---|---|---|---|---|---|
| | | IgM | IgG | IgM | IgG |
| GM2/BCG | 6 | 640(2), 160(3), 0 | 40, 0(5) | 3⁺(4), 2⁺, 0 | 1⁺(3), 0 (3) |
| GM2-KLH | 6 | 160(2), 80 (2), 40, 0 | 0(6) | 3⁺(2), 2⁺(2), 0 (2) | 1⁺(2), 0 (4) |
| GM2-KLH + Detox | 6 | 320, 160 (4), 0 | 160, 0 (5) | 3⁺(2), 2⁺(3), | 2⁺, 0(5) |

TABLE 2-continued

PEAK ANTIBODY TITER AGAINST GANGLIOSIDE GM2
AFTER IMMUNIZATION WITH GM2-KLH
PLUS VARIOUS IMMUNOLOGICAL ADJUVANTS

|  | Number of | Antibody Titers by Elisa | | Dot Blot Immune Stain | |
| --- | --- | --- | --- | --- | --- |
| Vaccine | Patients | IgM | IgG | IgM | IgG |
| GM2-KLH + BCG | 6 | 1280, 320 (2), 80 (2), 0 | 320, 20 (2), 0 (3) | 1+ 3+, 2+ (3), 0 (2) | 1+(2), 0 (4) |
| GM2-KLH + QS-21 | 6 | 5120(2), 1280(3), 320 | 1280 (2), 640, 320 160, 80 | 3+(5), 2+ | 3+(5), 2+ |
| 10 ug | 3 | 1280, 640, 40 | 160, 80, 0 | 3+(2), 2+ | 3+(2), 2+ |
| 50 ug | 3 | 640, 320, 160 | 80(2), 40 | 3+, 2+ (2) | 3+, 2+(2) |
| 100 ug | 3 | 5120, 1280 (2) | 1280, 640, 160 | 3+(3) | 3+(3) |
| 200 ug | 3 | 5120, 1280, 320 | 1280, 320, 80 | 3+(3) | 3+(2), 2+ |

Third Series of Experiments

The cell surface gangliosides GM2, GD2 and GD3 are often overexpressed in malignant melanoma. Applicants have shown previously that immunization of melanoma patients with GM2 and BCG induced an IgM antibody response in most patients, and that patients with high titer GM2 antibodies showed increased survival. As is commonly seen with carbohydrate antigens (which are T-independent), the IgM response was short-lived, and an IgG response was rarely observed. To increase immunogenicity, applicants conjugated GM2 covalently with keyhole limpet hemocyanin (KLH). GM2-KLH vaccine was given to melanoma patients with one of three adjuvants-BCG, DETOX or QS-21. The most effective vaccine was GM2-KLH with QS-21. It induced a much higher titer and longer lasting IgM GM2 antibody response, and a consistent IgG response (isotype IgG1 and IgG3). It also induced the highest titer anti KLH response The results suggest that the conjugate GM2-KLH plus QS-21 vaccine elicited significant T cell help. As there was no serious toxicity, this vaccine approach is attractive for augmenting the immunogenicity of other gangliosides such as GD2 and GD3 and for determine the effects of ganglioside antibodies on the course of melanoma. In addition, the finding that QS-21 significantly increased the immunogenicity of GM2-KLH suggests that it may do the same for other conjugate vaccines, many of which are currently used without adjuvant.

Introduction

One of the changes that occur in the process of malignant transformation is an altered pattern of cell surface ganglioside expression in certain types of cancer, including malignant melanoma (1). In normal melanocytes, GM33 is the predominant ganglioside. Other gangliosides which include GD3, GM2, GD1a and GT1b, constitute less than 10% of the total (2). In malignant melanoma, activation of glycosylating enzymes leads to increased expression of GD3, GD2, GM2 and 9-O-acetyl GD3 (3,4). These overexpressed gangliosides are attractive targets for immunotherapy, including active immunization with ganglioside vaccines. In a series of studies involving GM2 vaccines in patients with malignant melanoma, applicants have shown that vaccination (after low-dose cyclophosphamide and with BCG as adjuvant) induces IgM antibodies to GM2 in most patients (5), and that disease-free interval and survival are extended in patients producing high-titer GM2 antibodies (6,7). However, the induced antibody response to GM2 has the characteristics of a T-independent response (predominantly IgM, short duration, inconsistent IgG response, lack of booster effect), and the other melanoma gangliosides, GD3 and GD2, are not immunogenic when administered in the same way (8). As th relevant epitopes are carbohydrates, applicants have explored approaches to increasing immunogenicity that are suggested by the successful development of carbohydrate vaccines for bacterial infections. In the mouse, applicants have shown that the immunogenicity of GD3 is markedly increased by covalent binding to keyhole limpet hemocyanin, and that nice immunized with the GD3-KLH conjugate and the adjuvant QS-21 show a high-titer IgM response followed by a strong, long-lasting IgG response (9). Applicants have now begun to test ganglioside conjugate vaccines in the clinic, and applicants report here the initial results of immunizing patients with malignant melanoma with a GM2-KLH conjugate vaccine.

Materials and Methods

Patients

Patients with malignant melanoma Stage III were considered eligible if all metastatic disease had been rejected within the last 4 months. None of the patients had received prior chemotherapy or radiation therapy.

Vaccine Preparation and Administration

GM2-KLH vaccine: GM2-KLH conjugate was prepared by Biomira Inc. (Edmonton, Alberta) as described previously for GD3-KLH conjugate vaccine (9). Briefly, the conjugation procedure involved ozone cleavage of the ceramide double bond of GM2, introduction of an aldehyde group, and conjugation to aminolysyl groups of KLH by reductive amination. The GM2/KLH molar ratio was approximately 800/1, and the vaccine was supplied at a concentration of 0.57 mg conjugate in 0.5 ml normal saline. This amount represented one patient dose and contained 70g GM2 and 500 $\mu$g KLH. Groups of six patients each received GM2-KLH conjugate without adjuvant, GM2-KLH with DETOX, GM2-KLH with BCG and GM2-KLH with QS-21.

Four vaccinations were administered intradermally into extremities with intact lymphatic drainage at two-week intervals, followed by two additional vaccinations at eight week intervals. Cyclophosphamide (Cytoxan, Mead Johnson and Co., Evansville, Ind.) 200 mg/m2 was administered intravenously to all patients 4 to 6 days prior to the first vaccination.

Immunological adjuvants: DETOX was produced and supplied by Ribi Immunochem Research Inc. (Hamilton, Mont.), formulated as a lyophilized oil droplet emulsion. It consists of cell wall skeletons (CWS) from bacille Calmette-Guorin and monophosphoryl lipid A (MPLA) from *Salmonella minnesota* R595. On the day of vaccination, 0.25 ml DETOX (250 $\mu$g CWS and 25 $\mu$g MPLA) was mixed with the GM2-KLH preparation. The vaccine (final volume 0.75 ml) was vortexed for 2–3 minutes and administered to the patients within 15 min. BCG was purchased from Bionetics Research Inc. (Rockville, Md.). On the day of vaccination, 107 viable units of BCG in 0.1 ml normal saline were added to the GM2-KLH vaccine in each individual syringe (final volume 0.6 ml). The contents were mixed and administered to the patients within 15 min. QS-21 adjuvant (a homogeneous saponin purified from the bark of Quillaja saponaria Molina (10, 11) was kindly provided by Cambridge Biotech Inc. (Worcester, Mass.). To obtain QS-21, the procedure of Kensil et al, 1991 (10) may be employed. Specifically, coarsely chopped *Q. saponaria* bark (approximately 1 cm square, obtained from Hauser Chemicals, Boulder, Colo.) was stirred with 10 ml of water/g of bark at room temperature for 1 h. The extract was centrifuged and the supernatant containing the solubilized saponins was saved. The extraction step was repeated on the bark pellet and the two supernatants were pooled. To remove nonsaponin components, the supernatant pool was lyophilized, redissolved in 40 mM acetic acid in water at a concentration of 250 mg/ml (w:v) and either chromatographed through Sephadex G-50 (medium, Pharmacia, Piscataway, N.J.) in 40 mM acetic acid with the hemolytic activity localized in the void volume fraction, or dialyzed against 40 mM acetic acid with the hemolytic activity retained by the dialysis membrane. The hemolytic fraction was lyophilized and redissolved at a concentration of 200 mg/ml in 40 mM acetic acid in chloroform/methanol/water (62/32/6, v/v/v); 1 q of this fraction was applied to Silica Lichroprep (E. M. Science, Gibbston, N.J.; 40 to 63 $\mu$M particle size, 2.5 cm I.D.×20 cm height) and eluted isocratically in the solvent used to solubilize the saponins. The elution of saponins was monitored by carbohydrate assay. Fractions containing the saponins of interest were identified by reverse phase TLC with visualization with Bial's reagent (Sigma, St. Louis, Mo.) pooled individually, and rotavapped to dryness. The fractions from the silica chromatography were then redissolved in 40 mM acetic acid in 50% methanol and loaded on a semipreparative HPLC column (Vydac $C_4$, 5 $\mu$m particle size, 3000 nm pore size, 10 mm I.D.×25 cm length). Saponin peaks, detected by absorbance at 214 nm, were eluted by using a methanol gradient at a flow rate of 4 ml/min, and individually rotavapped to dryness. Purity of saponins was assessed by analytic HPLC (Vydac $C_4$, 5 $\mu$m particle size, 3000 nm pore size, 4.6 mm I.D.×25 cm length) with a gradient of 0.1% TFA in acetonitrile. As described in Newman et al., 1992 (11), QS-2.1 is defined as the adjuvant active reverse phase HPLC fraction 21 from Q. Saponaria bark extract. 100 $\mu$g or 200 $\mu$g of QS-21 were diluted in 0.25 ml normal saline and mixed with GM2-KLH. The vaccine (final volume 0.75 ml) was vortexed for 2–3 minutes and administered within 15 min.

Gangliosides

GM2 and GD1b from bovine brain were a gift from Fidia Research Laboratory (Abano Terme, Italy). GM3, GM1 and GD1a from bovine brain were purchased from Sigma Chemical Co. (St. Louis, Mo.). Asialo-GM2 was prepared by treatment of GM2 with 0.1M trifluoroacetic acid at 100° C. for 1 h followed by separation on a Sep-Pak C18 reversed-phase column (Waters, Milford, Mass.). GD2 was made from GD1b by treatment with 8-galactosidase (12). GD3 isolated from bovine buttermilk was kindly provided by Dr. R. K. Yu (Medical College of Virginia, Richmond, Va.).

Reagents and Monoclonal Antibodies

High-performance thin-layer chromatography (HPTLC) silica gel plates were obtained from E. Merck (Darmstadt, Germany). 4-chloro-1-naphthol and p-nitrophenyl phosphate disodium were obtained from Sigma. Alkaline phosphatase-conjugated goat anti-human IgM (Kierkegaard and Perry Labs, Gaithersburg, Md.) and mouse anti-human IgG-purified (Southern Biotech, Birmingham, Ala.) followed by alkaline phosphatase-conjugated goat anti-mouse IgG (Southern Biotech) were used for enzyme-linked immunosorbent assays (ELISA). Horseradish peroxidase-conjugated goat anti-human IgM or IgG purchased from TAGO (Burlingame, Calif.) were used for dot blot immune stain and immune thin layer chromatography (ITLC). Rabbit anti-mouse immunoglobulin conjugated to horseradish peroxidase for ITLC, and rabbit anti-mouse IgM and IgG conjugated to alkaline phosphatase for ELISA were used with control monoclonal mouse antibodies, and were obtained from Zymed (San Francisco, Calif.). Anti-GM2 mAb 696 was obtained from Kyowa Hakko Kogyo (Tokyo, Japan) and anti-GD3 mAb R24 was generated (13).

Serological assays

ELISA was performed as previously described (6). To control for nonspecific "stickiness", immune sera were also tested on plates which were processed identically but to which no ganglioside had been added, and the reading was subtracted from the value obtained in the presence of ganglioside. The titer was defined as the highest dilution yielding a corrected absorbance of 0.1 or greater. Immunostaining of gangliosides with monoclonal antibodies or human sera was performed after spotting on nitrocellulose strips (14) or separation on HPTLC silica gel glass plates as previously described (0.3). Plates were developed in chloroform/methanol/water (0.25% CaCl2) 50:40:10 (v/v), and gangliosides were visualized by staining with resorcinol/HCl reagent or monoclonal antibodies.

Determination of IgG Subclass

Determination of IgG subclass was performed by ELISA using subclass-specific secondary mouse anti-human IgG1, IgG2, IgG3, and IgG4 mAbs. Secondary mAbs from different suppliers (Table 4) were used. Alkaline phosphatase conjugated to goat anti-mouse IgG (Southern Biotech, Birmingham, Ala.) was used as third antibody at a dilution of 1:200.

Complement-mediated Cytotoxicity Assays

Complement-mediated cytotoxicity assays were performed by a 4 h 51Cr release assay. Cells from the GM2-positive melanoma cell line SK-MEL-173 served as target cells. 2×106 cells were labelled with 100 $\mu$Ci Na251Cr04 (New England Nuclear, Boston, Mass.) in 10% FCS RPMI for 1 h at 37° C. in a $CO_2$ incubator. The cells were washed twice, and 104 cells/well in 96-well round-bottom plates (Corning, New York, N.Y.) were labelled and incubated with 1:5 diluted pre- or post-vaccination serum or with medium alone for 1 h at 37° C. in a CO2 incubator. The cells were washed and incubated with human complement (Sigma) at a dilution of 1:4 for 4 h at 37° C. The plates were spun at 500 g for 5 min, and an aliquot of 125 $\mu$l of supernatant of each well was harvested for determination of released 51Cr. All assays were performed in triplicate and included control wells for maximum release in 1% NP-40 (Sigma) and for spontaneous release in the absence of complement.

The percentage of specific lysis was calculated as follows:

$$\% \text{ cytotoxicity} = \frac{\text{Experimental release} - \text{spontaneous release}}{\text{Maximum release} - \text{spontaneous release}} \times 100$$

Results

Vaccine Administration and Side Effects

Twenty four patients were immunized with the GM2-KLH vaccine. Groups of six patients each received GM2-KLH with no immunological adjuvant or with DETOX, BCG or QS-21. No local or systemic toxicity was detected after administration of GM2-KLH alone. Vaccines containing DETOX resulted in nodule formation at vaccination sites in four of six patients which lasted 2–10 weeks. In four patients these were associated with 3–10 cm of erythema and induration but only minimal tenderness. In one patient it was associated with 25 cm erythema and induration after one immunization and in a second patient low grade fever and malaise for 72 hours after the first immunization. In this patient the DETOX dose was reduced to 50 $\mu$g CWS and 5

μg MPLA for subsequent immunizations. BCG produced local inflammation and crusting at some point in all patients which healed after 2–12 weeks. When this occurred, the dose of BCG was reduced from 1×107 viable units to a final dose of 3×106 units in four patients and 1×106 units in one patient. The sixth patient had a history of tuberculosis exposure and a positive PPD test. He was therefore started at a dos of 1×106 units which was eventually reduced to 1×105 units. QS-21 induced mild local erythema and tenderness lasting 24–48 hours in all patients at the 100 μg dose. The 200 μg dose of QS-21 was associated with local tenderness and inflammation lasting 2–10 days after all immunizations as well as mild flu-like symptoms including low grade fever (<38.5° C.), headache and myalgia lasting 8–24 hours after 3 of the 18 immunizations. No neurological abnormalities or other side effects were observed.

Antibody Response to GM2-KLH Conjugate Vaccines

Prior to vaccination, IgG antibodies against GM2 were not found, and IgM antibodies were detected only in three patients, with titers of 1:80 in two 1:320 in one. The remaining 21 patients showed no GM2 reactivity before vaccination. ELISA and dot blot immune stain results with sera obtained before and after immunization are summarized in Table 3. IgM antibody titers after immunization with GM2-KLH, or with GM2-KLH and BCG or GM2-KLH and DETOX, were quit similar (median titer 1:80–1:160). In contrast, 5 of 6 patients immunizated with GM2-KLH and QS-21 showed IgM antibody titers of 1:1280 or more, significantly higher than the titers in the other groups or in patients previously immunized with unconjugated GM2 and BCG vaccines (6). In addition, immunization with GM2-KLH and QS-21 induced a consistent IgG response for the first time in all patients; only 2 of the other 18 patients receiving GM2-KLH vaccines produced comparable IgG titers.

Sequential IgM and IgG antibody titers against GM2 in patients receiving GM2-KLH and QS-21 are shown in FIG. 6. IgM peak titers were seen after the third or fourth vaccination and remained high in most patients for at least 20 weeks. Booster immunizations at week 14 and 22 did not further increase IgM titers. IgG titers of 1:160 or higher were seen two weeks after the fourth vaccination in five of six patients. The titers decreased to 1:40 or less but rapidly increased again after booster vaccination to the previous levels (median 1:160) and remained at this level for more than 11 weeks. The second booster vaccination had no clear effect on antibody titers in most cases. Thus, the response to booster vaccination showed only one of two characteristics of the classical secondary immune response. The response occurred more rapidly, but antibody titers did not rise higher than after the initial immunizations.

KLH antibodies were not detected in pretreatment sera. After vaccination all patients sera showed reactivity with KLH as indicated in Table 3. The highest titers of IgG antibodies were seen after administration with QS-21, significantly higher than in all other groups, including the next-best group of patients vaccinated with GM2-KLH and BCG (p<0.005). In the QS-21 group, there was no correlation between the strength of the GM2 response and the KLH response.

Specificity Analysis of GM2 Antibodies

The specificity of ganglioside antibodies detected in the patients' sera before and after immunization was determined by dot blot immune stain utilizing the ganglioside standards GM3, asialo-GM2, GM2, GM1, GD2, GD3, GD1a and GD1b (FIG. 7). Preimmunization IgM and IgG antibodies from most patients showed weak reactivity with asialo-GM2, and some patients also had IgM antibodies against GM1 and GD1b. Reactivity with these gangliosides was not altered by immunization. The only vaccine-induced changes were strong reactivity with GM2 and weak reactivity with GD2. Dot blot immune stains were graded as 0, 1+, 2+, or 3+. 3+ reactivity of IgM antibodies against GM2 was seen in the serum of five of six patients immunized with GM2-KLH and QS-21, in one of six patients treated with GM2-KLH and BCG, and in two of six patients treated with GM2-KLH without adjuvant or GM2-KLH and DETOX. 3+reactivity of IgG antibodies was seen in five of six patients immunized with GM2-KLH and QS-21 and in none of the patients in the other treatment groups.

Postvaccination sera from patients immunized with GM2-KLH and QS-21 were also tested by immune thin layer chromatography (FIG. 8A) for reactivity with GM2 and other gangliosides of a melanoma tissue extract. Most patients' sera showed strong IgG and IgM reactivity with GM2 isolated from bovine brain or melanoma. Reactivity was seen also with a slower migrating band in the melanoma extract, presumably GD2 when comparing the Rf value with a purified GD2 standard (not shown).

To confirm the GD2 crossreactivity of IgG antibodies, postvaccination serum from patient No. 2 was preincubated with either GM2 br GD2 before performing the immune stain (FIG. 8B). Reactivity with GM2, and with GD2 in the melanoma ganglioside extract, was completely inhibited by preincubation with GM2. On the other hand, preincubation of the same serum with GD2 resulted in inhibition of GD2 reactivity only, and did not change reactivity with GM2. These results suggest the presence of two populations of antibodies, one reacting with GM2 alone and another with reactivity for GM2 and GD2.

Subclass Determination of IgG Antibodies

High titer IgG sera from the six patients immunized with GM2-KLH and QS-21 were tested by ELISA using a panel of IgG-subclass specific secondary antibodies. The results are summarized in Table 4. The IgG antibodies in all six sera were of IgG1 and IgG3 subclass.

Complement-mediated Cytotoxicity

Effector function of anti GM2 antibodies in the serum of patients vaccinated with GM2-KLH and QS-21 (diluted 1:5) was tested by complement-mediated cytotoxicity assays. As shown in Table 5, post-vaccination sera of all six patients lysed GM2-positive SK-MEL-173 melanoma cells in the presence of human complement. Prevaccination sera showed no cytotoxicity with addition of complement, and postvaccination sera were not cytotoxic with GM2 negative melanoma cells or when complement was not added. Clearly, these are only preliminary results, and more detailed study of cell surface binding and cytotoxic effector functions of vaccine-induced antibodies and their subclasses is now underway.

Discussion

In a series of studies in patients with malignant melanoma, the objective has been to construct vaccines that are effective in inducing production of antibodies against three gangliosides often overexpressed in melanoma— GM2, GD2 and GD3. The initial approach was to vaccinate patients with unconjugated gangliosides adsorbed to BCG. In this way we were able to induce antibody production against GM2 (5,6) but not GD2 or GD3. GM2 antibodies induced by GM2-BCG vaccines were mostly of the IgM class, the antibody response was of short duration, and booster immunization resulted again in a brief period of IgM antibody production similar to the primary response—all characteristics of a T-cell independent immune response, well known from studies of other carbohydrate antigens. Even so, vaccine-induced production of GM2 antibodies by patients with Stage III melanoma after surgery was associated with increased survival (6,7). This observation suggested that melanoma gangliosides are appropriate candidates for vaccine construction, and that melanoma ganglioside vaccines of increased immunogenicity might result in superior clinical outcomes. As the relevant epitopes of melanoma gangliosides are carbohydrates it is helpful to consider studies that have been aimed at increasing the immunogenicity of other carbohydrate vaccines, notably vaccines against certain bacterial infections.

The major distinction of the immune response to carbohydrate antigens, as opposed to protein antigens, is that it does not depend on the thymus. The concept that carbohydrate antigens are thymus-independent (TI) is based on the observation that neonatally thymectomized mice as well as thymic mice show unimpaired humoral immune responses to bacterial polysaccharides (15). B-cells that respond to TI antigens show several characteristic features. They appear later in ontogeny, are long-lived, and do not require T-cells for activation, at least not in vivo. Although T-cells are required for B-cells to respond to TI antigens in vitro, the nature of the T-cell effect is poorly understood and clearly different from the MHC-restricted T-cell help in the T-dependent antibody response to protein antigens. While T-cells are not indispensable for the in vivo antibody response to TI antigens, antibody levels are higher when T-cells are present, suggesting a general augmenting activity of T-cells, again by unknown mechanisms (16).

A large variety of approaches has been explored in attempts to increase the immunogenicity of carbohydrate antigens. They include chemical modification (17), administration with adjuvants, non-covalent complexing with proteins, covalent attachment to immunogenic protein carriers (18), and replacement of the carbohydrate epitope by a protein replica, either peptides synthesized de novo (so-called mimotopes, 19) or anti-idiotypic antibodies (20). Most of these approaches result in increased T cell help for the carbohydrate specific antibody response. While each has shown promise in initial experimentation, covalent attachment of carbohydrate antigens to immunogenic T-dependent protein carriers, as first suggested for haptens (21) and then disaccharides (22), is the concept that has been pursued most vigorously, resulting in vaccines that have in some instances been shown to be highly effective in recent clinical trials.

Excellent examples are *H. influenzae* type b (Hib) polysaccharide protein conjugate vaccines. Four vaccines that have been developed over the last decade differ in the carbohydrate components, protein carriers and linkers between carbohydrate and protein (23-27). In comparative studies in children, conjugate vaccines induced a much stronger antibody response than unconjugated Hib phosphoribosyl/ribitolphosphate polysaccharide (PRP) vaccine (28). Of particular interest are observations that young children first immunized with HbOC (oligosaccharide-nontoxic diphtheria toxin) or PRP-OMPC (outer membrane protein complex of *Neisseria meningitidis* type B) vaccines and later challenged with unconjugated PRP vaccine showed an anamnestic IgG response even if challenged at an age at which they do not respond to primary immunization with the unconjugated vaccine (29,30). How T-cells are engaged, and how they interact with Hib PRP-responsive B-cells, is still far from clear. The fact that increased immunogenicity and T-dependence require a covalent bond between PRP and protein suggests that the proximity between protein and PRP must not be disturbed, at least not in the early phase of antigen processing. As the isotype and biological activities of antibodies induced by Hib PRP and Hib PRP conjugates are the same, it appears that the B-cells that respond to the conjugate-induced T-cell signal are qualitatively identical with those engaged by Hib PRP alone.

Drawing on the substantial experience that has accumulated in the development of carbohydrate vaccines for bacterial infections, applicants have explored, over the past several years, similar approaches in attempts to increase the immunogenicity of melanoma gangliosides. Chemical modification of GD3, resulting in amide, lactone or gangliosidol formation, or O-acetylation, produced derivatives that were highly effective in inducing antibody production in patients with melanoma. However, the antibodies induced by these GD3 derivatives did not cross-react with GD3 (31,32). An anti-idiotypic antibody BEC-2, mimicking GD3, has been developed by immunizing mice with the monoclonal antibody R24 which recognizes GD3. Rabbits immunized with BEC-2 produced anti-GD3 antibodies (33), and initial-studies of the-immunogenicity of BEC-2 in human patients are underway.

Regarding conjugate vaccines, initial studies with GD3 in the mouse were concerned with three issues—development of the conjugation method, selection of the carrier protein, and choice of the adjuvant (7). The optimal conjugation procedure involved ozone cleavage of the double bond of GD3 in the ceramide backbone, introduction of an aldehyde group, and coupling to protein aminolysyl groups by reductive amination. Of five carriers tested—poly-1-lysine, keyhole limpet hemocyanin (KLH), cationized bovine serum albumin, *Neisseria meningitidis* outer membrane protein complex (OMPC), and multiple antigenic peptide constructs containing four repeats of a malarial T-cell epitope on a branching polylysine core-, KLH was found to be most effective. Noncovalent GD3/KLH complexes were not immunogenic. The best adjuvant was QS-21, a homogeneous saponin fraction purified from the bark of Quillaja saponaria Molina. The characteristics of the antibody response to immunization with GD3-KLH conjugate and QS-21 included a) a high initial IgM antibody titer, b) a rapid secondary rise of IgM antibody titers after booster immunizations, c) maintenance of IgM antibody titers after booster immunization for up to ten weeks, and d) consistent production of IgG antibodies at high titers, parallel to IgM antibody production except for the initial delay of two weeks. These findings have now been reproduced in human melanoma patients by immunization with another ganglioside conjugate vaccine, GM2-KLH, using the same conjugation procedure. As in the mouse studies, QS-21 proved to be a significantly more effective adjuvant than DETOX or BCG with acceptable toxicity.

The GM2 antibody response had many characteristics of a T cell dependent response. It was long-lasting, and antibodies or IgG1 and IgG3 subclass (usually associated with a T cell dependent immune response) were induced. As seen with the Hib-PRP vaccines, these isotypes were the same as those induced occasionally at low titers with unconjugated GM2/BCG vaccines. The lack of a clear booster effect in the sustained high-titer IgM and IgG response after vaccinations three and five months following the initial series may be explained by the fact that th patients were immunized at two-week intervals initially. In the classical experiment showing the secondary response to protein antigens, the second injection of antigen is given four weeks after the first. Antibody levels after the first immunization are higher between one and two weeks after the injection, and then decline to very low levels before the booster injection is given after four weeks. In the immunization schedule applicants chose, the initial antibody response did not subside but increased in a stepwise fashion in response to the first four vaccinations at two-week intervals, anticipating the secondary response that is seen in a more dramatic fashion in the classical experiment. Unlike the antibody response to most protein antigens, the IgM response was long-lasting, and IgM antibodies remained at higher titer than. IgG antibodies, even after repeated booster immunizations, as is characteristic for carbohydrate antigens. Hence the immune response against gangliosides which contain a comparably short oligosaccharide chain linked to a lipid backbone and which are autoantigens show much in common with the immune response against Hib-PRP and other bacterial carbohydrates.

The development of the GM2-conjugate vaccine will make it possible to determine whether higher levels of IgM and IgG antibodies against GM2, sustained over longer periods, will be more effective in delaying recurrence of melanoma than the lower levels of mostly IgM antibodies, present for shorter periods, in patients immunized with unconjugated GM2. In addition, applicants can now test whether conjugation with immunogenic protein carriers also confers immunogenicity to GD3 and GD2, major gangliosides which have not induced an antibody response in melanoma patients when given as unconjugated vaccines. If this can be accomplished, construction and testing of a polyvalent melanoma ganglioside vaccine would be an attractive next step.

TABLE 3

Serological response of patients receiving GM2-KLH conjugat vaccines with or without adjuvants in comparison to vaccin containing GM2 adherent to BCG (GM2/BCG)

| | | Reciprocal GM2 antibody titers | | | |
|---|---|---|---|---|---|
| | No. of | before immunization | | after immunization (Peak) | |
| Vaccine | Patients | IgM | IgG | IgM | IgG |
| GM2-KLH | 6 | 20, 0(5) | 0(6) | 160(2), 80 (2), 40, 0 | 160, 0(5) |
| median titers: | | 0 | 0 | 80 | 0 |
| GM2-KLH + DETOX | 6 | 20(2), 0 (4) | 0(6) | 320, 160 (4), 0 | 160, 0(5) |
| median titers: | | 10 | 0 | 160 | 0 |
| GM2-KLH + BCG | 6 | 80(2), 20 (2), 0(2) | 0(6) | 1280, 320 (2), 80 (2), 0 | 320, 20 (2), 0(3) |
| median titers | | 20 | 0 | 200 | 10 |
| GM2-KLH + QS-21 | 6 | 320, 20 (2), 0(3) | 0(6) | 5120(2), 1280(3), 320 | 1280, 640 (2), 320, 160, 80 |
| median titers: | | 10 | 0 | 1280 | 480 |
| GM2/BCG[a] | 58 | 160, 40, 20 (10), 10 (11), 0(35) | 0(58) | 640(11), 320(9), 160(15), 80(8), 40(8), 20(2), 10(3), 0(2) | 640, 160, 80(4), 20, 10(3), 0(48) |
| median | | 0 | 0 | 160 | 0 |

TABLE 3-continued

Serological response of patients receiving GM2-KLH conjugat vaccines with or without adjuvants in comparison to vaccin containing GM2 adherent to BCG (GM2/BCG)

titers:

| | | Reciprocal GM2 antibody titers | | Reciprocal KLH antibody titers after immunization (Peak) |
|---|---|---|---|---|
| | | Dot blot immune stain for GM2 antibodies | | |
| | No. of | | | |
| Vaccine | Patients | IgM | IgG | IgG |
| GM2-KLH | 6 | 3+(2), 2+(2), 0(2) | 1+(2), 0 (4) | 540(2), 180, 60 (3) |
| median titers: | | | | 120 |
| GM2-KLH + DETOX | 6 | 3+(2), 2+(3), 1+ | 2+, 0(5) | 1620, 540(2), 180 (3) |
| median titers: | | | | 360 |
| GM2-KLH + BCG | 6 | 3+, 2+(3), 0 (2) | 1+(2), 0 (4) | 4860, 1620(2), 540(3) |
| median titers: | | | | 1080 |
| GM2-KLH + QS-21 | 6 | 3+(5), 2+ | 3+(5), 2+ | 10240, 5120(2), 2560(3) |
| median titers: | | | | 3840 |
| GM2/BCG[a] | 58 | 3+(32), 2+ (15), 1+(4), 0 (7) | 3+(2), 2+ (5), 1+ (4), 0(47) | ND |
| median titers: | | | | ND |

[a]historical data (6)

TABLE 4

Characterization by IgG-subclass Specific M Abs of IgG Abs induced against GM2 induced with GM2-KLH plus QS-21 vaccine

| IgG subclass mABS | | | Reciprocal ELISA Titer against GM2 | | | | | |
|---|---|---|---|---|---|---|---|---|
| | conc. | mAbs | Patient No. | | | | | |
| Specificity | (ug/ul) | source | 1 | 2 | 3 | 4 | 5 | 6 |
| IgG | 10 | SBA[a] | 640 | 640 | 640 | 640 | 640 | 640 |
| | 20 | BS | 40 | 20 | 20 | nd | 20 | 20 |
| | 5 | ZLI | 640 | 640 | 640 | 640 | 640 | 640 |
| IgG1 | 10 | SBA | 10 | 10 | 10 | 10 | 10 | 10 |
| | 20 | BS | 10 | 10 | 0 | 10 | 0 | 0 |
| | 2 | ZLI | 10 | 0 | 10 | 0 | 10 | 0 |
| IgG2 | 10 | SBA | 10 | 0 | 0 | 0 | 0 | 0 |
| | 20 | BS | 0 | 0 | 0 | 0 | 0 | 0 |
| | 2 | ZLI | 0 | 0 | 0 | 0 | 0 | 0 |
| IgG3 | 10 | SBA | 20 | 20 | 20 | 20 | 20 | 20 |
| | 20 | BS | 40 | 80 | 40 | 40 | 40 | 40 |
| | 2 | ZLI | 20 | 40 | 20 | 10 | 10 | 20 |
| IgG4 | 10 | SBA | 0 | 0 | 0 | 0 | 0 | 0 |
| | 20 | BS | 0 | 0 | 0 | 0 | 0 | 0 |
| | 2 | ZLI | 0 | 0 | 0 | 0 | 0 | 0 |

[a]SBA, Southern Biotechnology Associates (Birmingham, AL); BS, The Binding Site Ltd.; ZLI, Zymed Laboratories Inc. (San Francisco, CA)

TABLE 5

Complement lysis of melanoma cell lin SK-MEL-178 mediated by GM2 antibodies in sera from patients immunized with GM2-KLH plus QS-21

| Patient No. | Percentage of lysis[a] | | |
|---|---|---|---|
| | Pre vaccination serum with complement | Post vaccination serum with complement | Post vaccination serum without complement |
| 1 | 1.3 | 38.75 | 3.1 |
| 2 | 2.2 | 16.9 | 2.72 |
| 3 | 1.1 | 14.0 | 0.9 |
| 4 | 1.2 | 26.0 | 2.2 |
| 5 | 2.1 | 34.9 | 1.65 |
| 6 | 10.5 | 44.7 | 2.3 |

[a]Target cells were labeled with $^{51}$Cr and treated with 1:5 diluted anti sera.

Fourth Series of Experiments

Increasing doses of saponin fraction QS-21 were administered as immunological adjuvant in a Phase I trial with a constant dose of the melanoma ganglioside GM2 covalently attached to keyhole limpet hemocyanin (KLH). Twenty-eight patients with AJCC Stage III or Iv melanoma who were free of disease after surgery were treated with six vaccinations administered subcutaneously over a 5 month period. Local and systemic reactions were QS-21 dose related. Doses of 100 ug or less induced mild local tenderness and inflammation at vaccination sites lasting 2–4 days and occasional brief low grade fever and malaise, but no significant incapacitation. The 200 ug dose induced low grade fever and malaise after 30% of vaccinations and local reactions as large as 20 cm in diameter were seen in all patients resulting in restricted usage of the injected extremity for 5-10 days. The titers of IgM and IgG antibodies against GM2, and IgG antibodies against KLH, were highest at the 100 and 200 ug QS-21 doses. No antibodies against QS-21 were detected. This trial identifies the 100 ug dose of QS-21 as the optimal well tolerated dose for induction of antibodies against GM2 and KLH in melanoma patients.

Introduction

Applicants and others have vaccinated melanoma patients with a series of whole melanoma cell vaccines selected for expression of a variety of glycoprotein and ganglioside antigens (1,2). The antigen recognized most frequently by antibodies in post vaccination sera was the ganglioside GM2. GM2 ganglioside is a Differentiation antigen overexpressed on the cell surface of human malignant melanomas. GM2 injected alone was found not to be immunogenic and so GM2 vaccines containing a variety of immunological adjuvants were tested (3,4) Immunization with purified GM2 ganglioside adherent to *Bacillus* Calmette-Guémerin (BCG) induced production of IgM antibody against GM2 in most melanoma patients and patients producing antibody had a longer disease-free interval and survival when compared to patients who did not produce antibody (4,5). In a randomized study with 122 melanoma patients who were disease free after surgery, the majority of patients (86%) receiving the GM2/BCG vaccine produced antibodies (6). Patients that produced anti-GM2 antibodies had a significantly longer disease free interval and overall survival than antibody negative patients. Comparing the two arms of the trial, patients receiving the GM2/BCG vaccine had an 18% improvement in disease free interval and an 11% improvement in survival when compared to the BCG control group, though neither difference was statistically significant. The immune response was of short duration, mostly IgM and of moderate titer. Similar approaches with other melanoma gangliosides GD2, GD3 and 9-0-acetyl GD3/BCG vaccines in patients resulted in only occasional low titer antibody responses (7). The need for a more effective vaccine was evident.

Landsteiner's classical experiments with hapten carrier conjugates had been successfully applied to vaccination against a variety of antigens including bacterial capsular polysaccharides in infants (8). Based on this background, several different carbohydrate tumor antigens were conjugated to keyhole limpet hemocyanin (KLH), and shown to elicit higher titer IgM and IgG antibody responses than previously seen with nonconjugate vaccines (9–11). Applicants tested the immunogenicity of GD3 linked to a variety of carrier molecules in the mouse and identified KLH as the optimal carrier (12). A GM2-KLH conjugate vaccine was tested alone or mixed with immunological adjuvants BCG and DETOX in melanoma patients but the immune response was not significantly different than that induced by GM2-BCG vaccines, moderate titer IgM antibodies alone were induced (13). A more potent immunological adjuvant was required.

QS-21 is a saponin fraction purified to near homogeneity from Quillaja saponaria Molina bark and selected for high adjuvant effect and low toxicity (14,15). Saponins have been used as immunological adjuvants in a variety of settings (reviewed in 15). QS-21 has been used to augment the antibody response against an *E. coli* polysaccharide (16), and the antibody and T cell responses against an HIV-1 envelope protein (17), ovalbumin (18), and feline leukemia virus (19). Cytotoxic T cells have been induced against HIV infected cells and ovalbumin transfected cells by immunization with protein/QS-21 mixtures (17,18). Applicants tested a variety of new immunological adjuvants with various carbohydrate antigen-KLH conjugate vaccines and the immunological adjuvants QS-21 and $SAF_m$ were found to most effectively augment IgM and IgG antibody titers (9). Experiments focused on QS-21 since it was the least toxic and was available for testing with conjugate vaccines. GD3 ganglioside-KLH plus QS-21 vaccines in the mouse induced consistent high titer IgM and IgG antibody responses (12), providing the basis for testing this approach in melanoma patients.

Described herein are the results of a Phase I trial using a constant dose of GM2-KLH plus increasing doses of QS-21. Since purified QS-21 or partially purified saponins such as Quil A had not previously been used in humans, the goal was to determine the maximum tolerated dose consistent with repeated outpatient administration and the optimal dose for augmenting the antibody response to GM2.

Materials and Methods

Gangliosides

GM2 and GD1b from bovine brain, were a gift from Fidia Research Laboratory (Abano Terme, Italy). GM3, GM1 and GD1a from bovine brain were purchased from Sigma Chemical Co. (St. Louis, Mo.). GD2 was made from GD1b by treatment with P-galactosidase (20). GD3 was isolated from bovine buttermilk and kindly provided by Dr. R. K. Yu (Medical College of Virginia, Richmond, Va.).

Reagents and Monoclonal Antibodies

HPTLC silica gel plates were obtained from E. Merck (Darmstadt, Germany); 4-chloro-1-naphthol, p-nitrophenyl phosphate disodium from Sigma. Alkaline phosphatase-conjugated goat anti-human IgM (Kierkegaard and Perry Labs, Gaithersburg, Md.) and mouse anti-human IgG-purified (Southern Biotech, Birmingham, Ala.) followed by alkaline phosphatase-conjugated goat anti-mouse IgG (Southern Biotech) were used-for ELISA. Horseradish peroxidase-conjugated goat anti-human IgM or IgG purchased from TAGO (Burlingame, Calif.) were used for dot blot immune stain and immune thin layer chromatography. Rabbit anti-mouse immunoglobulins conjugated to horseradish peroxidase for ITLC, and rabbit anti-mouse IgM and IgG conjugated to alkaline phosphatase for ELISA were used with control monoclonal antibodies, and were obtained from Zymed (San Francisco, Calif.). Anti-GM2 mAb 696 was obtained from Kyowa Hakko Kogyo (Tokyo, Japan) and anti-GD3 mAb R24 was generated (21).

Patients

Melanoma patients with AJCC Stage III or IV disease were considered eligible if all evidence of metastatic disease had been rejected within the last 8 months. None of the patients had received prior chemotherapy or radiation therapy. Patients were evaluated for toxicity at the time of each vaccination. In addition, patients were instructed to measure local reactions and to take their temperature. These results were called in and then reviewed at the next clinic visit. Four patients (one at each of the 4 dose levels) received only 4 immunizations due to disease progression necessitating other treatment.

Vaccine Preparation and Administration

GM2-KLH conjugate was prepared by Biomira Inc. (Edmonton, Alberta). The GM2/KLH molar ratio was approximately 800/1 and was supplied at a concentration of 0.57 mg conjugate per 0.5 ml normal saline. This represented one patient dose and contained 70 ug GM2, 500 ug KLH and 0.5 ml normal saline. QS-21 adjuvant, containing a saponin component isolated from Quillaja saponaria Molina tree bark, was provided by Cambridge Biotech Corp. (Worcester, Mass.). The purity of the QS-21 was determined to be ≧98% by analytical reverse phase HPLC. Ten, 50, 100 or 200 ug of QS-21 were diluted in 0.25 ml normal saline and mixed with GM2-KLH. The vaccine (final volume 0.75 ml) was vortexed for 2-3 minutes and administered within 15 min. Four vaccinations were administered subcutaneously at two week intervals followed by two more at eight week intervals. Initially. 12 patients were treated 3 at each of the 4QS-21 doses. Subsequently 1 additional patient was treated at the 10 ug dose and 3 additional patients were treated at the 3 higher doses. Cyclophosphamide (Cytoxan, Mead Johnson and Co., Evansville, Ind.) 200 mg/$N^2$, was administered IV to all patients 3-6 days prior to the first vaccination.

Serological and Delayed-type Hypersensitivity (DTH) Assays

Enzyme-linked Immunosorbent Assays (ELISA) were performed as previously described for gangliosides (5). For ELISA assays on QS-21, QS-21:ethylenediamine (prepared by linkage of ethylene diamine to the QS-21 glucuronic acid carboxyl group) was plated on glutaraldehyde treated Immulon 4 plates (Dynatech Labs, Chantilly, Va.). To control nonspecific "stickiness", immune sera were also tested on plates which were processed identically but to which no ganglioside KLH or QS-21 had been added, and the reading was subtracted from the value obtained in the presence of antigen. The titer was defined as the highest dilution yielding a corrected absorbance of 0.1 or greater. Immunostaining of gangliosides with monoclonal antibodies or human sera was performed after spotting on nitrocellulose strips as previously described (22). Patients were skin tested with GM2, GM2-HSA and KLH at the time of the fifth vaccination. Twenty-five micrograms of each were diluted in 0.05 ml PBS and administered intradermally. Results were interpreted as described previously (5).

Results

Toxicity

The number of vaccinations administered containing GM2-KLH alone or with various doses of QS-21 and the local and systemic reactions associated with these vaccinations is shown in Table 6. While GM2-KLH alone or with 10 ug of QS-21 resulted in occasional mild local erythema and induration, increasing doses of QS-21-resulted in increasing frequency and severity of local reactions. At the 10 and 50 ug doses, this was associated with slight tenderness and 2-4 cm of erythema and induration lasting 24-48 hours (no toxicity greater than grade 1 was detected). At the higher doses these reactions became more prominent with most reactions as large as 8-10 cm and some (at the 200 ug dose) extending to 20 cm in diameter. These reactions generally lasted 2-4 days and in one case as long as 7 days at the 100 ug dose, and generally lasted 7 days and in one case as long as 10 days at the 200 ug dose. In no case were analgesics more potent than tylenol required and patients at the 10, 50 and 100 ug doses continued to pursue their normal activities. Use of the vaccinated extremity was restricted for 5-8 days after administration of the majority of vaccines containing 200 ug QS-21, but all evidence of local reactions had disappeared by two weeks when the patients were next examined. No ulceration and drainage or subcutaneous nodules (as seen with most other adjuvants) were detectable. While occasional brief, mild, low grade fevers or myalgias were seen after vaccinations containing the lower 3 doses of QS-21, approximately one third of the vaccinations containing 200 ug of QS-21 were associated with these symptoms. In general, systemic symptoms were most prominent after the second immunization. All patients in the 200 ug QS-21 group were tapered to 100 ug or 50 ug QS-21 for their third and fourth immunizations due to concern over the increasing local and systemic reactions (side effects for these tapered dose immunizations are listed under 100 ug and 50 ug in Table 6). These doses were well tolerated and so all 5 patients (one patient had disease progression and was taken off protocol after 4 immunizations) were increased back to 200 ug for the fifth immunization. Two of the five fifth immunizations were associated with fever and flu-like symptoms, one of these was also associated with 20 cm of local erythema and induration. This patient's QS-21 dose was decreased to 100 ug in the sixth vaccination, no systemic symptoms developed and the local reaction was mild (3-4 cm erythema and induration). None of the four remaining sixth immunizations with 200 ug QS-21 were associated with systemic symptoms. While overall the systemic symptoms were quite mild, the local erythema, induration and tenderness were prominent enough with the 200 ug dose that applicants chose not to proceed with higher doses of QS-21.

Antibody Response Against GM2 after Vaccinations (see Table 7)

Immunization with GM2-KLH alone resulted in antibody titers quite similar to those seen in previous studies with vaccines containing GM2 adherent to the surface of BCG. Five of 6 patients produced IgM antibody, only 1 patient produced IgG antibody (of low titer). The IgM antibody titers increased with increasing doses of QS-21. Reciprocal median IgM antibody titer after immunization with GM2-KLH alone was 80, after 10 or 50 ug of QS-21 was 480 and 240 (respectively), and after 100 or 200 ug of QS-21 was 1280. IgG antibody titers increased progressively with increasing doses as well, from 0 in patients receiving GM2-KLH alone to 10, 60, 200 and 640 in patients receiving 10, 50, 100 and 200 ug of QS-21 respectively. Prominent IgM and detectable IgG antibodies (by ELISA and dot blot immune stains) were seen in every patient receiving GM2-KLH plus 95-21 Sequential IgM and IgG antibody titers for the groups of six patients receiving the 100 and 200 ug QS-21 doses ar shown in FIG. 9. Overall, th antibody response is quit similar in the two groups though IgG ELISA titers were slightly higher with the 200 ug dose. Dot blot immune stains against GM2 confirmed the specificity for GM2 and the similarity of reactions at the 100 and 200 ug doses (see Table 7 and FIG. 10). The median IgM dot blot reaction against GM2 increased from 2+in patients receiving GM2-KLH alone to between 2+ and 3+ in patients receiving 10 or 50 ug of QS-21 to 3+ in patients receiving 100 or 200 ug of QS-21. IgG reactions increased from 0 in patients receiving no QS-21 to 2+ in patients receiving 10 or 50 ug QS-21, to 3+ in patients receiving 100 or 200 ug QS-21.

Specificity Analysis of GM2 Antibody Responses

Dot blot immune stains with sera obtained prior to and after immunizations for 2 representative patients in each of the 5 treatment groups are shown in FIG. 10. Prior to immunization, IgM reactivity against GM1 was demonstrated in sera of many patients as applicants have previously described, but no reactivity was detected against GM2 or other gangliosides. Following immunization the GM1 reactivity was not effected but IgM and IgG antibodies against GM2 were seen in all patients. As applicants have previously described (13), these induced GM2 antibodies sometimes showed cross-reactivity with GD2 (patient 1, 100 ug dose).

Serological Responses Against KLH and OS-21

As shown in Table 7, reactivity against KLH was not seen prior to immunization and increased progressively with increasing=doses of QS-21. While the 50, 100 and 2 ug doses of QS-21 induced significantly higher titers of ISG antibodies against KLH than the 0 or 10 ug dose, there was no significant difference between the serological titers induced at th 50, 100 and 200 ug doses. Antibody titers to QS-21 were assayed by ELISA after four immunizations. There was no significant increase in antibody to QS-21 between pre-and post-immunization serum samples (data not shown).

DTH Responses to GM2 and KLH

No erythema or induration were detected at GM2 or GM2-HSA skin test sites. Prominent erythematous reactions were detected at 24 and 48 hours at most KLH skin test sites and these reactions were largest in patients receiving the 200 ug dose (median diameters 4.0 by 6.0 cm). These were associated with only minimal induration, suggesting a combination DTH and antibody mediated reaction, making precise quantification of the DTH response (by patients at home) difficult. Further Clinical Trials Utilizing the same dose of vaccine as above (Biomira, Inc.) six patients with advanced disease were treated. An additional six patients with advanced disease were treated with 1/10 the GM2-KLH dose again with 100 µg QS-21. Antibody titers in both groups were lower than seen in patients with early disease but the 7 µg GM2 dose appeared equally as effective at inducing IgM and IgG antibody titers as the 70 µg dose.

In another study, 6 patients with early disease were treated with a GM2-KLH construct. IgG antibody titers were comparable to those seen after administration of the Biomira construct though the IgM antibody titers appeared somewhat lower. However, all patients made antibody following immunization and the vaccine was well tolerated.

A further study will involve 18 patients receiving vaccinations of GM2-KLH, initially at weekly intervals (a schedule shown to be superior in mouse studies). The patients are randomized, some receiving no pretreatment with low dose cyclophosphamide, and the others receiving pretreatment with low dose cyclophosphamide. At this time 10 patients have been accrued and there appears to be no difference between patients receiving cyclophosphamide and those not receiving cyclophosphamide, and the antibody titers with the new schedule appear at this time to be superior to those in previous trials with the same conjugate.

Discussion

This was a Phase I trial designed to identify the maximum tolerated dose (MTD) of QS-21 for use in the outpatient setting and the dose of QS-21 providing the greatest immune potentiating effect. The probable MTD was identified as 200 ug QS-21 per vaccination. While the low grade fevers and malaise, and the large local inflammatory reactions at the 200 ug dose, cannot be considered the MTD in the context of high dose IL2 or combination chemotherapy as utilized in hospitalized patients with advanced melanoma (23,24), they were significant in the context of outpatient treatment of cancer patients in the adjuvant setting, and would be unacceptable for immunization against infectious diseases in normal recipients. The 100 ug dose, however, resulted in only 2 episodes of low grade fever in 44 injections and the local inflammatory responses did not interfere with daily activities and were generally limited to 2–4 days. This dose was well tolerated in the patient population of the clinical trial. There was a clear increase in local and systemic toxicity with progression from the 100 ug dose to 200 ug which made us hesitant to continue dose escalations. While fever and malaise at the highest dose were similar to those sometimes seen with other immunological adjuvants such as BCG and DETOX (15,25), local reactions were quite different. The 200 ug dose of QS-21 injected subcutaneously resulted in a 10–20 centimeter diameter area of erythema and induration which was hot and tender to the touch. This local response is more diffuse than the response generally seen with doses of DETOX or BCG inducing comparable systemic symptoms. A surprising feature of these responses was that several days later (or at most 10 days later) these reactions had completely abated and there was no evidence that the vaccination had been administered to that sight. No ulceration, drainage or nodule formation at the injection sight was detected in any patient.

A second surprising finding in this study was that QS-21 at any of the doses used resulted in a qualitatively different immune response to GM2 ganglioside. Even at the 10 ug dose all patients produced IgG antibodies detectable by dot blot immune stains against GM2. GM2-KLH vaccines alone or with optimal doses of BCG or DETOX, or GM2 adherent to the surface of BCG, salmonella Minnesota mutant R595 or proteosomes, had only rarely resulted in more than 1 detectable IgG response per 6 immunized patients (2,4,5). IgM and IgG antibody titers against GM2 continued to increase with increasing doses of QS-21 but appeared to reach a plateau between the 100 and 200 ug dose. IgG antibodies against KLH likewise increased with increasing doses of QS-21. Peak IgG titers were significantly higher at the 50, 100 and 200 ug doses than at the 0 or 10 ug doses, but the titers at the three higher doses were not significantly different from each other. Results demonstrate that the 100 and 200 ug doses of QS-21 induce the optimal antibody response against GM2 and that th 100 ug dose is better tolerated. The primarily erythematous skin test responses against KLH in patients immunized with GM2-KLH alone or GM2-KLH plus various doses of QS-21 was unexpected. It may represent a combination of antibody mediated arthus-like and DTH responses. It is also possible that the lower dose of KLH in the skin tests than that used in studies by others (26) (25 ug as opposed to 100 ug) was insufficient to produce a strong detectable DTH reaction, or that the high epitope density of GM2 ganglioside on the KLH in the vaccines did not permit the normal antigen processing and presentation required for induction of a classical DTH response against KLH.

Despite the wide spread use of QS-21 and other saponin containing adjuvants in experimental animals and veterinary practice (14–19), their mechanism of action remains unknown. It is possible to make some inferences on the mechanism of action of QS-21 from these studies. The lack of palpable nodules at injection sights suggest that a depo effect with granuloma formation does not occur. Despite the potency of QS-21 as an adjuvant, it appears to be a poor immunogen. Even after repeated immunizations, no detectable antibody responses resulted. So unlike other adjuvants such as C parvum, BCG and complete Freund's adjuvant, the immunogenicity of QS-21 may not contribute to its adjuvant effect. Low grade fever and malaise seen at the 200 ug dose, and diffuse erythema and induration at injection sights, suggest that cytokine release is involved. Intradermal injection of IL-2 has resulted in very similar reactions which on biopsy are characteristic of classical DTH responses (27,28). Partial switching of GM2 antibodies to an IgG response suggests induction of T cell help, perhaps as a consequence of this cytokine induction.

Applicants have recently demonstrated the superiority of KLH over other carriers tested for augmentation of ganglioside immunogenicity (12) and applicants demonstrate here the optimal dose of QS-21 for further augmentation of this effect. As applicants prepare for a large phase III trial of ganglioside vaccine in AJCC stage III melanoma patients, there are a number of variables which remain to be tested. Applicants are currently conducting preclinical studies with this ganglioside-KLH plus QS-21 vaccine plus the use of several other immunological adjuvants. In addition, clinical trials with different schedules of immunization and different doses of GM2-KLH are planned. The surprising findings in the phase I trial described here are 1) no evidence of granuloma formation was detected at any dose of QS-21 and 2) that at the well tolerated dose of 100 ug, the serological response against GM2 was strikingly superior, quantitatively and qualitatively, to any seen with previously tested GM2 vaccines.

TABLE 6

NUMBER OF ADVERSE REACTIONS OCCURRING (AND THEIR SEVERITY) AT EACH QS-21 DOSE IN PATIENTS RECEIVING VACCINES CONTAINING 500 UG GM2-KLH ± QS-21

|  | Dose of QS-21 and Adverse Reactions | | | | |
| --- | --- | --- | --- | --- | --- |
|  | 0 | 10 ug | 50 ug | 100 ug | 200 ug |
| Number of Vaccinations | 35 | 22 | 34 | 44 | 23 |
| ADVERSE REACTIONS: | | | | | |
| Local | | | | | |
| Tenderness and Pain | 6(1) | 7(1)* | 21(1) | 34(2) | 23(2) |
| Erythema and Induration | 6(1) | 4(1) | 17(1) | 24(2) | 21(3) |
| Systemic | | | | | |
| Fever | 0 | 0 | 3(1) | 2(1) | 7(1) |
| Headache | 0 | 0 | 0 | 0 | 1(1) |
| Myalgia | 0 | 1(1) | 2(1) | 0 | 6(1) |
| Nausea or Vomiting | 0 | 1(1) | 1(1) | 0 | 1(1) |

*7(1): Local pain or tenderness was experienced after 7 of 22 vaccinations containing 10 ug QS-21. The number in parenthesis indicates median severity by the NCI Common Toxicity Criteria, in this case mild local tenderness. For local toxicity, (1) Minimal tenderness and erythema, (2) Moderate erythema and induration <10 cm, pain not requiring narcotic analgesics, (3) Erythema and induration ≧10 cm, pain requiring narcotic analgesics (not seen). For systemic toxicity, (1) refers to temperatures 101°–103° F., mild headaches, mild muscle aches or mild nausea with no vomiting.

TABLE 7

SEROLOGIC RESPONSE AFTER VACCINATION WITH GM2-KLH PLUS VARIOUS DOSES OF QS-21

| | | PEAK ELISA TITER AGAINST GM2 | | | |
| --- | --- | --- | --- | --- | --- |
| VACCINE | # OF | Pretreatment | | After Treatment | |
| GM2-KLH PLUS | PATIENTS | IgM | IgG | IgM | IgG |
| No adjuvant | 6 | 20, 0(5)* | 0(6) | 160(2), 80(2), 40, 0 | 40, 0(5) |
| 10 µg QS-21 | 4 | 0(4) | 0(4) | 1280, 640, 320, 80 | 80, 20, 0(2) |
| 50 µg QS-21 | 6 | 20, 0(5) | 0(6) | 640, 320(2), 160(3) | 80(3), 40(2), 20 |
| 100 µg QS-21 | 6 | 40, 0(5) | 0(6) | 5120, 1280(3), 160, 80 | 2560, 640, 320, 80, 40(2) |
| 200 µg QS-21 | 6 | 320, 20, 0(4) | 0(6) | 5120, 1280(3), 320(2) | 1280(2), 640(2), 320, 80 |

TABLE 7-continued

SEROLOGIC RESPONSE AFTER VACCINATION WITH
GM2-KLH PLUS VARIOUS DOSES OF QS-21

| VACCINE<br>GM2-KLH PLUS | # OF<br>PATIENTS | PEAK DOT BLOT IMMUNE SYSTEM RESPONSE AGAINST GM2 | | IgG ELISA TITER AGAINST KLH | |
|---|---|---|---|---|---|
| | | IgM | IgG | Pretreatment | After Tr atm nt |
| No adjuvant | 6 | 3+, 2+(3), 1+, 0 | 1+(2), 0(4) | 0(6) | 360, 180(3), 20(2) |
| 10 μg QS-21 | 4 | 3+(2), 2+(2) | 2+(3), 1+ | 0(4) | 810, 270(2), 90 |
| 50 μg QS-21 | 6 | 3+(3), 2+(3) | 3+(2), 2+(2), 1+(2) | 0(6) | 2430(3), 810(2), 90 |
| 100 μg QS-21 | 6 | 3+(5), 2+ | 3+(4), 2+(2) | 0(6) | 21, 870, 2430(3), 810(2) |
| 200 μg QS-21 | 6 | 3+(4), 2+(2) | 3+(4), 2+(2) | 0(6) | 21, 870, 7290(3), 2430, 810 |

*One patient had a pretreatment peak titer ELISA response of 1/20. The number in parenthesis indicates the number of patients with a given response. In this cas, five patients had no detectable GM2 antibodies.

Fifth Series of Experiments

Introduction

The incidence of malignant melanoma has increased rapidly over the last decade. In 1992, over 32,000 individuals in the United States developed melanoma, and 6,700 deaths from melanoma were recorded (1). Following adequate resection of primary melanoma the five-year survival rate ranges from greater than 95% for patients with primary tumors of $\leq 0.75$ mm thickness to 50% for those with primary tumors of >4.0 mm thickness (2). Patients with regional lymph node metastases (AJCC Stage III), have a 5 year survival of 25–35% after elective or therapeutic dissection (3). No adjuvant therapy has been shown to reduce the rate of recurrence and increase survival after surgery in these patients. A large variety of agents have been tested in these adjuvant trials (reviewed in refs. 4, 5) including chemotherapy, nonspecific immune stimulators, interferons, and various types of melanoma vaccines. With regard to melanoma vaccines, the challenge has been to develop methods that can monitor immunogenicity of the vaccines in terms of strength and specificity of the resulting immune response. Because humoral immune reactions to vaccines can be quantitated and analyzed with a precision that is only now becoming possible with cellular immune reactions, applicants have focused on melanoma antigens that elicit humoral immunity. Of these serologically defined antigens, gangliosides, particularly GM2, have emerged as attractive targets for active immunization (5–8). Applicants have recently shown that immunization with purified GM2 adherent to BCG, after pretreatment with low does Cy, resulted in the induction of IgM antibodies in a high percentage of melanoma patients (8,9). The GM2 antibody response showed a T-cell independent pattern, i.e., short duration, lack of an IgG response, and lack of a booster effect of repeated vaccinations. The induced antibodies were cytotoxic for GM2-expressing melanoma cells in the presence of human complement, and patients that produced GM2 antibodies after immunization showed significantly longer disease-free interval and survival than patients that did not (9). The purpose of the present study was to confirm the beneficial effects of vaccine-induced GM2 antibody production in a randomized controlled trial.

Materials and Methods

Patients

Patients with pathologically documented melanoma metastases restricted to regional skin and lymph nodes (AJCC Stage III) were eligible for a period of 2 weeks to 13 weeks after complete resection of skin metastases or regional lymph nodes. Other eligibility criteria included: age >15 years; Karnofsky performance status $\geq 90$; serum creatinine <2.5 mg/dl, serum bilirubin <2.5 mg/dl; no other cancers; no chemotherapy or radiation therapy during the 8 week period preceding vaccination. Pregnant women were excluded. All patients were examined, and eligibility determined, within two weeks prior to randomization. Subsequent clinical follow-up was performed by the patient's primary oncologist.

Randomization and Follow-up

Informed consent was obtained from all patients and they were stratified by number of positive lymph nodes (1, 2–4, $\geq 5$), presence of intransit disease, and interval between surgery and vaccination (2–6 weeks, 7–13 weeks) Patients were randomized by computer (with adaptive allocation of block sizes to ensure reasonably even numbers in the two arms) to be vaccinated with GM2/BCG or with BCG alone. Neither patients nor medical personnel were informed of the type of vaccine administered until two weeks after the final vaccination. Follow-up information on all patients was obtained over a one-week period every 4–6 months by telephoning their primary physicians. Dates of recurrence documented radiographically or pathologically were used for determining disease-free interval. Since the two nonspecific components of this vaccination approach, BCG and low-dose cyclophosphamide, may have demonstratable antitumor activity (10,11,12), they were considered more appropriate than no treatment for the control arm.

GM2/BCG Vaccine

The ganglioside GM2 used for vaccine production was obtained from two sources, brain tissue from cats with Tay-Sachs disease (transmitted in these cats as an autosomal recessive trait), and GM1 prepared from brains of domestic cows and purchased from Supelco, Bellefonte, Pa. Slices of Tay-Sachs cat brain (provided by Dr. Mario Ratazzi, Mt. Sinai Hospital, New York, N.Y.) were extracted with chloroform/methanol, and the extract was peracetylated, subjected to florisil chromatography to remove phospholipids, deacetylated, dialyzed and subjected to DEAE-Sephadex column chromatography (13). After dialysis, GM2, the major fraction, was separated by preparative thin layer chromatography. GM2 was prepared from bovine brain GM1 by cleavage of the terminal galactose using β-galactosidase, as previously described (14). GM2 from the two sources was indistinguishable by thin layer chromatography (TLC) and immune TLC using murine monoclonal antibodies recognizing GM2 (13). Each batch of GM2 was more than 98% pure as defined by thin layer chromatography and densitometric scanning. Batches were tested by standard tests for sterility, and for safety in guinea pigs and mice.

Purified GM2 was dried and stored at 4° C. Tice strain BCG (University of Illinois, Chicago, Ill.), 107 viable units (or $3 \times 10^6$ viable units for use in patients with a positive PPD test) was suspended in distilled water by sonication together with 200 ug of dried purified GM2. The suspension was lyophilized and stored at −80° C. The residue was resuspended in 0.5 ml phosphate-buffered saline (PBS) shortly before vaccine administration. Under these conditions, GM2 has been found to adhere to BCG, presumably by hydrophobic bonds, as applicants have previously reported (8). BCG was suspended in PBS for use in the control group. All patients in the GM2/BCG group received 200 ug GM2 per vaccination. These vaccines and the vaccination protocol were approved by the Memorial Hospital Institutional Review Board and used under an IND with the U.S. Food and Drug Administration. The initial patients received GM2 of cat brain origin. Subsequently, an increasing proportion of GM1 derived GM2 was used because cat brain GM2 was no longer available. All patients received intradermal vaccine injections into 6–10 sites of an extremity with intact lymphatic drainage, and this was repeated twice at two-week intervals, using different extremities each time. Booster immunizations were administered two and five months after the initial series of vaccinations.

Cy Administration

A single dose of 200 mg/M² Cy (Cytoxan; Mead Johnson and Co., Evansville, Ind.) was administered intravenously to all patients five to seven days prior to the first and fourth vaccine injections.

Ganglioside Reagents

GD2 was prepared by treating GD1b with β-galactosidase (G. W. Jourdian, University of Michigan, Ann Arbor, Mich.) according to published methods (14). GM1 was purchased from Supelco (Bellefonte, Pa.). GD3 was a gift from Fidia Research Laboratories (Abano Terme, Italy), and GD1b was purchased from the same source. GM3 was purified from dog erythrocytes (13). GM2 for dot blot immune stains (FIG. 11) was prepared from GM1 by treatment with β-galactosidase or extracted from human melanoma biopsy specimens as previously described (13).

Serological Procedures

Sera were obtained at the time of each vaccination, 2 and 6' weeks after vaccines 3, 4 and 5, and 3 months after vaccine 5. The ELISA for GM2 or BCG antibodies (9) was performed with patient sera and rabbit anti-human IgM or anti-human IgG second antibody, or Protein A conjugated with alkaline phosphatase (Kirkegaard and Perry Labs, Gaithersburg, Md.). Readings obtained with normal sera from donors without GM2 reactivity were subtracted from readings obtained with the patients' sera. Antibody titer was defined as the highest serum dilution yielding a corrected absorbance of >0.10 as previously described (9). Dot blot immune stains were performed as previously described (8,9), and graded 0, 1+, 2+ or 3+ as shown in FIG. 11. Sera were categorized as positive if GM2 reactivity was 2+ or 3+ by dot blot with ELISA titer >1/20 or 1+ by dot blot with an ELISA titer $\geq 1/80$. Complement dependent cytotoxicity assays were performed previously described with normal human serum (diluted 1/3) as complement source and visual quantification of nonviable cells by Giemsa stain (8,15).

Skin Tests for Delayed-Type Hypersensitivity (DTH)

Unilamellar liposomes were prepared from egg phosphatidyl choline and passed through a 0.1 micron filter ten times. On the day of skin testing, (2 weeks after the fourth vaccination) 1.5 mg phosphatidyl choline liposomes and 25 ug GM2 were mixed in PBS and sonicated in a Branson 1200 water bath sonicator (Shelton, Conn.). Skin tests (0.1 ml volume) with a) 25 ug GM2 and b) 25 ug/1.5 mg GM2/liposomes were performed and read at 48 hours as previously described (16,17).

Results

Patient Characteristics

A total of 123 patients were enrolled between March 10, 1987 and Mar. 17, 1989. On review, one patient was found to have AJCC Stage II disease (no positive lymph nodes) and was therefore not included in the analysis. All 122 eligible patients, regardless of the number of vaccines received, are included as randomized in the analysis. Two patients (one in each group) decided to leave the study after one immunization because they found it too difficult to deal with the uncertainty of experimental therapy and randomization. One patient in the BCG group had received only two immunizations when disease progression was detected, and the treatment was discontinued. All other patients received at least the initial series of three immunizations and remained on protocol until its completion or until disease progression. One patient in the BCG group accidentally GM2/BCG in the fifth vaccination (the produced GM2 antibody and remained free of disease). The median follow-up is five years and three months, with a minimum follow-up of four years and three months after pre-randomization surgery.

The characteristics of the 122 randomized patients are shown in Table 8. The single most important prognostic indicator for patients with Stage III melanoma is the number of positive lymph nodes (3). Other factors associated with a poor prognosis include head and neck or trunk as the primary site, and intransit melanoma (3). The GM2/BCG and BCG groups were comparable with regard to these prognostic indicators.

TABLE 8

PATIENT CHARACTERISTICS

| CHARACTERISTIC | TREATMENT GROUP | | GM2 ANTIBODIES | |
|---|---|---|---|---|
| | BCG | GM2/BCG | Positive | Negativ |
| No. of Patients | 64 | 58 | 64 | 58 |
| Sex (M/F) | 48/16 | 37/21 | 48/16 | 37/21 |
| Median Age | 48.5 | 46 | 49.5 | 44 |
| (Range) | (27, 75) | (16, 74) | (31, 75) | (16, 74) |
| Time Since Surgery | | | | |
| 14–42 days | 21 | 22 | 20 | 23 |
| 43–91 days | 43 | 36 | 44 | 35 |
| Primary Site | | | | |
| Head and Neck | 7 | 7 | 8 | 6 |
| Trunk | 29 | 24 | 28 | 25 |
| Extremity | 23 | 17 | 21 | 19 |
| Not Detected | 5 | 10 | 7 | 8 |
| Depth of Primary | | | | |
| <2 mm | 15 | 12 | 15 | 12 |
| 2–4 mm | 20 | 15 | 19 | 16 |
| >4 mm | 10 | 11 | 10 | 11 |
| Not Available | 19 | 20 | 20 | 19 |
| Intransit Disease | | | | |
| Absent | 54 | 52 | 54 | 52 |
| Present | 10 | 6 | 10 | 6 |
| Number of Lymph Nodes with Metastases | | | | |
| 1 | 27 | 24 | 26 | 25 |
| 2–4 | 23 | 23 | 24 | 22 |
| >4 | 14 | 11 | 14 | 11 |

Side Effects

Pretreatment with Cy occasionally resulted in mild nausea or queasiness for 2–24 hours but was mostly well tolerated. Intradermal injection of BCG resulted in inflammation and eschar formation with drainage in all patients receiving three or more immunizations. To keep the inflammatory response at an acceptable level, the dose of BCG was decreased by a factor of 3 when eschar formation or drainage was first detected. Consequently, the median BCG dose at the time of the final immunization was $3 \times 10^6$ viable units in both treatment groups. The dose of $10^7$ units was maintained in only 10% of patients, and some patients required a further dose reduction to $10^6$ units. GM2 had no effect on the inflammatory response to BCG and caused no additional side effects.

Serological Response Against GM2

Sequential IgM anti-GM2 antibody titers before and after vaccination with GM2/BCG are shown in FIG. 10 for the first five patients treated (in 1987) and the last five patients treated (in 1989) who received the full series of GM2/BCG immunizations. As in a previous study (9), the antibody response was predominantly of the IgM type, and frequently showed an increase in titer after each immunization that resembled a repetitive primary response rather than an amnestic secondary response. Pre-immunization and peak titer post-immunization sera from all patients were also tested by dot blot immune stain to confirm the specificity of the antibodies detected by ELISA. Dot blot immune stains with the ten sera shown in FIG. 10 are shown in FIG. 11. Occasional low-titer pretreatment reactivity against GM1 was detected as previously described (8,9). Vaccine induced reactivity was restricted to GM2; no reactivity was seen with GM3, GD2, GD1b or GD3. GM2 antibodies were able to mediate complement dependent cytotoxicity in tests on GM2 expressing tumor cells with human complement (Table 9). No change in this pattern of antibody response and specificity was seen over the two year period of patient accrual. The results of serological analysis for all patients are summarized in Table 10. Seven of the 64 patients in the BCG arm were found to exhibit GM2 antibodies both by ELISA (median titer 1/40) and dot blot immune stain (median 2+). The antibodies were preexisting in 5 cases and were first detected after BCG vaccination in 2 cases. Titers of GM2 antibody increased 4-fold or more after BCG immunization in 3 of 5 patients with GM2 antibody prior to BCG vaccination. In contrast, only one of the 58 patients receiving GM2/BCG exhibited GM2 reactivity by both assays before immunization and 50 of 58 patients showed GM2 antibodies (median ELISA titer 1/160) in their serum after immunization, confirmed by dot blot immune stain (median titer 3+). The overall IgM anti-GM2 serologic response rate (2+ or 3+ dot blot and ELISA titer $\geq 1/20$ or 1+ by dot blot and ELISA titer $\geq 1/80$) in the two groups was 11% for BCG alone and 86% for GM2/BCG.

IgG antibodies were not detected in any patient's serum prior to immunization and were not induced in any patient by BCG immunization (Table 10). Vaccination with GM2/BCG induced a positive IgG antibody response in eight patients (median ELISA titer 1/80, median dot blot 2+). These responses were short-lived (median duration 8 weeks) and did not generally increase with additional immunizations. IgG reactivity in all cases was restricted to GM2 (data not shown). All eight patients also had IgM antibodies which were of higher titer and longer duration than IgG antibodies.

TABLE 9

COMPARISON OF GM2 ANTIBODY TITERS BEFORE AND AFTER IMMUNIZATION GM2/BCG, AS DETERMINED BY ELISA AND CYTOTOXICITY TESTS WITH HUMAN COMPLEMENT

| PATIENT | IgM ELISA TITER | O.D. AT 1/40 SERUM DILUTION | CYTOTOXICITY TITER* 20% LYSIS Endpoint | 50% LYSIS Endpoint |
|---|---|---|---|---|
| 6 | 20 | 0.05 | 20 | 0 |
|   | 160 | 0.412 | 20 | 0 |
| 7 | 0 | 0.066 | 5 | 0 |
|   | 80 | 0.134 | 80 | 5 |
| 8 | 0 | 0.017 | 0 | 0 |
|   | 320 | 0.78 | 80 | 5 |
| 10 | 10 | 0.057 | 0 | 0 |
|   | 160 | 0.455 | 80 | 20 |
| 12 | 0 | 0.011 | 5 | 0 |
|   | 160 | 0.506 | 320+ | 20 |
| 53 | 0 | 0.004 | 20 | 0 |
|   | 320+ | 0.896 | 320+ | 320 |
| 54 | 0 | 0.000 | 5 | 0 |
|   | 160 | 0.387 | 20 | 5 |
| 56 | 0 | 0.013 | 20 | 0 |
|   | 320 | 0.418 | 320 | 20 |
| 57 | 0 | 0.028 | 80 | 20 |
|   | 640 | 0.811 | 320 | 80 |
| 58 | 0 | 0.029 | 5 | 0 |
|   | 320 | 0.718 | 320 | 20 |

*Target cells: astrocytoma cell line SK-MG 6.

TABLE 10

GM2 ANTIBODIES IN THE SERUM OF MELANOMA PATIENTS BEFORE AND AFTER IMMUNIZATION WITH GM2/BCG, OR BCG VACCINES

| VACCINE | TOTAL NO. PATIENTS | NO. OF PATIENTS WITH ELISA TITER (RECIPROCAL) | | | | | | | NO. OF PATIENTS WITH DOT BLOT IMMUNE STAIN | | | |
|---|---|---|---|---|---|---|---|---|---|---|---|---|
| | | 0 | 10 | 20 | 40 | 80 | 160 | 320 | 640 | 0 | 1+ | 2+ | 3+ |
| IgM ANTIBODIES | | | | | | | | | | | | | |
| GM2/BCG | | | | | | | | | | | | | |
| BEFORE VACCINATION | 58 | 35 | 11 | 10 | 1 | | 1 | | | 56 | 1 | 1 | |
| AFTER VACCINATION | 58 | 2 | 3 | 2 | 8 | 8 | 15 | 9 | 11 | 7 | 4 | 15 | 32 |
| BCG | | | | | | | | | | | | | |
| BEFORE VACCINATION | 64 | 40 | 10 | 8 | 4 | | 2 | | | 57 | 2 | 5 | |
| AFTER VACCINATION | 64 | 26 | 11 | 14 | 7 | 4 | 1 | | 1 | 57 | 2 | 3 | 2 |
| IgG ANTIBODIES | | | | | | | | | | | | | |

TABLE 10-continued

GM2 ANTIBODIES IN THE SERUM OF MELANOMA PATIENTS BEFORE AND AFTER IMMUNIZATION WITH GM2/BCG, OR BCG VACCINES

| VACCINE | TOTAL NO. PATIENTS | NO. OF PATIENTS WITH ELISA TITER (RECIPROCAL) | | | | | | | | NO. OF PATIENTS WITH DOT BLOT IMMUNE STAIN | | | |
|---|---|---|---|---|---|---|---|---|---|---|---|---|---|
| | | 0 | 10 | 20 | 40 | 80 | 160 | 320 | 640 | 0 | 1+ | 2+ | 3+ |
| GM2/BCG | | | | | | | | | | | | | |
| BEFORE VACCINATION | 58 | 58 | | | | | | | | 58 | | | |
| AFTER VACCINATION | 58 | 48 | 3 | 1 | | 4 | 1 | | 1 | 47 | 4 | 5 | 2 |
| BCG | | | | | | | | | | | | | |
| BEFORE VACCINATION | 64 | 64 | | | | | | | | 64 | | | |
| AFTER VACCINATION | 64 | 64 | | | | | | | | 64 | | | |

DTH Response to GM2

Skin tests for DTH against GM2 and other antigens were performed after the initial series of three vaccinations. All patients receiving three or more immunizations developed strong DTH reactions to BCG. Eight patients (four vaccinated with BCG and four vaccinated with GM2/BCG) showed positive DTH reactions to GM2 and GM2 liposomes (used to keep GM2 at the skin test site) ranging from 10 to 33 mm of induration. Further tests revealed that these 8 patients showed similar reactivity with ganglioside free liposomes and with other gangliosides. Thus, there was no evidence for GM2 specific DTH in any patient.

Serologic Response Against BCG

Sera from all patients were tested for IgG ELISA reactivity against $10^3$ viable organisms/well BCG dried onto ELISA plates as described for gangliosides. No reactivity was seen before vaccination. Post-vaccination sera showed BCG antibody titers of 1/40–1/80 in both treatment groups, independent of whether or not the patients produced GM2 antibodies.

Correlation of Antibody Response and Immunization with Disease-Free Interval and Survival Comparison of disease-free interval and overall survival for all patients producing GM2 antibodies documented by two assays (ELISA titer of $\geq 1/180$ and dot blot 1+ or ELISA titer $\geq 1/20$ and dot blot $\geq 2+$) with those of patients who did not produce GM2 antibody is shown in FIG. 12. Significant differences were seen in both disease-free interval and overall survival (p=.004 and 0.02 respectively, by log rank test). Of the six patients who produced GM2 antibody prior to immunization (five receiving BCG and one receiving GM2/BCG), only one (a patient in the BCG group) developed recurrent disease, suggesting that the natural production of GM2 antibodies in patients with melanoma is associated with a favorable course. Conversely, of the eight patients who did not produce GM2 antibodies after vaccination with GM2/BCG, six developed recurrent melanoma and died, suggesting that failure to produce GM2 antibodies after vaccination indicates an unfavorable prognosis. Median BCG antibody titers in the six patients producing natural GM2 antibodies were the same as the titers in the eight GM2 antibody-negative patients in the GM2/BCG arm, indicating that these patients did not differ in their ability to mount a serologic response to an unrelated antigen.

When the six patients producing GM2 antibodies prior to randomization (five in the BCG arm and one in the GM2/BCG arm) were excluded from the analysis, disease-free interval of the GM2/BCG group was significantly longer than that of the BCG group (p=0.02 by logrank test), and a trend toward longer overall survival was also observed for the GM2/BCG group (FIG. 13). The curves plateau at 40–52 months, with differences of 23% and 14% in disease-free interval and overall survival, respectively. The small number of patients producing IgG antibodies reactive with GM2 after immunization makes it impossible to draw conclusion about the relative merits of IgM and IgG antibodies against GM2. Five of the eight patients positive for IgG GM2 antibodies remain free of disease at this time.

Comparison of the two treatment groups as randomized is shown in FIG. 14. The curves plateau at 40 to 52 months with a 18% difference in disease-free interval and 11% difference in overall survival in favor of vaccination with GM2/BCG. These differences were not statistically significant. Disease-free interval (30%) and overall survival (46%) rates at 51 months (the minimum period of follow-up) in the BCG group are similar to the rates applicants observed earlier in patients randomized to receive BCG or no treatment (28). As shown in FIG. 14, a beneficial effect of immunization was more evident when the two treatment groups were stratified for number of positive nodes (1 versus 2 or more). Immunization had less impact on disease free interval rates in patients with only one positive node. In contrast, the disease-free interval of patients with two or more positive nodes who received GM2/BCG was significantly longer than that of patients immunized with BCG alone (p=0.02 by logrank test). A similar trend was seen for survival (p=0.08 by logrank test).

Discussion

Applicants have made considerable efforts to develop ganglioside vaccines that induce high levels of serum antibodies (18,19) because 1) gangliosides are major cell surface constituents of melanoma cells (14,20–25), 2) human monoclonal antibodies with specificity for gangliosides can be isolated with relatively high frequency from patients with melanoma (14,25–28) and 3) human tumor cells expressing ganglioside antigens can be lysed by anti-ganglioside antibodies in the presence of human complement (13,29). GM2 ganglioside had been found particularly immunogenic in humans, and vaccines containing purified GM2 and BCG as adjuvant have been shown in elicit GM2 antibodies in melanoma patients pretreated with low dose cyclophosphamide (8,9). The study reported here was intended to answer two questions —does vaccination with a GM2/BCG vaccine induce production of GM2 antibodies in a high percentage of melanoma patients and does induction of GM2 antibodies alter the course of the disease in patients with Stage III melanoma after complete resection of all known tumor?

Regarding induction of GM2 antibodies, immunization with GM2/BCG was clearly effective in the majority of patients. Of 58 patients receiving the GM2/BCG vaccine, 50 produced GM2 antibodies detected in both ELISA and dot blot immune stain assays. As in earlier experience (9), the induced GM2 antibodies were mostly of the IgM class; IgG antibodies were detected less frequently. The correlation between GM2 antibody production and a more favorable clinical course (9) was also confirmed here and expanded in a more homogeneous population of disease-free AJCC Stage III melanoma patients. Patients producing GM2 antibody (whether naturally occurring or vaccine induced) had a significantly longer disease-free and overall survival than patients who showed no antibody response. Preexisting GM2 antibody (prior to vaccination) was seen in six patients in this series and appeared to be associated with an especially favorable prognosis. As the incidence of spontaneous GM2 antibody production appears to be similar (10%) in the general population and in melanoma patients (8,9), their relationship to melanoma development and growth remains unknown. It is of note that the titer of preexisting GM2 antibodies did not change over the nine-month follow-up period, whereas vaccine-induced GM2 antibodies generally remained detectable for only 8–12 weeks after immunization. This observation raises the possibility that persistence of antibody production may be important for a favorable clinical outcome and it indicates the need for developing GM2 vaccines that produce long lasting GM2 antibody responses. In contrast to vaccinated patients developing GM2 antibody, the 8 patients who did not produce GM2 antibody after immunization with GM2/BCG showed particularly rapid disease progression, recurrence being detected usually before the complete series of five immunizations was administered. Other prognostic factors were not less favorable in these patients, nor was their antibody response to BCG less vigorous than the response in GM2 antibody positive patients, indicating that general immunosuppression is not the underlying mechanism.

An association between GM2 antibody production and improved prognosis has also been suggested in studies of the antigen designated OFA-I (31), a cell surface antigenic system expressed by many melanomas. Several lines of evidence have indicated that antibody reactivity against OFA is primarily directed against GM2 ganglioside (30,25). Patients with increased IgM titers against OFA-I, either preexisting or after immunization with irradiated melanoma cells, showed prolonged survival (31).

While adding strength to the argument that GM2 antibodies are associated with a favorable prognosis in patients with melanoma, this study also illustrates the problems that emerge in designing randomized vaccine trials. Preexisting GM2 antibody production in 5 patients in the control group as opposed to 1 patient in the GM2/BCG group, and lack of a GM2 antibody response in 8 vaccinated patients in the GM2/BCG group contributed to a blunting of the distinction between the two randomized treatment groups to a point that the therapeutic gain in the GM2/BCG group was not significant. Clearly, patients with preexisting antibodies to GM2 need to be excluded or at least stratified in future studies. Equally important is the need to increase the immunogenicity of the vaccine. In this regard, applicants have explored approaches that have been successfully pursued in the context of carbohydrate vaccines against bacterial infections (reviewed in 32), including chemical modification of gangliosides to yield closely related congeners (33,34), ganglioside conjugation with immunogenic protein carriers (35), and use of more potent adjuvants (36). The approach applicants have found most effective has been to conjugate GM2 with keyhole limpet hemocyanin (KLH) and to administer the GM2-KLH conjugate with QS-21 (a saponin extract from Saponaria Quillaja) as adjuvant. In a pilot study in patients with melanoma, administration of this vaccine resulted in IgM GM2 antibody titers much higher than those seen after GM2/BCG and, even more important, consistent production of GM2 antibodies belonging to the IgG class, thus apparently converting a T-independent antibody response into a T-dependent response (37).

An additional approach to improving the clinical efficacy of the GM2/BCG vaccine described here would be incorporation of additional immunogenic melanoma gangliosides into the vaccine. Experiments in the mouse indicate that conjugation with KLH and use of QS-21 adjuvant also augments the immunogenicity of GD3 (35), a more highly expressed melanoma ganglioside that has so far shown very low immunogenicity in patients with melanoma. If these observations can be confirmed in human studies, applicants may have the basis for constructing a polyvalent ganglioside conjugate vaccine incorporating several major melanoma gangliosides and thus circumventing the heterogeneity of ganglioside expression seen in human melanomas. Applicants believe that the results of the study reported here justify further pursuit of this approach.

REFERENCES OF FIRST AND SECOND SERIES OF EXPERIMENTS

1. Apple, R. J., Domen, P. L., Muckerheide, A. & Michael, J. G. (1988). Cationization of Protein Antigens: IV Increased Antigen Uptake by Antigen Presenting Cells. *J. Immunol.* 40: 3290.
2. Berd, D., Mastrangelo, M. J., Engstrom, P. F., Paul, A. and Maguire, H. (1982) Augmentation of the human immune response by cyclophosphamide. *Cancer Res.* 42: 4862.
3. Borch, R. F., Bernstein, M. D. and Durst, H. D. (1971). The cyanohydridobroate anion as a selective reducing agent. *J. American. Chem. Soc.* 93:2897.
4. Cahan, L. D., Irie, R. F., Singh, R., Cassidenti, A., and Paulson, J. C. (1982) Identification of a Human Neuroectodermal Tumor Antigen (OFA-I-2) as ganglioside GD2. Proc. Natl. Acad. Sci. USA 79:7629.
5. Carubia, J. M., Yu, R. K., Macala, L. J., Kirkwood, J. M., Varga, J. M. (1984). Gangliosides of Normal and Neoplastic melanocytes. *Biochem. Biophs. Res. Comm.* 120: 500.
6. Chang, S. P. and Rittenberg, M. B. (1981). Immunologic memory to phosphorylcholine in vitro. I. Asymmetric expression of clonal dominance. *J. Immunol.* 126: 975.
7. Criegee R. (1957) The course of ozonization of unsaturated compounds. Record of Chemical Progress. 18: 111.
8. Donnelly, J. J., Deck, R. R., & Llu, M. A. (1991). Adjuvant activity of the outer membrane protein complex of *neisseria meningitidis* sergroup B for a polysaccharide-protein conjugate. Vaccines 91. Cold Spring Harbor Laboratory Press. 403.
9. Eilber, F. R., Morton, D. L., Holmes, E. C., Sparks, F. C. and Ramming, K. P. Adjuvant immunotherapy with BCG in treatment of regional-lymph-node metastases from malignant melanoma. *N. Engl. J. Med.* 194: 237–240, 1976.
10. Eskola, J., Kayrty H., Takaia, A. K., Peltola, H., Ronneberg, P. R. Kha, E., Pekkanen, E., McVerry, P. H. and Makela, P. H. (1990). A Randomized Prospective Field Trial of a Conjugate Vaccine in the Protection of Infants and Young Children Against Invasive *Haemophilus Influenza* Type b Disease. N. Engl. J. Med. 323: 1381.

11. Gray, G. R. (1974). The Direct Coupling of Oligosaccharides to Proteins and Derivatised Gel. *Arch. Biochem. Biophys. Acta.* 163: 426.
12. Gray, G. R. (1978). Antibodies to Carbohydrates: Preparation of Antigens by Coupling Carbohydrates to Proteins by Reductive Amination With cyanoborohydribe. *Methods Enzymol.* 50: 155.
13. Hakomori, S. I. (1985). Aberrant Glycosylation in Cancer Cell Membranes as Focused on Glycolipides: Overview and Perspective. *Cancer Res.* 45: 2405.
14. Hamilton, W. B., Hellins, F., Lloyd, K. C., Livingston, P. O. (1993). Gangliosides Expression on Human Malignant Melanoma Assessed by Quantitative Immune Thin Layer Chromatography. *Int. J. Cancer* 53: 1.
15. Hilal, E. Y., Pinsky, C. M., Hirshaut, Y., Wanebo, H. J., Hansen, J. A., Braun, D. W. Jr., Fortner, J. G., and Oettgen, H. F. (1981). Surgical adjuvant therapy of malignant melanoma with *Corynebacterium Parvum. Cancer* 48: 245.
16. Houghton, A. N., Mintzer, D., Cordon-Cardo, C., Welt, S., Fliegel, B., Vadhan, S., Carswell, E., Melamed, M. R., Oettgen, H. F. & Old, L. J. (1985). Mouse Monoclonal IgG3 Antibody Detecting GD3 Ganglioside: A Phase I trial in Patients with Malignant Melanoma. *Proc. Natl. Acad. Sci. USA* 82: 1242.
17. Itonori, S., Hidari, K., Sanai, Y., Taniguchi, M. & Nagai, Y. (1989). Involvement of the Acyl Chain of Ceramide in Carbohydrate Recognition by an Anti-glycolipid Monoclonal Antibody: The Case of an Anti-Melanoma Antibody, M2590, to GM3-Ganglioside. *Glycoconjugate J.* 6: 551.
18. Kanfer, J. N. & Hakomori, S. (1983). Sphingolipid Biochemistry. In: Hanahan, D. J. Handbook of Lipid Research. New York: Plenum Press.
19. Kensil, C. R., Patel, U., Lennick, M. and Marciani, D. (1991) Saponin adjuvants from Quillaja saponaria Molina. *J. Immunol.* 146: 431.
20. Kundu, S. K., Marcus, D. M. and Veh, R. W. (1980). Preparation and properties of antibodies to GD3 and GM1 gangliosides. *J. Neurochem.* 34: 184.
21. Landsteiner, K. & Chase, M. W. (1942). Experiments on Transfer of Cutaneous Sensitivity to Simple Compounds. *Proc. Soc. Exp. Biol. Med.,* 49, 688.
22. Livingston, P. O. (1989) The basis for ganglioside vaccines in melanoma. IN: Human Tumor Antigens and Specific Tumor Therapy, UCLA Symposia on Molecular and Cellular Biology, R. Metzgar and M. Mitchell (eds.), Alan R. Liss, Inc., New York, N.Y. Volume 99: 287.
23. Livingston, P. O. (1991). Active specific immunotherapy in the treatment of cancer. In: Oettgen, H. F. (Ed.) Immunolgy and Allergy Clinics of North America: Human Cancer Immunology II. London, U.K.: W.B. Saunders Co. Vol. II: 2, 402–423.
24. Livingston, P. O., Calves, M. J., Helling, F., Zollinger, W. O., Blake, M. S. and Lowell, G. H. (1993b). GD3/proteosome vaccine induce consistent IgM antibodies against the ganglioside GD3. *Vaccine.* In Press.
25. Livingston, P. O., Cunningham-Rundles, S., Marfleet, G., Gnecco, C., Wong, G. Y., Schiffman, C., Enker, W. E. and Hoffmann, M. K. (1987) Inhibition of suppressor cell activity by cyclophosphamide in patients with malignant melanoma. *J. Biol. Resp. Mod.* 6: 392.
26. Livingston, P. O., Natoli, E. J. Jr., Calves, M. J., Stockert, E., Oettgen, H. F. and Old, L. J. (1987). Vaccine containing purified GM2 ganglioside elicit GM2 antibodies in melanoma patients. *Proc. Natl. Acad. Sci. USA,* 84: 2911.
27. Livingston P. O., Ritter G. and Calves M. J. (1989) Antibody response after immunization with the ganglioside GM1, GM2, GD2 and GD3 in the mouse. *Cancer Immunol. Immunother.* 29: 179–184.
28. Livingston, P. O., Ritter, G. Srivastava, P., Padavan, M., Calves, M. J., Oettgen, H. F. and Old, L. J. (1989). Characterization of IgG and IgM antibodies induced in melanoma patients by immunization with purified GM2 ganglion. *Cancer Res.* 49: 7045.
29. Livingston, P. O., Watanabe, T., Shiku, H., Houghton, A. N., Albino, A., Takahashi, T., Resnick, L. A., Michitsch, R., Pinsky, C. M., Oettgen, H. F. and Old, L. J. (1982) Serological response of melanoma patients receiving melanoma cell vaccines: I. autologous cultured melanoma cells. *Int. J. Cancer* 30: 413–422.
30. Livingston, P. O., Wong, G. Y., Adluri, S., Tao, Y., Padavan, M., Parente, R., Hanlon, C., Calves, M. J., Helling, F., Ritter, G., Oettgen, H.F., & Old, L. J. (1993a) A Randomized Trial of Adjuvant Vaccination with BCG Versus BCG Plus the Melanoma Ganglioside GM2 in AJCC Stage III Melanoma Patients. In Preparation.
31. Longenecker, B. M., Willans, D. J., MacLean, G. D., et al. (1987). Monoclonal antibodies and synthetic tumor-associated glycoconjugates in the study of the expression of Thomsen-Friedenreich-like ant Tn-like antigens on human cancers. *JNCI* 78: 489.
32. Lowell, G. H., Ballou, W. R., Smith, L. F. Wirtz, R. A., Zollinger, W. D. & Hockmeyer, W. T. (1988). Proteosome-Lipopeptide Vaccines: Enhancement of Immunogenicity for malaria CS peptides. *Science* 240: 800.
33. Marciani, D. J., Kensil, C. R., Beltz, G. A., Hung, C. H., Cronier, J., and Aubert, A. Genetically engineered subunit vaccine against FeLV: protective immune response in cats. *Vaccine* 9: 89.
34. MacLean, G. D., Bowen-Yacyshyn, M. B., Samuel, J., Meikle, A., Stuart, G., Nation, J., Poppema, S., Jerry, M., Koganty, R., Wong, T. & Longenecker, B. M. (1992). Active Immunization of Human Ovarian Cancer Patients Against a Common Carcinoma (Thomsen-Friedenreich) determinant using a Synthetic Carbohydrate Antigen. *J. Immunotherapy* 11: 292.
35. Neuenhofer, S., Schwarzmann, G., Egge, H. & Sandhoff, K. (1985). Synthesis of Lysogangliosides. *Biochem.* 24: 525.
36. Nores, G., Dohi, T., Taniguchi, M. & Hakomori, S.-I. (1987). Density-Dependent Recognition of Cell Surface GM3 by a Certain Anti-Melanoma Antibody, and GM3 Lactone as a Possible Immunogen: Requirements for Tumor Associated Antigen and Immunogen. *J. Immunol.,* 139 IX: 3171.
37. Old, L. J. (1981). Cancer immunology: The search for specificity-G.H.A. Clowes Memorial Lecture. *Cancer Res.,* 41: 361.
38. Pappas, J. J., Keaveneiy, W. P., Gaucher, E., and Melvin, B (1966). A new and convenient method for converting olefins to aldehyde. *Tetrahedron Letters,* 36: 4273.
39. Ritter, G., Boosfeld, E., Adluri, R., Calves, M., Oettgen, H. F., Old, L. J. & Livingston, P. O. (1991). Antibody Response to Immunization with Ganglioside GD3 and GD3 Congeners (Lactones, Amide and Gangliosidol) in Patients with Malignant Melanoma. *Int. J. Cancer,* 48: 379.
40. Ritter, G., Boosfeld, E., Markstein, E., Yu, R. K., Ren, S., Oettgen, H. F., Old, L. J. and Livingston, P. O. (1990a). Biochemical and serological characteristics of natural 9-O-acetyl GD3 from human melanoma and bovine buttermilk and chemically O-acetylated GD3. *Cancer Res.* 50: 1403.

41. Ritter, G., Boosfeld, E., Calves, M. J., Oettgen, H. F., Old, L. J. and Livingston, P. O. (1990b). Antibody response after immunization with gangliosides GD3, GD3 lactones, GD3 amide and GD3 gangliosidol in the mouse. GD3 lactone I induces antibodies reactive with human melanoma. *Immunbiology* 182: 32.

42. Romball, G. C. and Weigle, W. O. (1984). T cell competence to heterologous and homologous thyroglobulins during the induction of experimental autoimmune thyroiditis. *Eur. J. Immunol.* 14: 887.

43. Roy, R. and Lafferiere, C. A. (1990) Michael Addition as the key step in the syntheses of Sialyloligosaccharide-Protein Conjugates from N-Acroloylated Glycopyranosylamines. *J. Chem. Soc. Chem. Commun.* 1709.

44. Svennerholm, L. (1957). Quantitative estimation of sialic acids-II. Colorimetric resorcinol-hydrochloric acid method. *Biochem. Biophys. Acta.* 24: 604.

45. Tam, J. P. (1988). Synthetic Peptide Vaccine Design: Synthesis and Properties of a High-Density Multiple Antigenic Peptide System. *Proc. Natl. Acad. Sci. USA*, 85: 5409.

46. Tam, J. P. & Lu, Y. (1989). Vaccine Engineering: Enhancement of Immunogenicity of Synthetic Peptide Vaccines Related to Hepatitis in Chemically Defined Models Consisting of T-and B-Cell Epitopes. *Proc. Natl. Acad. Sci. USA* 86: 9084.

47. Teale J. M. and Abraham K. M. (1987) The regulation of antibody class expression. *Immun. Today* 8: 122.

48. Tsuchida, T., Saxton, R. E., Morton, D. L. & Irie, R. F. (1987). Gangliosides of Human Melanoma. *J. Natl. Cancer Inst.* 78 I: 45.

49. Nicolai H., Muller H. E., Zilliken F. (1978) Substrate Specificity of Neuramimidase from *Erysipelothrix rhusiopathiae*. Hoppe-Seyler's *Z. Physiol. Chem.* 359: 393.

50. Wiegandt, H. & Baschang, G. (1965). Die Gewinnung des Zuckeranteils der Glykosphingolipde durch ozonolyse and Fragmentierung Z. Naturtors Chung, 20b; 164.

51. Weight, W. O. (1977) Autoimmunity: Genetic, Immunologic, Virologic and Clinical Aspects. New York, Academic: 141.

52. Yamaguchi, H., Furukawa, K., Fortunato, S., Livingston, P. O., Lloyd, K. O., Oettgen, H. F. & Old, L. J. (1987) Cell-surface Antigens of Melanoma Recognized by Human Monoclonal Antibodies. *Proc. Natl. Acad. Sci. USA* 84: 2416.

REFERENCES OF THE THIRD SERIES OF EXPERIMENTS

1. Hakomori, S. I. 1985. Abberant glycosylation in cancer cell membranes as focused on glycolipides: Overview and perspectives. Cancer Res. 45:2405.

2. Carubia, J. M., R. K. Yu, L. J. Mascala, J. M. Kirkwood, and J. M. Varga. 1984. Gangliosides on normal and Neoplastic melanocytes. Biochem. Biophys. Res. Comm. 120: 500.

3. Hamilton, W. B., F. Helling, K. O. Lloyd, and P. O. Livingston. 1993. Ganglioside expression on human malignant melanoma assessed by quantitative immune thin layer chromatography. Int. J. Cancer. 53:1.

4. Tsuchida, T., R. E. Saxton, D. L. Morton, and R. F. Irie. 1987. Gangliosides of human melanoma. J. Natl. Cancer Inst. 78 I: 45.

5. Livingston, P. O., E. J. Jr. Natoli, M. J. Calves, E. Stockert, H. F. Oettgen, and L. J. Old. 1987. Vaccines containing purified GM2 ganglioside elicit GM2 antibodies in melanoma patients Proc. Natl. Acad. Sci. USA 84: 2911.

6. Livingston, P. O., G. Ritter, P. Srivastava, M. J. Calves, H. F. Oettgen, and L. J. Old. 1989. Characterisation of IgG and IgM antibodies induced in melanoma patients by immunization with purified GM2 ganglioside. Cancer Res. 49:7045.

7. Livingston, P. O., G. Y. Wong, S. Adluri, Y. Tao, M. Padavan, R. Parente, C. Hanlon, M. J. Calves, F. Helling, G. Ritter, H. F. Oettgen, and L. J. Old. 1994. Improved survival in AJCC Stage III melanoma patients with GM2 antibodies: A randomized trial of adjuvant vaccination with GM2 ganglioside. J. Clin. Oncol. in press.

8. Livingston, P. O. 1989. The Basis for ganglioside vaccines in melanoma. In Human tumor antigens and specific tumor theraphy. vol. 99. R. Metzgar and M. Mitchell, eds. Alan R. Liss. Inc., New York, N.Y., p. 287.

9. Helling, F., A. Shang, M. J. Calves, S. Zhang, S. Ren, R. K. Yu, H. F. Oettgen, and P. O. Livingston. 1994. GD3 vaccines for melanoma: Superior immunogenicity of KLH conjugate vaccines. Cancer Res. in press.

10. Kensil, C. R., U. Patel, M. Lennick, and D. Marciani. 1991. Separation and characterization of saponins with adjuvant activity from Quillaja saponaria Molina Cortex. J. Immunol. 146:431.

11. Newman, M. J., J.-Y. Wu, B. H. Gardner, K. J. Murroe, D. Leombruno, J. Recchia, C. R. Kensil, and R. T. Coughlin. 1992. Saponin Adjuvant Induction of Ovalbumin-specific CD8+ Cytotoxic T-Lymphocyte Responses. J. Immunol. 148: 2357.

12. Cahan, L. D., R. F. Irie, R. Singh, A. Cassidenti, and J. C. Paulson. 1982. Identification of a neuroectodermal tumor antigen (OFA-I-2) as ganglioside GD2. Proc. Natl. Acad. Sci. USA 79:7629.

13. Dippold, W. G., K. O. Lloyd, L. T. Li, H. Ikeda, H. F. Oettgen, and L. J. Old. 1980. Cell surface antigens of human malignant melanoma: definition of six antigenic systems with monoclonal antibodies. Proc. Natl. Acad. Sci. USA. 77:6114.

14. Hawkes, R., E. Niday, and J. A. Gordon. 1982. Dotimunebinding assay for monoclonal and other antibodies. Anal. Biochem. 119: 142.

15. Basten, A., and J. G. Howard. 1973. Thymus independence. In Contemporary Topics in Immunobiology. A. J. S. Davies, ed. Plenum Press, New York, Vol. 2, p. 265.

16. Mosier, D. E., and A. J. Feeney. 1987. The physiology of B Lymphocytes capable of generating anti-polysaccharide antibody responses. In Towards Better Carbohydrate Vaccines. R. Bell, and G. Torrigiani, eds. J. Wiley & Sons Ltd, London, Great Britain, p. 243.

17. Jennings, H. J., F. E. Ashton, A. Gamian, F. Michon, and R. Roy. 1987. A chemically modified Group B meningococcal polysaccharide vaccine. In Towards Better Carbohydrate Vaccines. R. Bell, and G. Torrigiani, eds. J. Wiley & Sons Ltd, London, Great Britain, p. 11.

18. Schneerson, R., J. B. Robbins, S. C. Szu, and Y. Yang. 1987. Vaccines composed of polysaccharide-protein conjugates: current status, unanswered questions, and prospects for the future. In Towards Better Carbohydrate Vaccines. R. Bell, and G. Torrigiani, eds. J. Wiley & Sons Ltd, London, Great Britain, p. 307.

19. Geysen, H. M., R. Macfarlan, S. J. Rodda, G. Tribbick, T. J. Mason, and P. Schoofs. 1987. Peptides which mimic carbohydrate antigens. In Towards Better Carbohydrate Vaccines. R. Bell, and G. Torrigiani, eds. J. Wiley & Sons Ltd, London, Great Britain, p. 103.

20. Soederstroem, T. Anti-idiotypes as surrogate polysaccharide vaccines. 1987. In Towards Better Carbohydrate Vaccines. R. Bell, and G. Torrigiani, eds. J. Wiley & Sons Ltd, London, Great Britain, p. 119.

21. Landsteiner, K., and M. W. Chase. 1942. Experiments on transfer of cutaneous sensitivity to simple compounds. Proc. Soc. Exp. Biol. Med. 49: 688.
22. Avery, O. T., and W. F. Goebel. 1929. Chemo-immunological studies on conjugated carbohydrate-proteins. J. Exp. Med. 50: 533.
23. Schneerson R., O. A. Barrera, and J. B. Sutton. 1980, Preparation, characterization, and immunogenicity of *Haemophilus influenzae* type b polysaccharide protein conjugates. J. Exp. Med. 152:361.
24. Lepow, M. L., J. S. Samuelson, and L. K. Gordon. 1985. Safety and immunogenicity of *Haemophilus influenzae* type b-polysaccharide diphtheria toxoid conjugate vaccine in infants 9 to 15 months of age. J. Pediatr. 106:185.
25. Chu, C. Y., R. Schneerson, J. B. Robbins, and S. C. Rastogi. 1983. Further studies on the immunogenicity of *Haemophilus influenzae* type b and pneumococcical type 6A polysaccharide protein conjugates. Inf. Immun. 50: 245.
26. Marburg, S. D. Jorn, L. Tolman, B. Arison, J. McCauley, P. J. Kniskern, A. Hagopian, and P. P. Vella. Biomolecular chemistry of macromolecules: synthesis of bacterial polysaccharide conjugates with *Neisseria meningitidis* membrane protein. J. Am. Chem. Soc. 108: 5282.
27. Anderson, P. 1983. Antibody response to *Haemophilus influenzae* type b and diphtheria toxin induced by conjugates of oligosaccharides of the type b capsule with the nontoxic CRM 197. Inf. Immun., 39: 233.
28. Turner, R. B., C. O. Cimino, and B. J. Sullivan. 1991. Prospective comparison of the immune response of infants to three *Haemophilus influenzae* type b vaccines. Pediatr. Infect. Dis. J. 10: 108.
29. Anderson, P., M. E. Pichichero, and R. A. Insel. Immunogens consisting of Oligosaccharides from the capsule of *Haemophilus influenzae* type b coupled to diphtheria toxoid or CRM 197. J. Clin. Invest. 76: 52.
30. Weinberg, G. A., M. S. Einhorn, A. A. Lenoir, P. D. Granoff, and D. M. Granoff. 1987. Immunologic priming to capsular polysaccharide in infants immunized with *Haemophilus influenzae* type b polysaccharide-*Neisseria meningitidis* outer membrane protein conjugate vaccine. J. Pediatr. 118: 22.
31. Ritter, G., E. Boosfeld, R. Adluri, M. Calves, H. F. Oettgen, L. J. Old, and P. O. Livingston. 1991. Antibody response to immunization with ganglisoside GD3 and GD3 congeneres (lactones, amide and gangliosidol) in patients with malignant melanoma. Int. J. Cancer 48: 379.
32. Ritter, G., E. Boosfeld, M. J. Calves, H. F. Oettgen, L. J. Old, and P. O. Livingston. 1990. Biochemical and serological characteristics of natural 9-O-acetyl GD3 from human melanoma and bovine buttermilk and chemically O-acetylated GD3. Cancer Res. 50: 1403.
33. Chapman, P. B., and A. N. Houghton. 1991. Induction of IgG Antibodies against GD3 Ganglioside in Rabbits by an Anti-idiotypic Monoclonal Antibody. J. Clin. Invest. 88: 186.
34. Svennerholm, L. 1963. Chromatographic separation of human brain gangliosides. J. Neurochem. 10: 613.

REFERENCES OF THE FOURTH SERIES OF EXPERIMENTS

1. Livingston, P. O., Kaelin, K., Pinsky, C. M., Oettgen, H. F. and Old, L. J. The serological response of patients with stage II melanoma to allogeneic melanoma cell vaccines. Cancer 1985, 56, 2194–2200.
2. Livingston, P. O. Experimental and clinical studies with active specific immunotherapy. In: Immunity to Cancer II (Ed. Mitchell, M. S.) Alan R. Liss, Inc., New York, 1989, pp. 309–321.
3. Livingston, P. O., Jones-Calves, M. and Natoli, E. J. Jr. Approaches to augmenting the immunogenicity of the ganglioside GM2 in mice: Purified GM2 is superior to whole cells. J. Immunol. 1987, 138, 1524–1529.
4. Livingston, P. O., Natoli, E. J. Jr., Calves, N. J., Stockert, E., Oettgen, H. F. and Old, L. J. Vaccines containing purified GM2 ganglioside elicit GM2 antibodies in melanoma patients. Proc. Natl. Acad. Sci. USA 1987, 84, 2911–2915.
5. Livingston, P. O., Ritter, G., Srivastava, P., Calves, N. J., Oettgen, H. F. and Old, L. J. Characterization of IgG and IgM antibodies induced in melanoma patients by immunization with purified GM2 ganglioside. Cancer Res. 1989, 49, 7045–7050.
6. Livingson, P. O., Wong, G. Y. C., Adluri, S., Tao, Y., Padavan, M., Parente, R., Hanlon, C., Jones-Calves, M., Helling, F., Ritter, G., Oettgen, H. F. and Old, L. J. A randomized trial of adjuvant vaccination with GM2 ganglioside in patients with AJCC Stage III melanoma. J. Clin. Oncol. 1994, In Press.
7. Livingston, P. O. Experimental and clinical studies with active specific immunotherapy. In: Immunity to Cancer II (Ed. Mitchell, M. S.) Alan R. Liss Inc., New York, 1989, pp. 309–321.
8. Eskola, J., Kayrty, H., Takaia, A. K., Peltola, H., Ronneberg, P. R., Kha, E., Pekkanen, E., McVerry, P. H. and Makela, P. H. A randomized prospective field trial of a conjugate vaccine in the protection of infants and young children against invasive *Haemophilus Influenza* type b disease. N. Engl. J. Med. 1990, 323, 1381–1387.
9. Livingston, P. O., Koganty, R. R., Longenecker, B. M., Lloyd, K. O. and Calves, M. J. Studies on the immunogenicity of synthetic and natural Thomsen-Friedenreich (TF) antigens in mice: Augmentation of the response by Quil A and SAF-m adjuvants and analysis of the specificity of the responses. Vaccine Res. 1991, 1, 99–109.
10. MacLean, G. D., Bowen-Yacyshyn, M. B., Samuel, J., Meikle, A., Stuart, G., Nation, J., Poppema, S., Jerry, M., Koganty, R., Wong, T. and Longenecker, B. M. Active immunization of human ovarian cancer patients against a common carcinoma (Thomsen-Friedenreich) determinant using a synthetic carbohydrate antigen. J. Immunotherapy 1992, 11, 292–305.
11. G. D., Reddish M., Koganty R., Wong T., Gandhi, S., Smolenski, M., Samuel, J., Nabholtz, J. M. and Longenecker, B. M. Immunization of breast cancer patients using a synthetic sialy-Tn glycoconjugate plus DETOX adjuvant. J. Immunol. Immunother. 1993, 36, 215–222.
12. Helling, F., Shang, Y., Calves, M., Oettgen, H. F. and Livingston, P. O. Increased immunogenicity of GD3 conjugate vaccines: Comparison of various carrier proteins and selection of GD3-KLH for further testing. Cancer Res. 1994, In Press.
13. Helling, F., Adluri, S., Calves, M., Koganty, R. R., Oettgen, H. F., and Livingston, P. O. Increased immunogenicity of GM2 conjugated with KLH and used with adjuvants in patients with melanoma. Proc. Amer. Assoc. Cancer Res. 1993, 34.
14. Kensil, C. R., Soltysik, S., Patel, U. and Marciani, D. J. Structure/function relationship in adjuvants from *Quillaja spaonaria* Molina. In: Vaccines 92 (Eds. Brown, F., Chanock, R. M., Ginsberg, H., Lerner, R. A.). Cold Spring Harbor Laboratory Press, 1992, pp 35–40.
15. Kensil, C. R., Patel, U., Lennick, M. and Marciani, D. Separation and characterization of saponins with adjuvant activity from *Quillaja saponaria* Molina cortex. J. Immunol. 1991, 146, 431–437.

16. White, A. C., Cloutier, P. and Coughlin, R. T. A purified saponin acts as an adjuvant for a T-independent antigen. In: Immunobiology of Protein and Peptides VI (Ed. Atassi, M. Z.). Plenum Press, NY 1991 pp. 207–210.
17. Wu, J-Y., Gardner, B. H., Murphy, C. I., Seals, J. R., Kensil, C. R., Recchia, J., Beltz, G. A., Newman, G. W. and Newman, M. J. Saponin adjuvant enhancement of antigen-specific immune responses to an experimental HIV-1 vaccine. J. Immunol. 1992, 148, 1519–1525.
18. Newman, N. J., Wu, J-Y., Gardner, B. H., Munroe, K. J., Leombruno, D., Recchia, J, Kensil, C. R. and Coughlin, R. T. Saponin adjuvant induction of ovalbumin-specific CD8+ cytotoxic T-lymphocyte responses. J. Immunol. 1992, 148, 2357–2362.
19. Marciani, D. J., Kensil, C. R., Beltz, G. A., Hung, C- H., Cronier, J. and Aubert, A. Genetically-engineered subunit vaccine against feline leukaemia virus: protective immune response in cats. Vaccine 1991, 9, 89–96.
20. Cahan, L. D., Irie, R. F., Singh, R., Cassidenti, A. and Paulson, J. C. Identification of a neuroectodermal tumor antigen (OFA-I-2) as ganglioside GD2. Proc. Natl. Acad. Sci. USA 1982, 79, 7629–7633.
21. Dippold, W. G., Lloyd, K. O., Li, L. T. C., Ikeda, H., Oettgen, H. F. and Old, L. J. Cell surface antigens of human malignant melanoma: Definition of six antigenic systems with monoclonal antibodies. Proc. Natl. Acad. Sci. USA 1980, 77, 6114–6118.
22. Hawkes, R., Niday, E. and Gordon, J. A. Dot-immunebinding assay for monoclonal and other antibodies. Anal. Biochem. 1982, 119, 142–147.
23. Rosenberg, S. A., Lotze, M. T., Muul, L. M., Chang, A. E., Avis, F. P., Leitman, S., Linehan, W. M., Robertson, G. N., Lee, R. E., Rubin, J. T., Seipp, C. A., Simpson, C. G. and White, D. E. A progress report on the treatment of 157 patients with advanced cancer using lymphokine-activated killer cells and interleukin-2 or high-dose interleukin-2 alone. N. Engl. J. Med. 1987, 316, 789–905.
24. Del Prete, S. A., Maurer, L. H., O'Donnell, J., Forcier, R. J. and LeMarbre, P. Combination chemotherapy with cisplatin, carmustine, dacarbazine, and tamoxifen in metastatic melonama. Cancer Treat. Rep. 1984, 68, 1403–1405.
25. Mitchell, M. S., Kan-Mitchell, J., Kempf, R. A., Harel, W., Shau, H. and Lind, S. Active specific immunotherapy for melanoma: Phase I trial of allogeneic lysates and a novel adjuvant. Cancer Res. 1988, 48, 5883–5893.
26. Berd, D, Mastrangelo, M. J., Engstrom, P. F., Paul, A. and Maguire, H. Augmentation of the human immune response by cyclophosphamide. Cancer Res. 1982, 42, 4862–4866.
27. Kaplan, G., Kiessling, R., Teklemariam, S., Hancock, G., Sheftel, G., Job, C. K., Converse, P., Ottenhoff, T. H. M., Becx-Bleumink, M., Dietz, M. and Cohn, Z. A. The reconstitution of cell-mediated immunity in the cutaneous lesions of lepromatous leprosy by recombinant interleukin 2. J. Exp. Med. 1989, 169, 893.
28. Kaplan, G., Cohn, Z. A., and Smith, K. A. Rational immunotherapy with interleukin 2. Biotechnology 1992, 10, 157.

REFERENCES OF THE FIFTH SERIES OF EXPERIMENTS

1. Boring, C. C., Squires, T. S., Tong, T.: Cancer Statistics in Ca—A Cancer Journal for Clinicians. New York, N.Y., JB Lippincott Co, 1992, Vol. 42, No. 1, pp 19–38.
2. Balch, C. M., Smalley, R. V., Bartolucci, A. A., et al: A randomized prospective clinical trial of adjuvant C. parvum immunotherapy in 260 patients with clinically localized melanoma (Stage I): Prognostic factors analysis and preliminary results of immunotherapy. Cancer 49: 1079, 1982.
3. Coit, D. G., Rogatko, A., Brennan, M. F.,: Prognostic factors in patients with melanoma metastatic to axillary or inguinal lymph nodes. Ann Surg 214: 627–636, 1991.
4. Steffens, T. A., Livingston, P. O.: The status of adjuvant therapy of melanoma, in Surgical Oncology Clinics of North America. Philadelphia, Pa., W.B. Saunders Company, 1992, pp 307–333.
5. Oettgen, H. F., Livingston, P. O., Old, L. J.: Melanoma in DeVita VT Jr, Hellman S, Rosenberg S A (eds): Biologic Therapy of Cancer. Philadelphia, Pa., JB Lippincott Company, 1991, PP 682–701.
6. Livingston, P. O. Construction of cancer vaccines with carbohydrates and protein (peptide) tumor antigens. Current Opinion in Immunology 4:624–629, 1992.
7. Tai, T., Cahan, L. D., Tsuchida, T., et al: Immunogenicity of melanoma-associated gangliosides in cancer patients. Int J Cancer 35: 607–612, 1985.
8. Livingston, P. O., Natoli, E. J. Jr, Calves, M. J., et al: Vaccines containing purified GM2 ganglioside elicit GM2 antibodies in melanoma patients. Proc Natl Acad Sci USA 84: 2911–2915, 1987.
9. Livingston, P. O., Ritter, G., Srivastava, P., et al: Characterization of IgG and IgM antibodies induced in melanoma patients by immunization with purified GM2 ganglioside. Cancer Res 49: 7045–7050, 1989.
10. Greenspan, E. M.: Is BCG an "orphan" drug suffering from chemotherapists' overkill? Cancer Invest 4: 81–92, 1986.
11. Awwad, M., North, R. J.: Cyclophosphamide-induced immunologically mediated regression of a cyclophosphamide-resistant murine tumor: A consequence of eliminating precursor L3T4+ suppressor T-Cells. Cancer Res 49: 1649–1654, 1989.
12. Mokyr, M. B., Dray, S.: Some advantages of curing mice bearing a large subcutaneous MOPC-315 tumor with a low dose rather than a high dose of cyclophosphamide. Cancer Res 43: 3112–3119, 1983.
13. Natoli, E. J. Jr., Livingston, P. O., Cordon-Cardo, C., et al.; A murine monoclonal antibody detecting N-acetyl and N-glycolyl GM2: Characterization of cell surface reactivity. Cancer Res 46: 4116–4120, 1986.
14. Cahan, L. D., Irie, R. F., Singh, R., et al: Identification of a human neuroectodermal tumor antigen (OFA-I-2) as gangliside GD2. Proc Natl Acad Sci USA 79: 7629, 1982.
15. Livingston, P. O., DeLeo, A. B., Jones, M., et al: Comparison of approaches for augmenting the serological response to the Meth A antigen. Pretreatment with Cyclophosphamide is most effective. J Immunol 131: 2001, 1983.
16. Livingston, P. O., Cunningham-Rundles, S., Marfleet, G., et al: Inhibition of suppressor cell activity by cyclophosphamide in patients with malignant melanoma. J Biol Resp Mod 6: 392–403, 1987.
17. Pinsky, C. M., El Domeiri, A., Caron, A. S., et al: Delayed hypersensitivity reactions in patients with cancer. Rec Results Cancer Res 47: 37–41, 1974.
18. Livingston, P. O., Oettgen, H. F., Old, L. J.: Specific active immunotherapy in cancer therapy, in Mihich E (ed): Immunological Aspects of Cancer Therapeutics. John Wiley and Sons Inc, 1982, pp 363–404.
19. Livingston, P. O.: Active specific immunotherapy in the treatment of cancer, in Oettgen HF (ed): Immunology and Allergy Clinics of North America: Human Cancer Immunology II. London, UK, W B Saunders Co, 1991, Vol 11:2, pp 402–423.

20. Portoukalian, J., Zwingelstein, G., Dore, J.: Lipid composition of human malignant melanoma tumors at various levels of malignant growth. Europ J. Biochem 94: 19–23, 1979.
21. Tsuchida, T., Saxton, R. E., Morton, D. L., et al: Gangliosides of human melanoma. JNCI 78: 45–54, 1987.
22. Hamilton, W. B., Helling, F., Lloyd, K. O., et al: Ganglioside expression on human malignant melanoma assessed by immune thin layer chromatography. Int J Cancer 53: 566–573, 1992.
23. Watanabe, T., Pukel, C. S., Takeyama, H., et al: Human melanoma antigen AH is an autoantigenic ganglioside related to GD2. J Exp Med 156: 1884–1889, 1982.
24. Pukel, C. S., Lloyd, K. O., Travassos, L. R., et al: GD3, a prominent ganglioside of human melanoma detection and characterization by mouse monoclonal antibody. J Exp Med 155: 1133–1147, 1982.
25. Tai, T., Paulson, J. C., Cahan, L. D., et al: Ganglioside GM2 as a human tumor antigen (OFA-I-1). Proc Natl Acad Sci USA 80: 5392–5396, 1983.
26. Furukawa, K., Yamaguchi, H., Oettgen, H. F., et al: Two human monoclonal antibodies reacting with the major gangliosides of human melanomas and comparison with corresponding mouse monoclonal antibodies. Cancer Res 49: 191–196, 1989.
27. Yamaguchi, H., Furukawa, K., Fortunato, S. R., et al: Cell-surface antigens of melanoma recognized by human monoclonal antibodies. Proc Natl Acad Sci USA 84: 2416–2420, 1987.
28. Yamaguchi, H., Furukawa, K., Fortunato, S. R., et al: Human monoclonal antibody with dual GM2/GD2 specificity derived from an immunized melanoma patient. Proc Natl Acad Sci USA 87: 3333–3337, 1990.
29. Welt, S., Carswell, E. A., Vogel, C-W., et al: Immune and nonimmune effector functions of IgG3 mouse monoclonal antibody R24 detecting the disialoganglioside GD3 on the surface of melanoma cells. Clin Immunol Immunopath 45: 214–229, 1987.
30. Irie, R. F.: Oncofetal antigen (OFA-I): A human tumor-associated fetal antigen immunogenic in man, in Rosenberg S (ed): Serological analysis of human cancer. New York, N.Y., Academic Press, 1980, pp 493–513.
31. Jones, P. C., Sze, L. L., Liu, P. Y., et al: Prolonged survival for melanoma patients with elevated IgM antibody to oncofetal antigen. JNCI 66: 249–254, 1981.
32. Bell, R., Torrigiani, G. (eds): Towards Better Carbohydrate Vaccines. New York, John Wiley & Sons Ltd, pp 1–363, 1987.
33. Ritter, G., Boosfeld, E., Calves, M. J., et al: Antibody response after immunization with gangliosides GD3, GD3 lactones, GD3 amide and GD3 gangliosidol in the mouse. GD3 lactone I induces antibodies reactive with human melanoma. Immunobiology 182: 32–43, 1990.
34. Ritter, G., Livingston, P. O.: Cancer associated ganglioside antigens, in Longenecker M (ed): Seminars in Cancer Biology, London, UK, W B Saunders, 1991, Vol 2: 40–409.
35. Helling, F., Shang, Y., Calves, M., et al: GD3 vaccines for melanoma: Superior immunogenicity of KLH conjugate vaccines. Cancer Res, January 1994, In Press.
36. Livingston, P. O., Koganty, R., Longenecker, B. M., et al: Studies on the immunogenicity of synthetic and natural Thomsen-Friedenreich (TF) antigens in mice: Augmentation of the response by Quil A and SAF-m adjuvants and analysis of the specificity of the response. Vaccine Res 1: 99–109, 1992.
37. Helling, F., Adluri, S., Calves, M., et al: Increased immunogenicity of GM2 conjugated with KLH and used with adjuvants in patients with melanoma. Proc Amer Assoc Cancer Res 34: 491, 1993.
38. Svennerholm, L., Chromatographic separation of human brain gangliosides. J Neurochem 10: 613–623, 1963.

What is claimed is:

1. A composition which comprises:

(a) a conjugate of (i) a derivative of a ganglioside, which ganglioside is a GM2 or GD2 ganglioside and comprises an unaltered sphingosine base, wherein the derivative differs from the ganglioside solely by having an altered sphingosine base which retains only C1 through C4 from the unaltered sphingosine base of the ganglioside, and (ii) Keyhole Limpet Hemocyanin, wherein the GM2 or GD2 ganglioside derivative is covalently bound to Keyhole Limpet Hemocyanin by a stable amine bond between the C-4 carbon of the altered sphingosine base and a nitrogen of an ε-aminolysyl group of Keyhole Limpet Hemocyanin;

(b) QS-21; and (c) a pharmaceutically acceptable carrier;

wherein the amount of the conjugated GM2 or GD2 ganglioside derivative is an amount between about 1 μg and about 200 μg, the amount of QS-21 is an amount between about 10 μg and about 200 μg, the GM2 derivative or GD2 derivative:Keyhole Limpet Hemocyanin molar ratio is from 200:1 to 1400:1, and the relative amounts of such conjugate and QS-21 is effective to stimulate or enhance production in a subject of an antibody to GM2 or GD2 ganglioside.

2. The composition of claim 1 wherein the ganglioside derivative is a GM2 ganglioside derivative and wherein the amount of the conjugated GM2 ganglioside derivative is an amount of about 30 μg.

3. The composition of claim 1 wherein the ganglioside derivative is a GD2 ganglioside derivative and wherein the amount of the conjugated GD2 ganglioside derivative is an amount of about 70 μg.

4. The composition of claim 1 wherein the amount of QS-21 is about 50 μg.

5. The composition of claim 1, wherein the amount of QS-21 is about 200 μg.

6. A composition of claim 1 which comprises:

(a) a conjugate of (i) a derivative of a ganglioside, which ganglioside is a GM2 or GD2 ganglioside and comprises an unaltered sphingosine base, wherein the derivative differs from the ganglioside solely by having an altered sphingosine base which retains only C1 through C4 from the unaltered sphingosine base of the ganglioside, and (ii) Keyhole Limpet Hemocyanin, wherein the GM2 or GD2 ganglioside derivative is covalently bound to Keyhole Limpet Hemocyanin by a stable amine bond between the C-4 carbon of the altered sphingosine base and a nitrogen of an ε-aminolysyl group of Keyhole Limpet Hemocyanin;

(b) QS-21; and (c) a pharmaceutically acceptable carrier;

wherein the amount of the conjugated GM2 or GD2 ganglioside derivative is an amount between about 1 μg and about 200 μg, the amount of QS-21 is about 100 μg, the GM2 derivative or GD2 derivative:Keyhole Limpet Hemocyanin molar ratio is from 200:1 to 1400:1, and the relative amounts of such conjugate and QS-21 is effective to stimulate or enhance production in a subject of an antibody to GM2 or GD2 ganglioside.

7. A method of treating a subject afflicted with melanoma which comprises administering to said subject an amount of the composition of claim 6 effective to stimulate or enhance production of an antibody directed to at least one of GM2 and GD2 and to thereby treat said melanoma in said subject.

8. A method of stimulating or enhancing production of an antibody directed to GM2 or GD2 in a subject which comprises administering to the subject an effective amount of a composition which comprises:

(a) a conjugate of (i) a derivative of a ganglioside, which ganglioside is a GM2 or GD2 ganglioside and comprises an unaltered sphingosine base, wherein the derivative differs from the ganglioside solely by having an altered sphingosine base which retains only C1 through C4 from the unaltered sphingosine base of the ganglioside, and (ii) Keyhole Limpet Hemocyanin, wherein the GM2 or GD2 ganglioside derivative is covalently bound to Keyhole Limpet Hemocyanin by a stable amine bond between the C-4 carbon of the altered sphingosine base and a nitrogen of an ε-aminolysyl group of Keyhole Limpet Hemocyanin;

(b) QS-21; and (c) a pharmaceutically acceptable carrier;

wherein the amount of the conjugated GM2 or GD2 ganglioside derivative is an amount between about 1 μg and about 200 μg, the amount of QS-21 is an amount between about 10 μg and about 200 μg, the GM2 derivative or GD2 derivative:Keyhole Limpet Hemocyanin molar ratio is from 200:1 to 1400:1, and the relative amounts of such conjugate and QS-21 is effective to stimulate or enhance production in a subject of an antibody to GM2 or GD2 ganglioside.

9. A method of treating a human subject having a cancer which comprises administering to the subject an effective cancer-treating amount of a composition which comprises:

(a) a conjugate of (i) a derivative of a ganglioside, which ganglioside is a GM2 or GD2 ganglioside and comprises an unaltered sphingosine base, wherein the derivative differs from the ganglioside solely by having an altered sphingosine base which retains only C1 through C4 from the unaltered sphingosine base of the ganglioside, and (ii) Keyhole Limpet Hemocyanin, wherein the GM2 or GD2 ganglioside derivative is covalently bound to Keyhole Limpet Hemocyanin by a stable amine bond between the C4 carbon of the altered sphingosine base and a nitrogen of an ε-aminolysyl group of Keyhole Limpet Hemocyanin;

(b) QS-21; and (c) a pharmaceutically acceptable carrier;

wherein the amount of the conjugated GM2 or GD2 ganglioside derivative is an amount between about 1 μg and about 200 μg, the amount of QS-21 is an amount between about 10 μg and about 200 μg, the GM2 derivative or GD2 derivative:Keyhole Limpet Hemocyanin molar ratio is from 200:1 to 1400:1, and the relative amounts of such conjugate and QS-21 is effective to stimulate or enhance production in a subject of an antibody to GM2 or GD2 ganglioside.

10. The method of claim 9, wherein the cancer is of epithelial origin.

11. The method of claim 9, wherein the cancer is of neuroectodermal origin.

12. The method of claim 11, wherein the cancer of neuroectodermal origin is melanoma.

13. The method of claim 8 or 9, wherein the administering is effected at two or more sites.

14. The method of claim 13, wherein the administering is effected at three sites.

15. The method of claim 8 or 9, wherein the composition is administered subcutaneously to said subject.

16. The method of claim 15, wherein the composition is administered to said subject at two-week intervals.

17. The method of claim 15, wherein the composition is initially administered to said subject at weekly intervals.

18. The method of claim 8 or 9, wherein the composition to be administered is prepared prior to administration to the subject by mixing the conjugate and QS-21.

19. The method of claim 18, wherein the conjugate and QS-21 are mixed on the day of administration to the subject.

* * * * *

UNITED STATES PATENT AND TRADEMARK OFFICE
CERTIFICATE OF CORRECTION

PATENT NO. : 6,936,253 B1  
APPLICATION NO. : 08/477097  
DATED : August 30, 2005  
INVENTOR(S) : Livingston et al.

Page 1 of 1

It is certified that error appears in the above-identified patent and that said Letters Patent is hereby corrected as shown below:

In column 1, beginning at line 8 and ending at line 10, please delete:

"This invention was made with support under Government Grant No. RO1 CA40532. Accordingly, the U.S. Government has certain rights in the invention."

and insert:

--This invention was made with government support under grant numbers CA008748 and CA040532 awarded by The National Institutes of Health. The government has certain rights in the invention.--

Signed and Sealed this  
Twenty-ninth Day of March, 2016

Michelle K. Lee  
*Director of the United States Patent and Trademark Office*